(12) United States Patent
Shelton, IV et al.

(10) Patent No.: US 11,696,776 B2
(45) Date of Patent: Jul. 11, 2023

(54) ARTICULATABLE SURGICAL INSTRUMENT

(71) Applicant: Cilag GmbH International, Zug (CH)

(72) Inventors: Frederick E. Shelton, IV, Hillsboro, OH (US); Kevin M. Fiebig, Cincinnati, OH (US); Mark S. Zeiner, Mason, OH (US)

(73) Assignee: Cilag GmbH International, Zug (CH)

( * ) Notice: Subject to any disclaimer, the term of this patent is extended or adjusted under 35 U.S.C. 154(b) by 152 days.

(21) Appl. No.: 16/885,820

(22) Filed: May 28, 2020

(65) Prior Publication Data

US 2021/0196301 A1 Jul. 1, 2021

Related U.S. Application Data

(60) Provisional application No. 62/955,299, filed on Dec. 30, 2019.

(51) Int. Cl.
| | | |
|---|---|---|
| *A61B 17/29* | (2006.01) | |
| *A61B 17/068* | (2006.01) | |
| *A61B 8/00* | (2006.01) | |
| *A61B 1/01* | (2006.01) | |
| *A61B 1/00* | (2006.01) | |
| *A61B 1/008* | (2006.01) | |
| *A61B 1/005* | (2006.01) | |

(52) U.S. Cl.
CPC ............ *A61B 17/29* (2013.01); *A61B 17/068* (2013.01); *A61B 1/008* (2013.01); *A61B 1/009* (2022.02); *A61B 1/00149* (2013.01); *A61B 1/01* (2013.01); *A61B 8/4218* (2013.01); *A61B 2017/2908* (2013.01); *A61B 2017/2919* (2013.01); *A61B 2017/2939* (2013.01)

(58) Field of Classification Search
CPC ..... A61B 8/4218; A61B 17/29; A61B 17/068; A61B 2017/2919; A61B 2017/2939; A61B 2017/2908; A61B 1/00149
See application file for complete search history.

(56) References Cited

U.S. PATENT DOCUMENTS

| 969,528 A | 9/1910 | Disbrow |
|---|---|---|
| 1,570,025 A | 1/1926 | Young |
| (Continued) | | |

FOREIGN PATENT DOCUMENTS

| CA | 2535467 A1 | 4/1993 |
|---|---|---|
| CN | 2460047 Y | 11/2001 |
| (Continued) | | |

OTHER PUBLICATIONS

Covidien Brochure, [Value Analysis Brief], LiGaSure Advance™ Pistol Grip, dated Rev. Apr. 2010 (7 pages).
(Continued)

*Primary Examiner* — Timothy J Neal
*Assistant Examiner* — Mitchell Brian Hoag

(57) ABSTRACT

A surgical instrument that includes a surgical end effector that is articulatable relative to a proximal shaft segment of the surgical instrument. The surgical end effector is attached to the proximal shaft segment by an articulation joint that comprises a plurality of movably interconnected links that interface with a centrally disposed drive member to apply articulation motions thereto and which serve to provide improved lateral stability to the articulation joint.

23 Claims, 72 Drawing Sheets

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |

(56) References Cited

U.S. PATENT DOCUMENTS

| | | |
|---|---|---|
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A * | 7/1994 | Hassler .............. A61B 17/29 |
| | | 606/174 |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |

(56) References Cited

U.S. PATENT DOCUMENTS

| | | |
|---|---|---|
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |

(56) References Cited

U.S. PATENT DOCUMENTS

| | | |
|---|---|---|
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |

(56) References Cited

U.S. PATENT DOCUMENTS

| | | |
|---|---|---|
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |

(56) References Cited

U.S. PATENT DOCUMENTS

| | | |
|---|---|---|
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |

(56) References Cited

U.S. PATENT DOCUMENTS

| | | |
|---|---|---|
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |

(56) References Cited

U.S. PATENT DOCUMENTS

| | | |
|---|---|---|
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 * | 8/2010 | Shelton, IV ......... A61B 17/072 606/139 |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |

(56) References Cited

U.S. PATENT DOCUMENTS

| | | |
|---|---|---|
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilia et al. |
| 8,056,720 B2 | 11/2011 | Hawkes |
| 8,056,787 B2 | 11/2011 | Boudreaux et al. |
| 8,057,468 B2 | 11/2011 | Esky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |

(56) References Cited

U.S. PATENT DOCUMENTS

| | | |
|---|---|---|
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |

(56) References Cited

U.S. PATENT DOCUMENTS

| | | |
|---|---|---|
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 * | 6/2014 | Shelton, IV ............ A61B 34/37 464/57 |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 8/2014 | Shelton, IV |
| 8,821,388 B2 * | 9/2014 | Naito .................... A61B 34/71 600/149 |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |

(56) References Cited

U.S. PATENT DOCUMENTS

| | | |
|---|---|---|
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 * | 5/2015 | Mueller ............ A61B 18/1445 606/41 |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 * | 9/2015 | Shelton, IV ............ A61B 34/37 |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 * | 10/2015 | Huang ............... A61B 18/1445 |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |

(56) References Cited

U.S. PATENT DOCUMENTS

| | | | |
|---|---|---|---|
| 9,198,714 | B2 | 12/2015 | Worrell et al. |
| 9,198,715 | B2 | 12/2015 | Livneh |
| 9,198,718 | B2 | 12/2015 | Marczyk et al. |
| 9,198,776 | B2 | 12/2015 | Young |
| 9,204,879 | B2 * | 12/2015 | Shelton, IV ....... A61B 18/1445 |
| 9,204,891 | B2 | 12/2015 | Weitzman |
| 9,204,918 | B2 | 12/2015 | Germain et al. |
| 9,204,923 | B2 | 12/2015 | Manzo et al. |
| 9,216,050 | B2 | 12/2015 | Condie et al. |
| 9,216,051 | B2 | 12/2015 | Fischer et al. |
| 9,216,062 | B2 | 12/2015 | Duque et al. |
| 9,220,483 | B2 | 12/2015 | Frankhouser et al. |
| 9,220,527 | B2 | 12/2015 | Houser et al. |
| 9,220,559 | B2 * | 12/2015 | Worrell ............. A61B 18/1445 |
| 9,226,750 | B2 | 1/2016 | Weir et al. |
| 9,226,751 | B2 | 1/2016 | Shelton, IV et al. |
| 9,226,766 | B2 | 1/2016 | Aldridge et al. |
| 9,226,767 | B2 | 1/2016 | Stulen et al. |
| 9,232,979 | B2 | 1/2016 | Parihar et al. |
| 9,237,891 | B2 | 1/2016 | Shelton, IV |
| 9,237,921 | B2 | 1/2016 | Messerly et al. |
| 9,241,060 | B1 | 1/2016 | Fujisaki |
| 9,241,692 | B2 | 1/2016 | Gunday et al. |
| 9,241,728 | B2 | 1/2016 | Price et al. |
| 9,241,730 | B2 | 1/2016 | Babaev |
| 9,241,731 | B2 | 1/2016 | Boudreaux et al. |
| 9,241,768 | B2 | 1/2016 | Sandhu et al. |
| 9,247,953 | B2 | 2/2016 | Palmer et al. |
| 9,254,165 | B2 | 2/2016 | Aronow et al. |
| 9,259,234 | B2 | 2/2016 | Robertson et al. |
| 9,259,265 | B2 | 2/2016 | Harris et al. |
| 9,265,567 | B2 | 2/2016 | Orban, III et al. |
| 9,265,926 | B2 | 2/2016 | Strobl et al. |
| 9,265,973 | B2 | 2/2016 | Akagane |
| 9,266,310 | B2 | 2/2016 | Krogdahl et al. |
| 9,277,962 | B2 | 3/2016 | Koss et al. |
| 9,282,974 | B2 | 3/2016 | Shelton, IV |
| 9,283,027 | B2 | 3/2016 | Monson et al. |
| 9,283,045 | B2 | 3/2016 | Rhee et al. |
| 9,283,054 | B2 | 3/2016 | Morgan et al. |
| 9,289,256 | B2 | 3/2016 | Shelton, IV et al. |
| 9,295,514 | B2 | 3/2016 | Shelton, IV et al. |
| 9,301,759 | B2 | 4/2016 | Spivey et al. |
| 9,305,497 | B2 | 4/2016 | Seo et al. |
| 9,307,388 | B2 | 4/2016 | Liang et al. |
| 9,307,986 | B2 | 4/2016 | Hall et al. |
| 9,308,009 | B2 | 4/2016 | Madan et al. |
| 9,308,014 | B2 | 4/2016 | Fischer |
| 9,314,261 | B2 | 4/2016 | Bales, Jr. et al. |
| 9,314,292 | B2 | 4/2016 | Trees et al. |
| 9,314,301 | B2 | 4/2016 | Ben-Haim et al. |
| 9,326,754 | B2 | 5/2016 | Polster |
| 9,326,767 | B2 | 5/2016 | Koch et al. |
| 9,326,787 | B2 | 5/2016 | Sanai et al. |
| 9,326,788 | B2 | 5/2016 | Batross et al. |
| 9,332,987 | B2 | 5/2016 | Leimbach et al. |
| 9,333,025 | B2 | 5/2016 | Monson et al. |
| 9,333,034 | B2 | 5/2016 | Hancock |
| 9,339,289 | B2 | 5/2016 | Robertson |
| 9,339,323 | B2 | 5/2016 | Eder et al. |
| 9,339,326 | B2 | 5/2016 | McCullagh et al. |
| 9,345,481 | B2 | 5/2016 | Hall et al. |
| 9,345,534 | B2 | 5/2016 | Artale et al. |
| 9,345,900 | B2 | 5/2016 | Wu et al. |
| 9,351,642 | B2 | 5/2016 | Nadkarni et al. |
| 9,351,726 | B2 | 5/2016 | Leimbach et al. |
| 9,351,727 | B2 | 5/2016 | Leimbach et al. |
| 9,351,754 | B2 | 5/2016 | Vakharia et al. |
| 9,352,173 | B2 | 5/2016 | Yamada et al. |
| 9,358,003 | B2 | 6/2016 | Hall et al. |
| 9,358,065 | B2 | 6/2016 | Ladtkow et al. |
| 9,364,171 | B2 | 6/2016 | Harris et al. |
| 9,364,230 | B2 | 6/2016 | Shelton, IV et al. |
| 9,364,279 | B2 | 6/2016 | Houser et al. |
| 9,370,364 | B2 | 6/2016 | Smith et al. |
| 9,370,400 | B2 | 6/2016 | Parihar |
| 9,370,611 | B2 | 6/2016 | Ross et al. |
| 9,375,230 | B2 | 6/2016 | Ross et al. |
| 9,375,232 | B2 | 6/2016 | Hunt et al. |
| 9,375,256 | B2 | 6/2016 | Cunningham et al. |
| 9,375,264 | B2 | 6/2016 | Horner et al. |
| 9,375,267 | B2 | 6/2016 | Kerr et al. |
| 9,385,831 | B2 | 7/2016 | Marr et al. |
| 9,386,983 | B2 | 7/2016 | Swensgard et al. |
| 9,393,037 | B2 | 7/2016 | Olson et al. |
| 9,393,070 | B2 | 7/2016 | Gelfand et al. |
| 9,398,911 | B2 | 7/2016 | Auld |
| 9,402,680 | B2 | 8/2016 | Ginnebaugh et al. |
| 9,402,682 | B2 | 8/2016 | Worrell et al. |
| 9,408,606 | B2 | 8/2016 | Shelton, IV |
| 9,408,622 | B2 | 8/2016 | Stulen et al. |
| 9,408,660 | B2 | 8/2016 | Strobl et al. |
| 9,414,853 | B2 | 8/2016 | Stulen et al. |
| 9,414,880 | B2 | 8/2016 | Monson et al. |
| 9,421,014 | B2 | 8/2016 | Ingmanson et al. |
| 9,421,060 | B2 | 8/2016 | Monson et al. |
| 9,427,249 | B2 | 8/2016 | Robertson et al. |
| 9,427,279 | B2 | 8/2016 | Muniz-Medina et al. |
| 9,439,668 | B2 | 9/2016 | Timm et al. |
| 9,439,669 | B2 | 9/2016 | Wiener et al. |
| 9,439,671 | B2 | 9/2016 | Akagane |
| 9,442,288 | B2 | 9/2016 | Tanimura |
| 9,445,784 | B2 | 9/2016 | O'Keeffe |
| 9,445,832 | B2 | 9/2016 | Wiener et al. |
| 9,451,967 | B2 | 9/2016 | Jordan et al. |
| 9,456,863 | B2 | 10/2016 | Moua |
| 9,456,864 | B2 | 10/2016 | Witt et al. |
| 9,468,438 | B2 | 10/2016 | Baber et al. |
| 9,468,498 | B2 | 10/2016 | Sigmon, Jr. |
| 9,474,542 | B2 | 10/2016 | Slipszenko et al. |
| 9,474,568 | B2 | 10/2016 | Akagane |
| 9,486,236 | B2 | 11/2016 | Price et al. |
| 9,492,146 | B2 | 11/2016 | Kostrzewski et al. |
| 9,492,224 | B2 | 11/2016 | Boudreaux et al. |
| 9,498,245 | B2 | 11/2016 | Voegele et al. |
| 9,498,275 | B2 | 11/2016 | Wham et al. |
| 9,504,483 | B2 | 11/2016 | Houser et al. |
| 9,504,520 | B2 | 11/2016 | Worrell et al. |
| 9,504,524 | B2 | 11/2016 | Behnke, II |
| 9,504,855 | B2 | 11/2016 | Messerly et al. |
| 9,510,850 | B2 | 12/2016 | Robertson et al. |
| 9,510,906 | B2 | 12/2016 | Boudreaux et al. |
| 9,522,029 | B2 | 12/2016 | Yates et al. |
| 9,522,032 | B2 | 12/2016 | Behnke |
| 9,526,564 | B2 | 12/2016 | Rusin |
| 9,526,565 | B2 | 12/2016 | Strobl |
| 9,545,253 | B2 | 1/2017 | Worrell et al. |
| 9,545,497 | B2 | 1/2017 | Wenderow et al. |
| 9,554,465 | B1 | 1/2017 | Liu et al. |
| 9,554,794 | B2 | 1/2017 | Baber et al. |
| 9,554,846 | B2 | 1/2017 | Boudreaux |
| 9,554,854 | B2 | 1/2017 | Yates et al. |
| 9,560,995 | B2 | 2/2017 | Addison et al. |
| 9,561,038 | B2 | 2/2017 | Shelton, IV et al. |
| 9,572,592 | B2 | 2/2017 | Price et al. |
| 9,574,644 | B2 | 2/2017 | Parihar |
| 9,585,714 | B2 | 3/2017 | Livneh |
| 9,592,056 | B2 | 3/2017 | Mozdzierz et al. |
| 9,592,072 | B2 | 3/2017 | Akagane |
| 9,597,143 | B2 | 3/2017 | Madan et al. |
| 9,603,669 | B2 | 3/2017 | Govari et al. |
| 9,610,091 | B2 | 4/2017 | Johnson et al. |
| 9,610,114 | B2 | 4/2017 | Baxter, III et al. |
| 9,615,877 | B2 | 4/2017 | Tyrrell et al. |
| 9,623,237 | B2 | 4/2017 | Turner et al. |
| 9,629,623 | B2 | 4/2017 | Lytle, IV et al. |
| 9,629,629 | B2 | 4/2017 | Leimbach et al. |
| 9,632,573 | B2 | 4/2017 | Ogawa et al. |
| 9,636,135 | B2 | 5/2017 | Stulen |
| 9,636,165 | B2 | 5/2017 | Larson et al. |
| 9,636,167 | B2 | 5/2017 | Gregg |
| 9,638,770 | B2 | 5/2017 | Dietz et al. |
| 9,642,644 | B2 | 5/2017 | Houser et al. |
| 9,642,669 | B2 | 5/2017 | Takashino et al. |

(56) References Cited

U.S. PATENT DOCUMENTS

| | | |
|---|---|---|
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,860 B2 | 2/2018 | Leimbach |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |

(56) References Cited

U.S. PATENT DOCUMENTS

| | | |
|---|---|---|
| 10,117,649 B2 | 11/2018 | Baxter et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |

(56) References Cited

U.S. PATENT DOCUMENTS

| | | |
|---|---|---|
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |

(56) References Cited

U.S. PATENT DOCUMENTS

| | | |
|---|---|---|
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,559,347 B2 * | 1/2023 | Wiener ............... A61B 18/1445 |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 * | 9/2004 | Taniguchi ............... A61B 17/29<br>606/205 |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |

(56) References Cited

U.S. PATENT DOCUMENTS

| | | |
|---|---|---|
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iijima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |

(56) References Cited

U.S. PATENT DOCUMENTS

| | | |
|---|---|---|
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131934 A1 | 5/2009 | Odom et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0071561 A1* | 3/2011 | Prestel .................. A61B 17/29 606/174 |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0199632 A1* | 8/2012 | Spivey .......... A61B 17/320016 227/176.1 |
| 2012/0211542 A1 | 8/2012 | Racenet |
| 2012/0226266 A1* | 9/2012 | Ghosal .................. A61B 17/29 606/1 |
| 2012/0234893 A1 | 9/2012 | Schuckmann et al. |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0103031 A1 | 4/2013 | Garrison |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |

(56) References Cited

U.S. PATENT DOCUMENTS

| | | |
|---|---|---|
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0373003 A1 | 12/2014 | Grez et al. |
| 2015/0014392 A1 | 1/2015 | Williams et al. |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1* | 4/2015 | Steege .................. A61B 34/70 606/130 |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2016/0000437 A1 | 1/2016 | Giordano et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051316 A1 | 2/2016 | Boudreaux |
| 2016/0066909 A1 | 3/2016 | Swayze et al. |
| 2016/0066913 A1 | 3/2016 | Swayze et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0358849 A1 | 12/2016 | Jur et al. |
| 2016/0367255 A1* | 12/2016 | Wise .................... A61B 17/068 |
| 2016/0367256 A1* | 12/2016 | Hensel ................ A61B 17/068 |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0224332 A1 | 8/2017 | Hunter et al. |
| 2017/0224342 A1* | 8/2017 | Worthington .......... A61B 17/32 |
| 2017/0231628 A1 | 8/2017 | Shelton, IV et al. |
| 2017/0245933 A1* | 8/2017 | Graham ............... A61B 18/201 |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2018/0014872 A1 | 1/2018 | Dickerson |
| 2018/0098785 A1 | 4/2018 | Price et al. |
| 2018/0132850 A1 | 5/2018 | Leimbach et al. |
| 2018/0146976 A1 | 5/2018 | Clauda et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1* | 7/2018 | Felder ................ A61B 18/1445 |
| 2018/0221045 A1 | 8/2018 | Zimmerman et al. |
| 2018/0235691 A1 | 8/2018 | Voegele et al. |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0353245 A1 | 12/2018 | McCloud et al. |
| 2018/0368843 A1 | 12/2018 | Shelton, IV et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038282 A1 | 2/2019 | Shelton, IV et al. |
| 2019/0038283 A1 | 2/2019 | Shelton, IV et al. |
| 2019/0104919 A1 | 4/2019 | Shelton, IV et al. |
| 2019/0105067 A1 | 4/2019 | Boudreaux et al. |
| 2019/0125384 A1 | 5/2019 | Scheib et al. |
| 2019/0125390 A1* | 5/2019 | Shelton, IV ....... A61B 17/2841 |
| 2019/0183504 A1* | 6/2019 | Shelton, IV ....... A61B 17/0682 |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201020 A1 | 7/2019 | Shelton, IV et al. |
| 2019/0201023 A1 | 7/2019 | Shelton, IV et al. |
| 2019/0201030 A1 | 7/2019 | Shelton, IV et al. |

(56) References Cited

U.S. PATENT DOCUMENTS

| | | |
|---|---|---|
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209201 A1 | 7/2019 | Boudreaux et al. |
| 2019/0223941 A1 | 7/2019 | Kitamura et al. |
| 2019/0262030 A1 | 8/2019 | Faller et al. |
| 2019/0269455 A1 | 9/2019 | Mensch et al. |
| 2019/0274700 A1 | 9/2019 | Robertson et al. |
| 2019/0282288 A1 | 9/2019 | Boudreaux |
| 2019/0290265 A1 | 9/2019 | Shelton, IV et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0030021 A1 | 1/2020 | Yates et al. |
| 2020/0054321 A1 | 2/2020 | Harris et al. |
| 2020/0054382 A1 | 2/2020 | Yates et al. |
| 2020/0078076 A1 | 3/2020 | Henderson et al. |
| 2020/0078085 A1 | 3/2020 | Yates et al. |
| 2020/0078106 A1 | 3/2020 | Henderson et al. |
| 2020/0078609 A1 | 3/2020 | Messerly et al. |
| 2020/0085465 A1 | 3/2020 | Timm et al. |
| 2020/0100825 A1 | 4/2020 | Henderson et al. |
| 2020/0100830 A1 | 4/2020 | Henderson et al. |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261075 A1 | 8/2020 | Boudreaux et al. |
| 2020/0261078 A1 | 8/2020 | Bakos et al. |
| 2020/0261081 A1 | 8/2020 | Boudreaux et al. |
| 2020/0261083 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261141 A1 | 8/2020 | Wiener et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0338370 A1 | 10/2020 | Wiener et al. |
| 2020/0405296 A1 | 12/2020 | Shelton, IV et al. |
| 2020/0405302 A1 | 12/2020 | Shelton, IV et al. |
| 2020/0405312 A1 | 12/2020 | Shelton, IV et al. |
| 2020/0405314 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1* | 6/2021 | Shelton, IV ......... A61B 17/072 |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1* | 6/2021 | Shelton, IV ..... A61B 17/07207 |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186507 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |
| 2022/0304736 A1 | 9/2022 | Boudreaux |
| 2022/0313297 A1 | 10/2022 | Aldridge et al. |
| 2022/0346863 A1 | 11/2022 | Yates et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |

(56) References Cited

FOREIGN PATENT DOCUMENTS

| | | |
|---|---|---|
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3547324 A1 * | 10/2019 ......... A61B 17/0682 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |

(56) References Cited

FOREIGN PATENT DOCUMENTS

| WO | WO-2011052939 A2 | 5/2011 |
|---|---|---|
| WO | WO-2011060031 A1 | 5/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wall et al., "Thermal modification of collagen," J Shoulder Elbow Surg, No. 8, pp. 339-344 (Jul./Aug. 1999).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan.

1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C.," Journal of Biomechanics, 31, pp. 211-216 (1998).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital/l/ge . . . .
http://www.medicalexpo.com/medical-manufacturer/electrosurgical-generator-6951.html.
http://www.megadyne.com/es_generator.php.
http://www.valleylab.com/product/es/generators/index.html.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Walsh, S. J., White, R. G., "Vibrational Power Transmission in Curved Beams," Journal of Sound and Vibration, 233(3), 455-488 (2000).
Covidien 501 (k) Summary Sonicision, dated Feb. 24, 2011 (7 pages).
Morley, L. S. D., "Elastic Waves in a Naturally Curved Rod," Quarterly Journal of Mechanics and Applied Mathematics, 14: 155-172 (1961).
Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191 .asp (15 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Campbell et al., "Thermal Imaging in Surgery," p. 19-3, in Medical Infrared Imaging, N. A. Diakides and J. D. Bronzino, Eds. (2008).

(56) References Cited

OTHER PUBLICATIONS

Gerhard, Glen C., "Surgical Electrotechnology: Quo Vadis?," IEEE Transactions on Biomedical Engineering, vol. BME-31, No. 12, pp. 787-792, Dec. 1984.
http://www.4-traders.com/JOHNSON-JOHNSQN-4832/news/Johnson-Johnson-Ethicon-E . . . .
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Kurt Gieck & Reiner Gieck, *Engineering Formulas* § Z.7 (7th ed. 1997).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Erbe Electrosurgery VIO® 200 S, (2012), p. 7, 12 pages, accessed Mar. 31, 2014 at http://www. erbe-med. com/erbe/media/Marketing materialien/85140170 ERBE EN VIO 200 S D027541.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.
IEEE Std 802.Mar. 2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).

\* cited by examiner

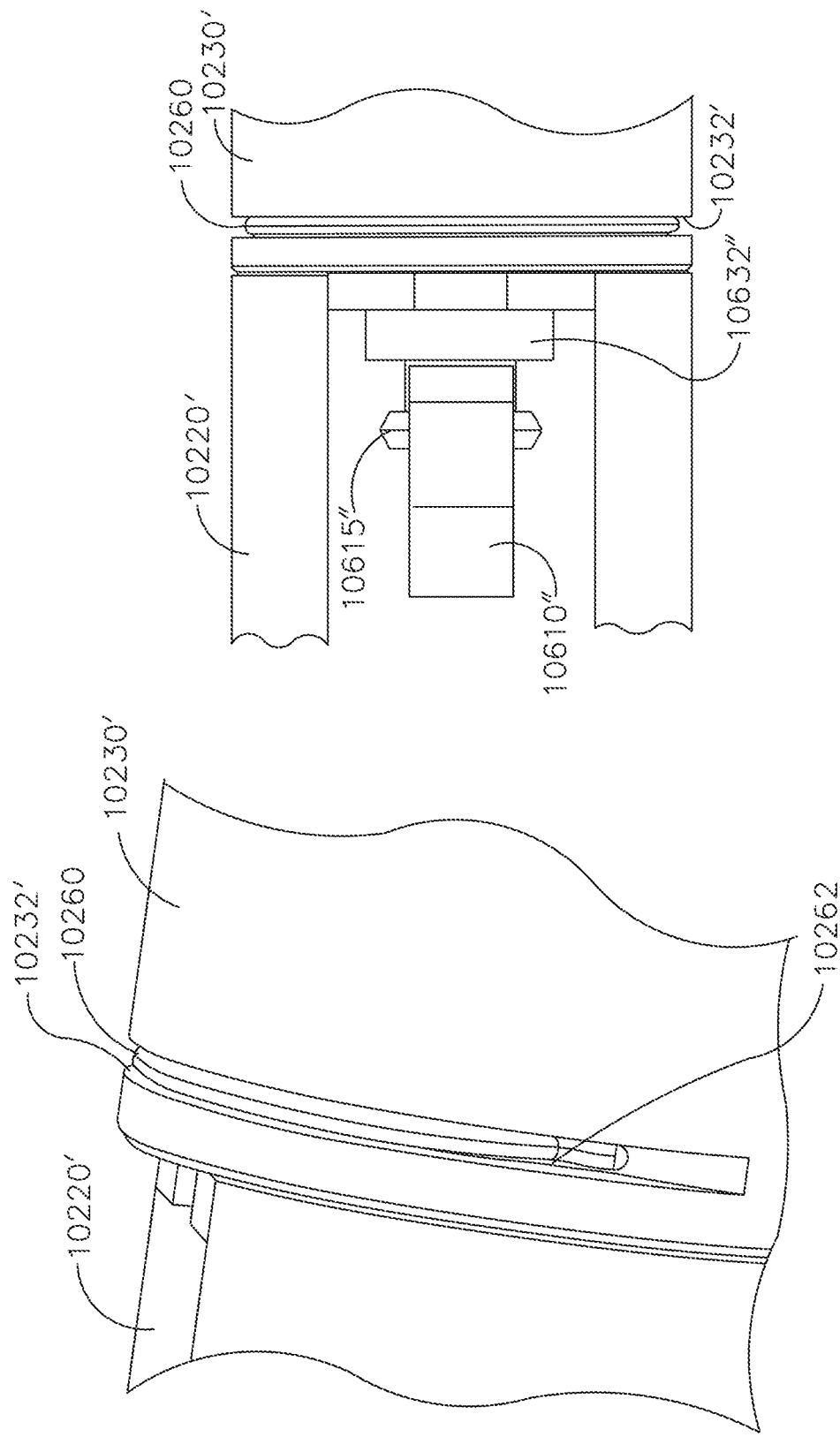

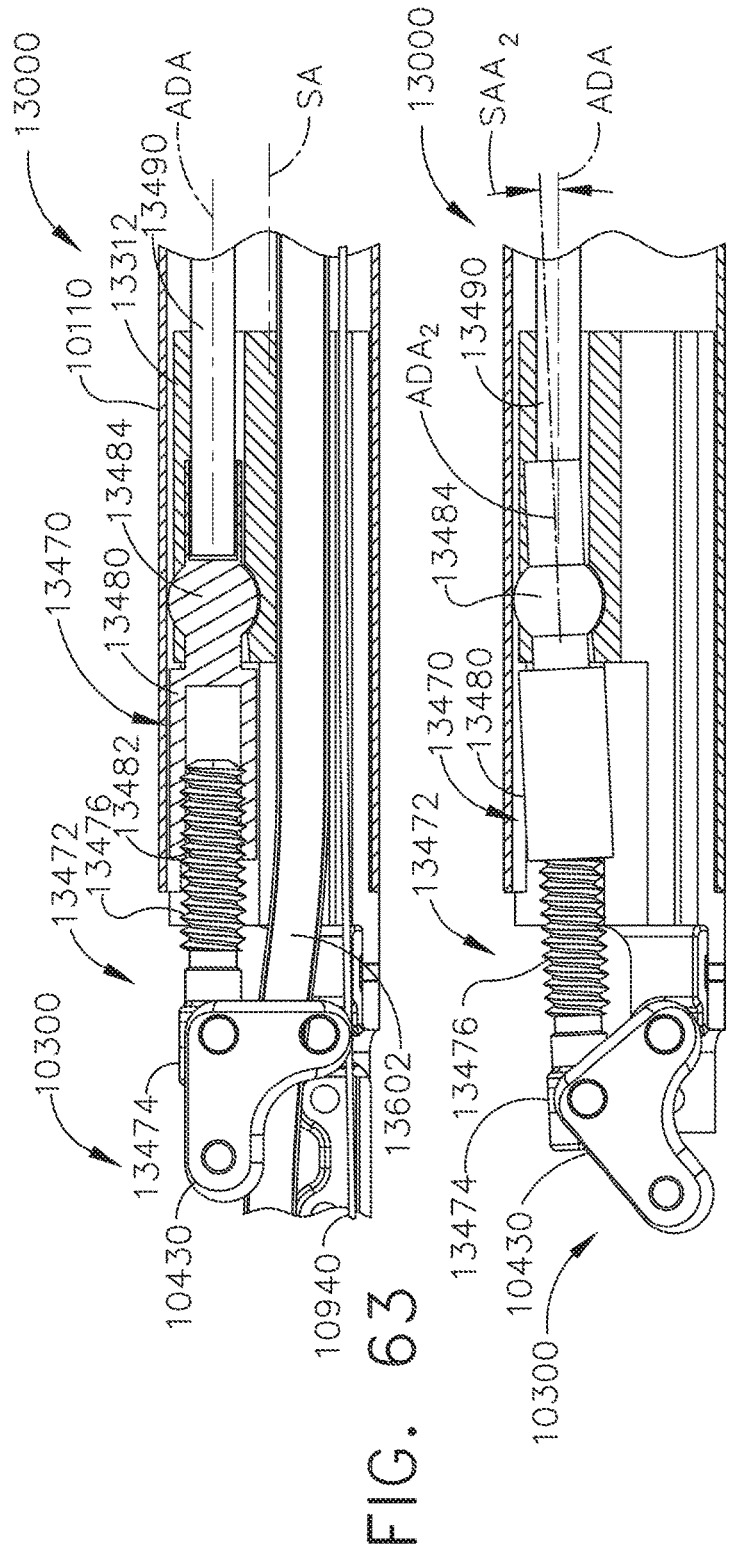
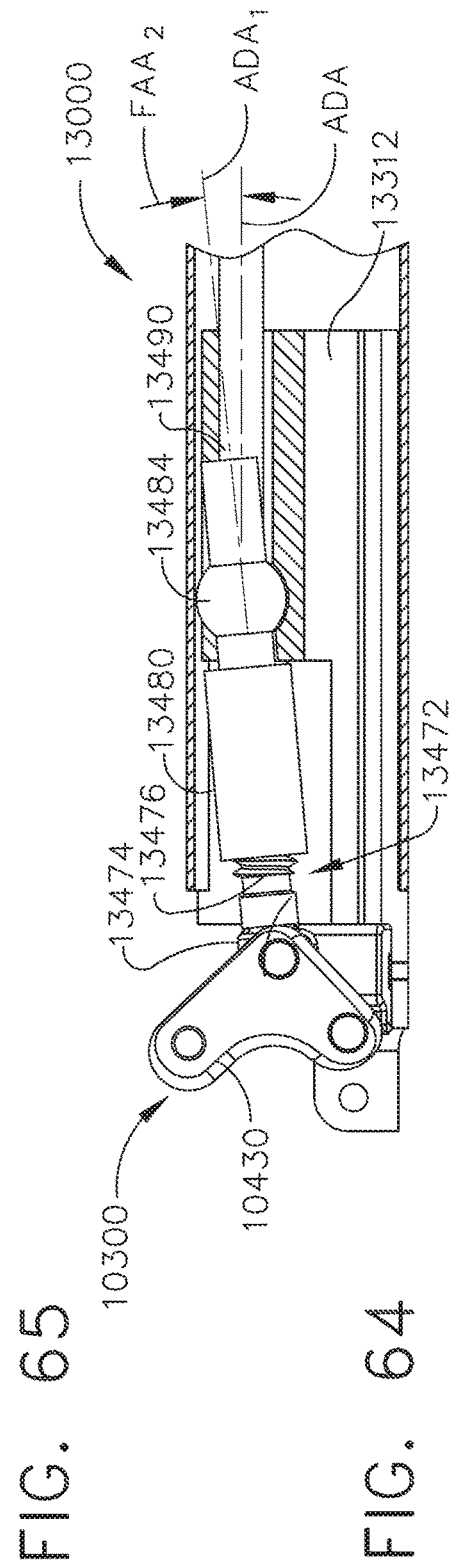
FIG. 63
FIG. 64
FIG. 65

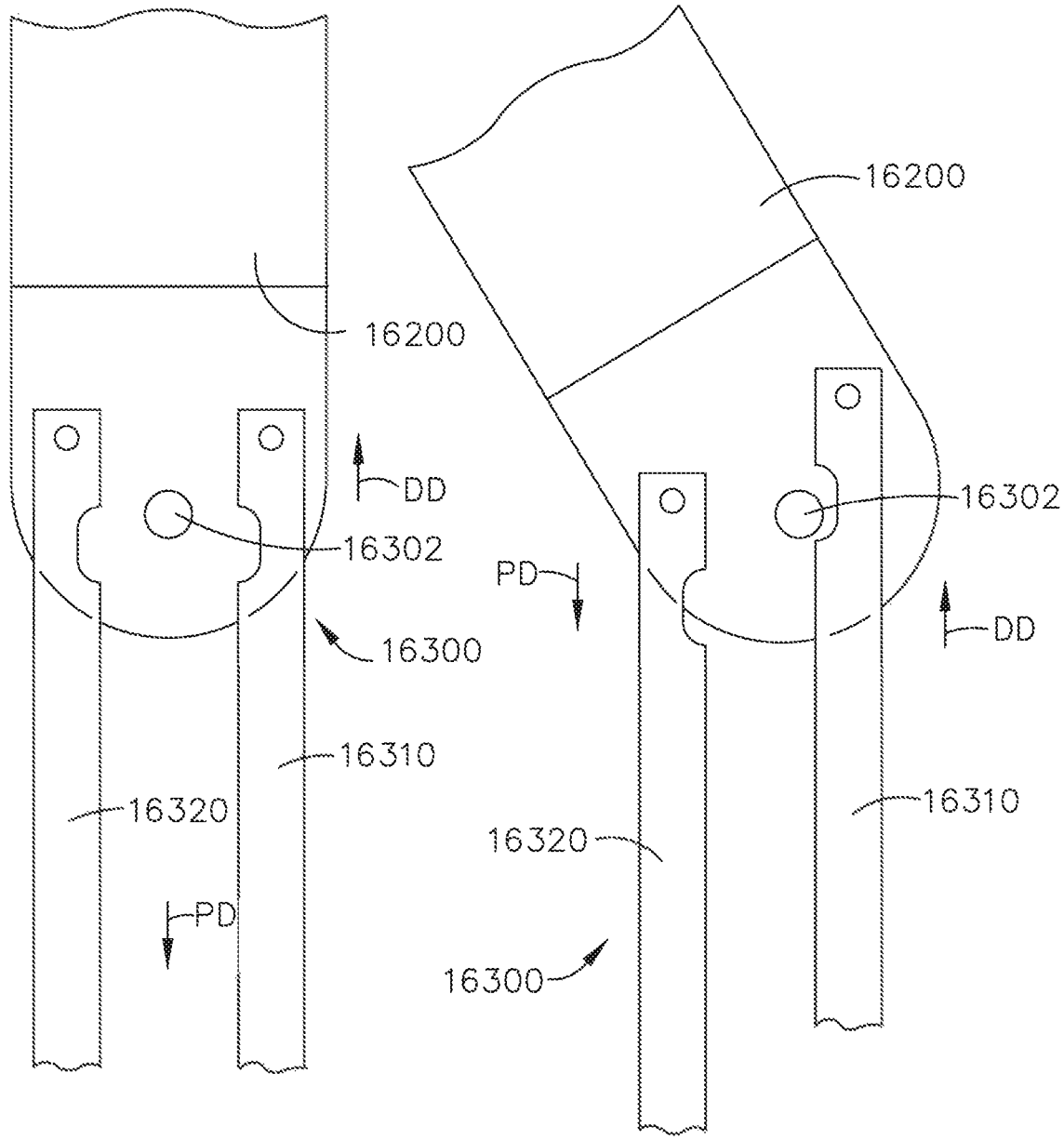

ARTICULATABLE SURGICAL INSTRUMENT

CROSS-REFERENCE TO RELATED APPLICATION

This non-provisional application claims the benefit under 35 U.S.C. § 119(e) of U.S. Provisional Patent Application Ser. No. 62/955,299, entitled DEVICES AND SYSTEMS FOR ELECTROSURGERY, filed Dec. 30, 2019, the disclosure of which is incorporated by reference herein in its entirety.

BACKGROUND

The present invention relates to surgical instruments designed to treat tissue, including but not limited to surgical instruments that are configured to cut and fasten tissue. The surgical instruments may include electrosurgical instruments powered by generators to effect tissue dissecting, cutting, and/or coagulation during surgical procedures. The surgical instruments may include instruments that are configured to cut and staple tissue using surgical staples and/or fasteners. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

SUMMARY

In various embodiments, a surgical instrument comprising a surgical end effector that comprises an end effector frame assembly is disclosed. A proximal shaft segment defines a shaft axis and is attached to the end effector frame assembly by an articulation system to facilitate articulation of the end effector frame assembly relative to the proximal shaft segment about an articulation axis that is transverse to the shaft axis. The articulation system comprises a first link that comprises a first link proximal end that is pivotally coupled to the proximal shaft segment. The first link further comprises a first link distal end. The articulation system further comprises a second link that comprises a second link proximal end that is pivotally coupled to the first link distal end. The second link further comprises a second link distal end that is pivotally coupled to the end effector frame assembly. The articulation system further comprises an axially movable articulation actuator that operably interfaces with the first link at a location between the first link proximal end and the first link distal end to apply articulation motions thereto.

In various embodiments, a surgical instrument comprising a surgical end effector that comprises an end effector frame assembly is disclosed. A first jaw is pivotally coupled to the end effector frame assembly. A second jaw is pivotally coupled to the first jaw. The first jaw and the second jaw are pivotally movable between an open position and a closed position upon application of axial control motions to the second jaw. The surgical instrument further comprises a proximal shaft segment that defines a shaft axis. The proximal shaft segment is attached to the end effector frame assembly by an articulation system to facilitate articulation of the end effector frame assembly relative to the proximal shaft segment about an articulation axis that is transverse to the shaft axis. The articulation system comprises a first link that comprises a first link proximal end that is pivotally coupled to the proximal shaft segment. The first link further comprises a first link distal end. The articulation system further comprises a second link that comprises a second link proximal end that is pivotally coupled to the first link distal end. The second link further comprises a second link distal end that is pivotally coupled to the end effector frame assembly. The articulation system further comprises an axially movable articulation actuator that operably interfaces with the first link at a location between the first link proximal end and the first link distal end to apply articulation motions thereto. The surgical instrument further comprises a drive member that extends between the right proximal link and the left proximal link. The drive member is coupled to the second jaw to apply the axial control motions thereto.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 34 is a top view of a portion of a distal frame member and a proximal housing member of a surgical instrument, in accordance with at least one aspect of the present disclosure;

FIG. 35 is a partial perspective view of a spring clip used to support the proximal housing member on the distal frame member of FIG. 34;

FIG. 63 is a cross-sectional side elevational view of the proximal shaft segment of FIG. 56 with an articulation joint thereof in an unarticulated position;

FIG. 64 is another cross-sectional side elevational view of the proximal shaft segment of FIG. 56 with the articulation joint thereof articulated in a first direction;

FIG. 65 is another cross-sectional side elevational view of the proximal shaft segment of FIG. 56 articulated in a second direction;

FIG. 89 is a partial view of another surgical instrument with a surgical end effector in an unarticulated position, in accordance with at least one aspect of the present disclosure;

FIG. 90 is another partial view of the surgical instrument of FIG. 89 with the surgical end effector thereof in an articulated position;

DETAILED DESCRIPTION

Figure 1:
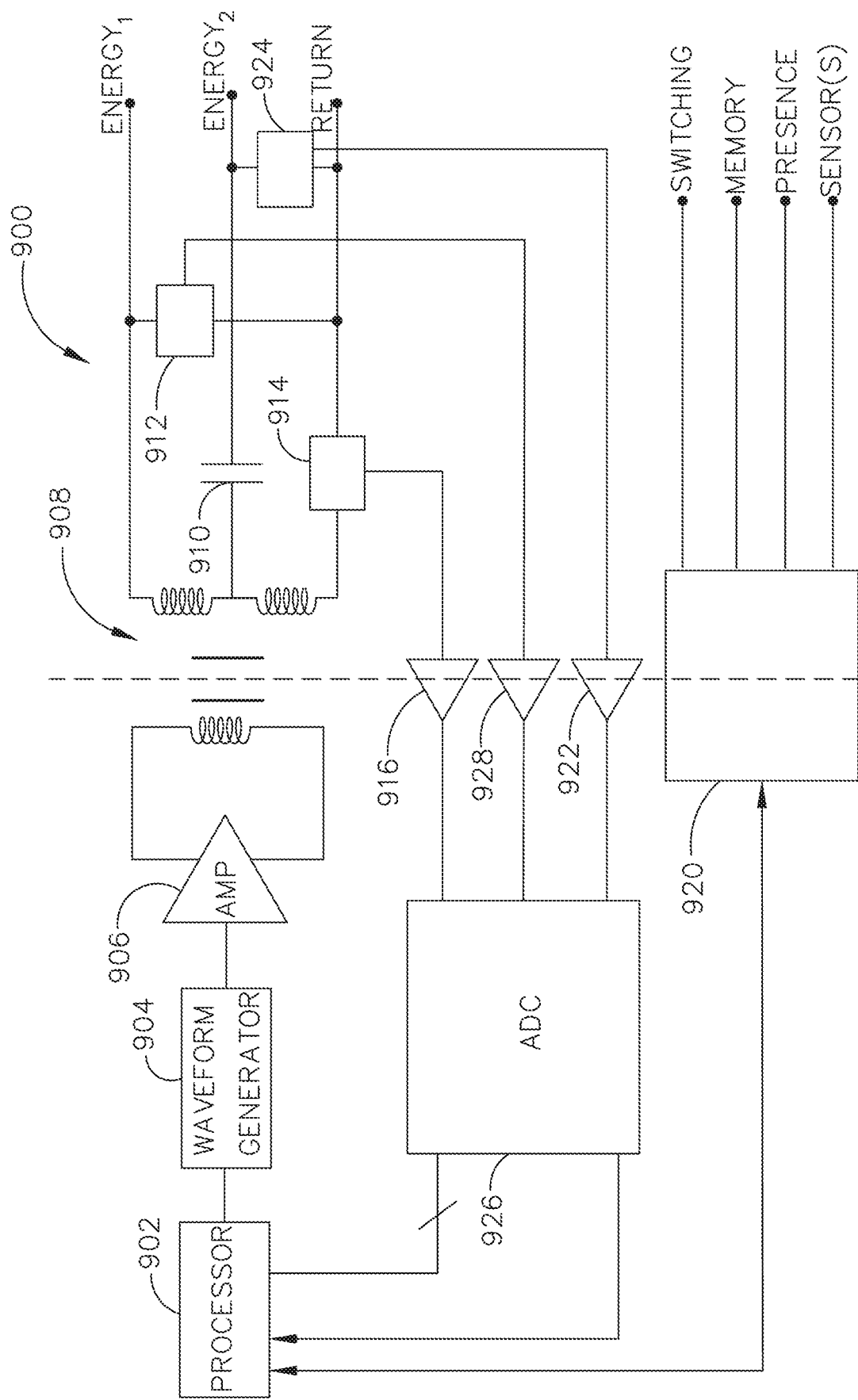
FIG. 1 illustrates an example of a generator for use with a surgical system, in accordance with at least one aspect of the present disclosure.

Applicant of the present application owns the following U.S. Patent Applications that were filed on May 28, 2020, the disclosure of each of which is herein incorporated by reference in its entirety:

U.S. patent application Ser. No. 16/885,813, entitled METHOD FOR AN ELECTROSURGICAL PROCEDURE, now U.S. Patent Application Publication No. 2021/0196354;

Ser. No. 16/885,823, entitled SURGICAL INSTRUMENT WITH JAW ALIGNMENT FEATURES, now U.S. Patent Application Publication No. 2021/0196355;

Ser. No. 16/885,826, entitled SURGICAL INSTRUMENT WITH ROTATABLE AND ARTICULATABLE SURGICAL END EFFECTOR, now U.S. Patent Application Publication No. 2021/0196356;

Ser. No. 16/885,838, entitled ELECTROSURGICAL INSTRUMENT WITH ASYNCHRONOUS ENERGIZING ELECTRODES, now U.S. Patent Application Publication No. 2021/0196357;

Ser. No. 16/885,851, entitled ELECTROSURGICAL INSTRUMENT WITH ELECTRODES BIASING SUPPORT, now U.S. Patent Application Publication No. 2021/0196358;

Ser. No. 16/885,860, entitled ELECTROSURGICAL INSTRUMENT WITH FLEXIBLE WIRING ASSEMBLIES, now U.S. Patent Application Publication No. 2021/0196349;

Ser. No. 16/885,866, entitled ELECTROSURGICAL INSTRUMENT WITH VARIABLE CONTROL MECHANISMS, now U.S. Patent Application Publication No. 2021/0196350;

Ser. No. 16/885,870, entitled ELECTROSURGICAL SYSTEMS WITH INTEGRATED AND EXTERNAL POWER SOURCES, now U.S. Patent Application Publication No. 2021/0196343;

Ser. No. 16/885,873, entitled ELECTROSURGICAL INSTRUMENTS WITH ELECTRODES HAVING ENERGY FOCUSING FEATURES, now U.S. Patent Application Publication No. 2021/0196359;

Ser. No. 16/885,879, entitled ELECTROSURGICAL INSTRUMENTS WITH ELECTRODES HAVING VARIABLE ENERGY DENSITIES, now U.S. Pat. No. 11,589,916;

Ser. No. 16/885,881, entitled ELECTROSURGICAL INSTRUMENT WITH MONOPOLAR AND BIPOLAR ENERGY CAPABILITIES, now U.S. Patent Application Publication No. 2021/0196361;

Ser. No. 16/885,888, entitled ELECTROSURGICAL END EFFECTORS WITH THERMALLY INSULATIVE AND THERMALLY CONDUCTIVE PORTIONS, now U.S. Patent Application Publication No. 2021/0196362;

Ser. No. 16/885,893, entitled ELECTROSURGICAL INSTRUMENT WITH ELECTRODES OPERABLE IN BIPOLAR AND MONOPOLAR MODES, now U.S. Patent Application Publication No. 2021/0196363;

Ser. No. 16/885,900, entitled ELECTROSURGICAL INSTRUMENT FOR DELIVERING BLENDED ENERGY MODALITIES TO TISSUE, now U.S. Patent Application Publication No. 2021/0196364;

Ser. No. 16/885,917, entitled CONTROL PROGRAM ADAPTATION BASED ON DEVICE STATUS AND USER INPUT, now U.S. Patent Application Publication No. 2021/0196365;

Ser. No. 16/885,923, entitled CONTROL PROGRAM FOR MODULAR COMBINATION ENERGY DEVICE, now U.S. Patent Application Publication No. 2021/0196366; and Ser. No. 16/885,931, entitled SURGICAL SYSTEM COMMUNICATION PATHWAYS, now U.S. Patent Application Publication No. 2021/0196344.

Applicant of the present application owns the following U.S. Provisional Patent Applications that were filed on Dec. 30, 2019, the disclosure of each of which is herein incorporated by reference in its entirety:

U.S. Provisional Patent Application Ser. No. 62/955,294, entitled USER INTERFACE FOR SURGICAL INSTRUMENT WITH COMBINATION ENERGY MODALITY END-EFFECTOR;

U.S. Provisional Patent Application Ser. No. 62/955,292, entitled COMBINATION ENERGY MODALITY END-EFFECTOR; and U.S. Provisional Patent Application Ser. No. 62/955,306, entitled SURGICAL INSTRUMENT SYSTEMS.

Applicant of the present application owns the following U.S. Patent Applications, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

U.S. patent application Ser. No. 16/562,123, titled METHOD FOR CONSTRUCTING AND USING A MODULAR SURGICAL ENERGY SYSTEM WITH MULTIPLE DEVICES;

U.S. patent application Ser. No. 16/562,135, titled METHOD FOR CONTROLLING AN ENERGY MODULE OUTPUT;

U.S. patent application Ser. No. 16/562,144, titled METHOD FOR CONTROLLING A MODULAR ENERGY SYSTEM USER INTERFACE; and U.S. patent application Ser. No. 16/562,125, titled METHOD FOR COMMUNICATING BETWEEN MODULES AND DEVICES IN A MODULAR SURGICAL SYSTEM.

Before explaining various aspects of an electrosurgical system in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Various aspects are directed to electrosurgical systems that include electrosurgical instruments powered by generators to effect tissue dissecting, cutting, and/or coagulation during surgical procedures. The electrosurgical instruments may be configured for use in open surgical procedures, but has applications in other types of surgery, such as laparoscopic, endoscopic, and robotic-assisted procedures.

As described below in greater detail, an electrosurgical instrument generally includes a shaft having a distally-mounted end effector (e.g., one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example.

FIG. 1 illustrates an example of a generator 900 configured to deliver multiple energy modalities to a surgical instrument. The generator 900 provides RF and/or ultrasonic signals for delivering energy to a surgical instrument. The generator 900 comprises at least one generator output that can deliver multiple energy modalities (e.g., ultrasonic, bipolar or monopolar RF, irreversible and/or reversible electroporation, and/or microwave energy, among others) through a single port, and these signals can be delivered separately or simultaneously to an end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 906 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY$_1$ and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 928, 922 and the output of the current sensing circuit 914 is provided to another isolation transformer 916. The outputs of the isolation transformers 916, 928, 922 on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 928, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be RF monopolar energy and the second energy modality ENERGY$_2$ may be RF bipolar energy. Nevertheless, in addition to bipolar and monopolar RF energy modalities, other energy modalities include ultrasonic energy, irreversible and/or reversible electroporation and/or microwave energy, among others. Also, although the example illustrated in FIG. 1 shows a single return path RETURN may be provided for two or more energy modalities, in other aspects, multiple return paths RETURN$_n$ may be provided for each energy modality ENERGY$_n$.

As shown in FIG. 1, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. In one example, a connection of RF bipolar electrodes to the generator 900 output would be preferably located between the output labeled ENERGY$_2$ and RETURN. In the case of monopolar output, the preferred connections would be active electrode (e.g., pencil or other probe) to the ENERGY$_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Figure 2:
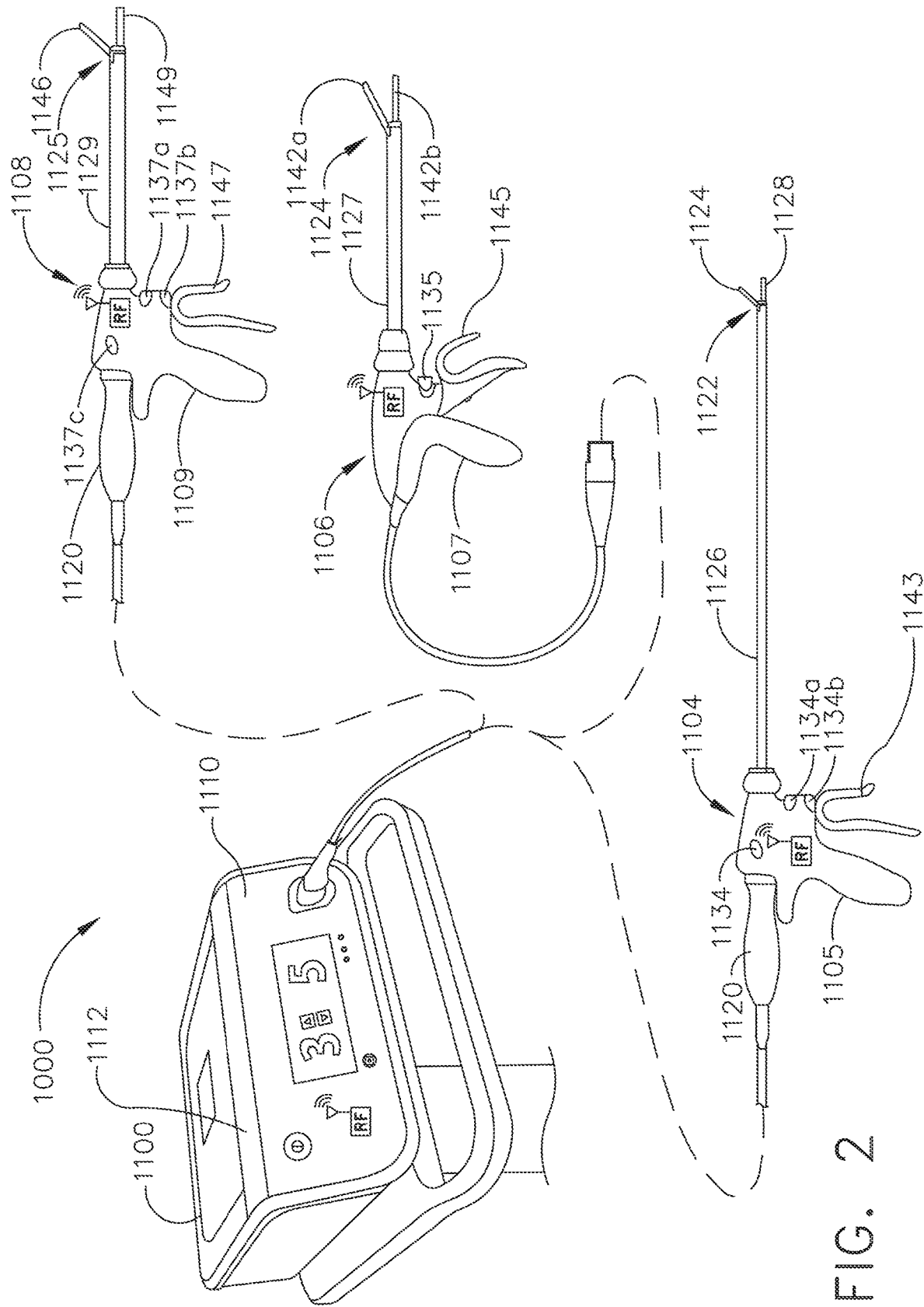
FIG. 2 illustrates one form of a surgical system comprising a generator and an electrosurgical instrument usable therewith, in accordance with at least one aspect of the present disclosure.

FIG. 2 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 2 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1137, 1134b, 1134c to energize and drive the ultrasonic blade 1128 or other function. The toggle buttons 1137, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1145, 1142b and return through an electrical conductor portion of the shaft 1127. The electrodes are coupled to and energized by a bipolar energy source within the generator 1100. The handpiece 1107 comprises a trigger 1145 to operate the clamp arms 1145, 1142b and an energy button 1135 to actuate an energy switch to energize the electrodes in the end effector 1124. The second surgical instrument 1106 can also be used with a return pad to deliver monopolar energy to tissue.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 11310, 1137b, 1137c to energize and drive the ultrasonic blade 1149 or other function. The toggle buttons 11310, 1137b, 1137c can be configured to energize the ultrasonic transducer 1120 with the generator 1100 and energize the ultrasonic blade 1149 with a bipolar energy source also contained within the generator 1100. Monopolar energy can be delivered to the tissue in combination with, or separately from, the bipolar energy.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 2, the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent application publication US-2017-0086914-A1, which is herein incorporated by reference in its entirety.

Figure 3:
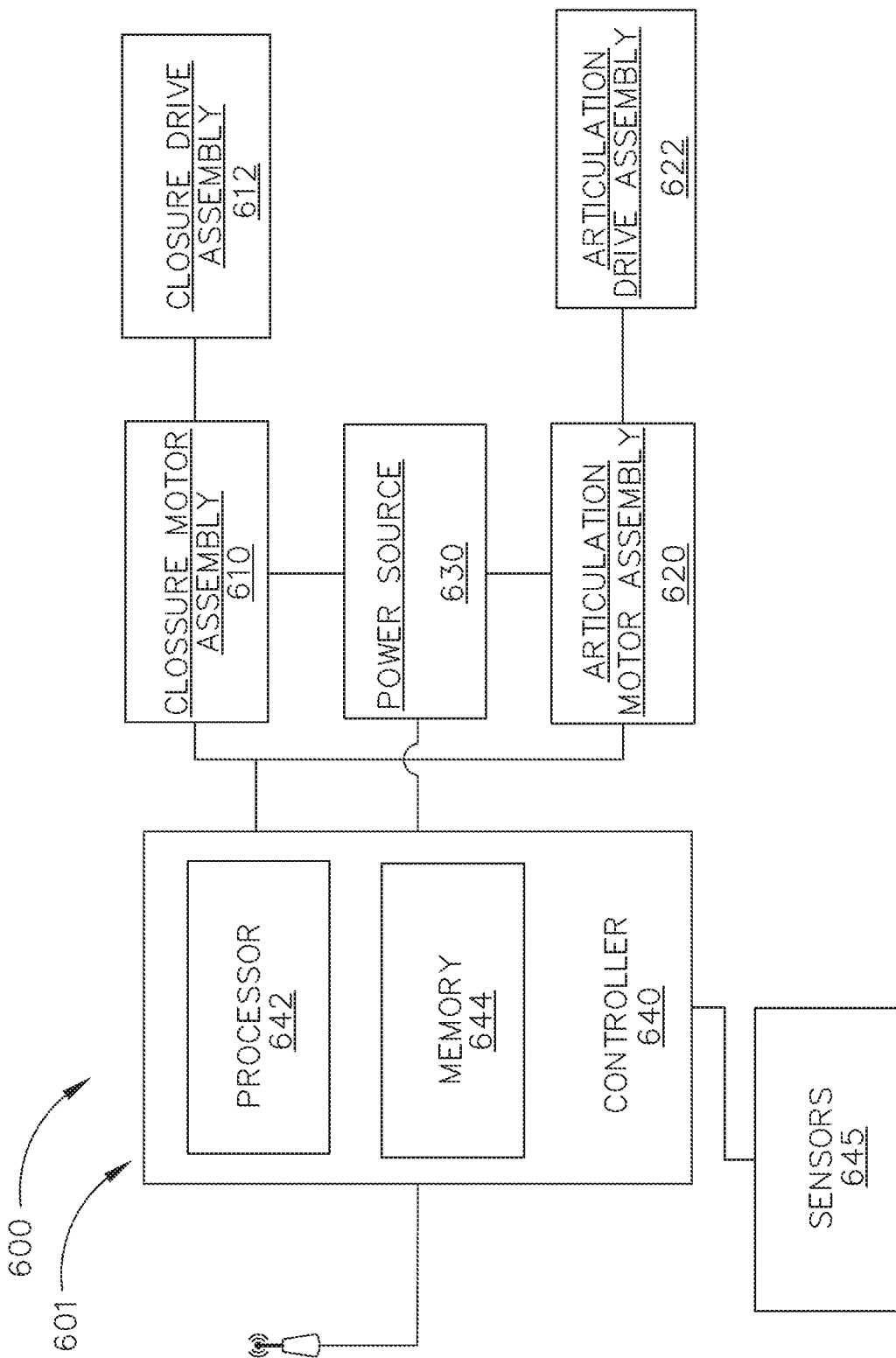
FIG. 3 illustrates a schematic diagram of a surgical instrument or tool, in accordance with at least one aspect of the present disclosure.

FIG. 3 illustrates a schematic diagram of a surgical instrument or tool 600 comprising a plurality of motor assemblies that can be activated to perform various functions. In the illustrated example, a closure motor assembly 610 is operable to transition an end effector between an open configuration and a closed configuration, and an articulation motor assembly 620 is operable to articulate the end effector relative to a shaft assembly. In certain instances, the plurality of motors assemblies can be individually activated to cause firing, closure, and/or articulation motions in the end effector. The firing, closure, and/or articulation motions can be transmitted to the end effector through a shaft assembly, for example.

In certain instances, the closure motor assembly 610 includes a closure motor. The closure 603 may be operably coupled to a closure motor drive assembly 612 which can be configured to transmit closure motions, generated by the motor to the end effector, in particular to displace a closure member to close to transition the end effector to the closed configuration. The closure motions may cause the end effector to transition from an open configuration to a closed configuration to capture tissue, for example. The end effector may be transitioned to an open position by reversing the direction of the motor.

In certain instances, the articulation motor assembly 620 includes an articulation motor that be operably coupled to an articulation drive assembly 622 which can be configured to transmit articulation motions, generated by the motor to the end effector. In certain instances, the articulation motions may cause the end effector to articulate relative to the shaft, for example.

One or more of the motors of the surgical instrument 600 may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, the motor assemblies 610, 620 include one or more motor drivers that may comprise one or more H-Bridge FETs. The motor drivers may modulate the power transmitted from a power source 630 to a motor based on input from a microcontroller 640 (the "controller"), for example, of a control circuit 601. In certain instances, the microcontroller 640 can be employed to determine the current drawn by the motor, for example.

In certain instances, the microcontroller 640 may include a microprocessor 642 (the "processor") and one or more non-transitory computer-readable mediums or memory units 644 (the "memory"). In certain instances, the memory 644 may store various program instructions, which when executed may cause the processor 642 to perform a plurality of functions and/or calculations described herein. In certain instances, one or more of the memory units 644 may be coupled to the processor 642, for example. In various aspects, the microcontroller 640 may communicate over a wired or wireless channel, or combinations thereof.

In certain instances, the power source 630 can be employed to supply power to the microcontroller 640, for example. In certain instances, the power source 630 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 630. In certain instances, the power source 630 may be replaceable and/or rechargeable, for example.

In various instances, the processor 642 may control a motor driver to control the position, direction of rotation, and/or velocity of a motor of the assemblies 610, 620. In certain instances, the processor 642 can signal the motor driver to stop and/or disable the motor. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 642 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 642 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the surgical instrument 600. Accordingly, the present disclosure should not be limited in this context.

In certain instances, the memory 644 may include program instructions for controlling each of the motors of the surgical instrument 600. For example, the memory 644 may include program instructions for controlling the closure motor and the articulation motor. Such program instructions may cause the processor 642 to control the closure and articulation functions in accordance with inputs from algorithms or control programs of the surgical instrument 600.

In certain instances, one or more mechanisms and/or sensors such as, for example, sensors 645 can be employed to alert the processor 642 to the program instructions that should be used in a particular setting. For example, the sensors 645 may alert the processor 642 to use the program instructions associated with closing and articulating the end effector. In certain instances, the sensors 645 may comprise position sensors which can be employed to sense the position of a closure actuator, for example. Accordingly, the processor 642 may use the program instructions associated with closing the end effector to activate the motor of the closure drive assembly 620 if the processor 642 receives a signal from the sensors 630 indicative of actuation of the closure actuator.

In some examples, the motors may be brushless DC electric motors, and the respective motor drive signals may comprise a PWM signal provided to one or more stator windings of the motors. Also, in some examples, the motor drivers may be omitted and the control circuit 601 may generate the motor drive signals directly.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that position during the actuation of the end effector and completion of the surgical procedure. Such articulation joint arrangements must also be able to withstand external forces that are experienced by the end effector during use.

Figure 4:
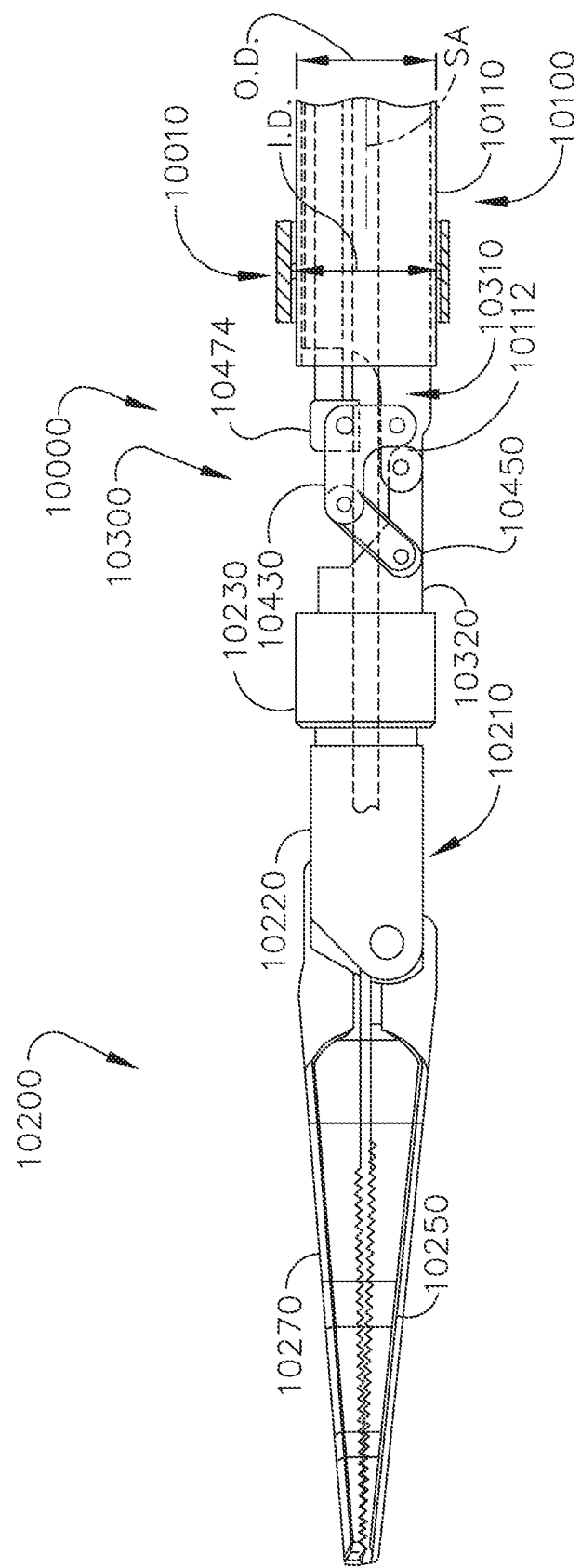
FIG. 4 is a side elevational view of a portion of a surgical instrument in an unarticulated position, in accordance with at least one aspect of the present disclosure.

FIG. 4 illustrates a portion of a surgical instrument 10000 that may address many, if not all, of the aforementioned challenges. As can be seen in FIG. 4, the surgical instrument 10000 includes a proximal shaft segment 10100 that may be operably coupled to a housing (not shown) that may support one or more control motors and control systems for controlling the operation and actuation of a surgical end effector 10200 that is operably coupled to the proximal shaft segment 10100. For example, the housing may comprise a handheld housing of various types disclosed herein or the housing may comprise a portion of an automated system or robotically-controlled system that is used to manipulate and operate the surgical end effector 10200 that is operably coupled to the proximal shaft segment 10100. The handheld housing may comprise trigger(s) and or switches for controlling motors and/or mechanical systems configured to generate control motions and actions.

In the illustrated example, the proximal shaft segment 10100 defines a shaft axis SA that extends centrally through the proximal shaft segment 10100 and the surgical end effector 10200 for reference purposes. The proximal shaft segment 10100 comprises a proximal outer shaft tube 10110 that may extend from the housing or otherwise interface therewith. The proximal outer shaft tube 10110 is hollow or is at least partially hollow to accommodate various drive members and components employed to convey control motions and signals between control systems in the housing and the surgical end effector 10200. In at least one arrangement, the proximal outer shaft tube 10110 is rigid or at least partially rigid and defines a maximum outer diameter "O.D.". Other arrangements are contemplated wherein the proximal outer shaft tube 10110 is flexible or at least partially flexible or selectively contourable.

Figure 5:
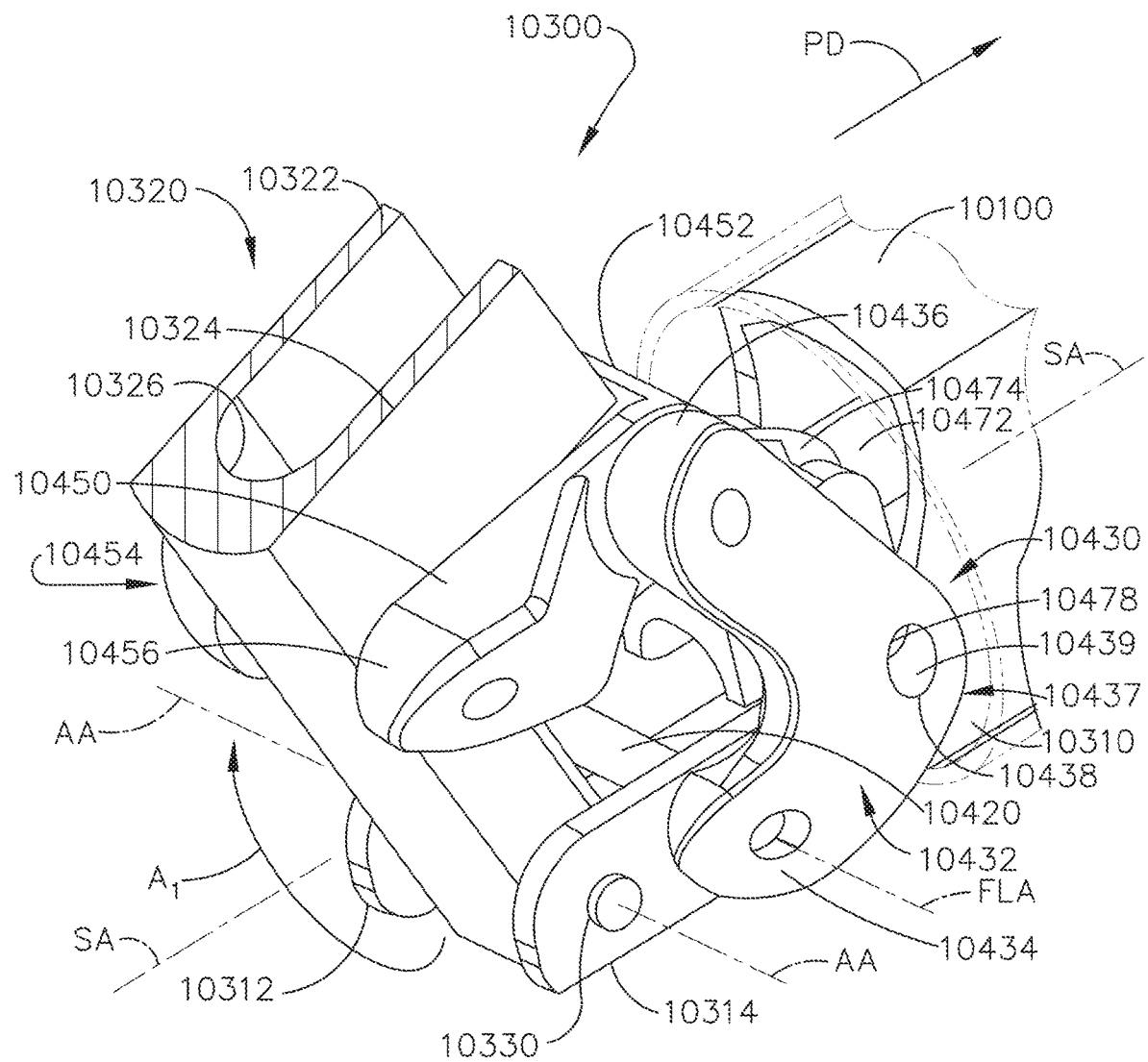
FIG. 5 is a perspective view of a portion of an articulation joint of the surgical instrument of FIG. 4 articulated in a first direction.

FIG. 4 illustrates portions of a trocar cannula 10010 that has an inner diameter "I.D." that is greater than the O.D. of the proximal outer shaft tube 10110. For example, the inner diameter I.D. may be at least 1 mm larger than the O.D. of the proximal outer shaft tube 10110 to facilitate passage of the proximal outer shaft tube 10110 therethrough. As can be seen in FIG. 4, the proximal shaft segment 10100 is attached to a surgical end effector frame assembly 10210 by an articulation joint generally designated as 10300. In the illustrated arrangement, the articulation joint 10300 comprises a proximal shaft frame member 10310 that extends distally out of a distal end 10102 of the proximal shaft segment 10100. The proximal shaft frame member 10310 may be attached to the proximal outer shaft tube 10110 by, for example, welding, adhesive, etc. As can be seen in FIG. 5, the proximal shaft frame member 10310 comprises a U-shaped cradle portion that includes proximally extending attachment arms 10312, 10314, wherein attachment arm 10312 is located on one side of the shaft axis SA and the attachment arm 10314 is located on an opposite side of the shaft axis SA.

Figure 13:
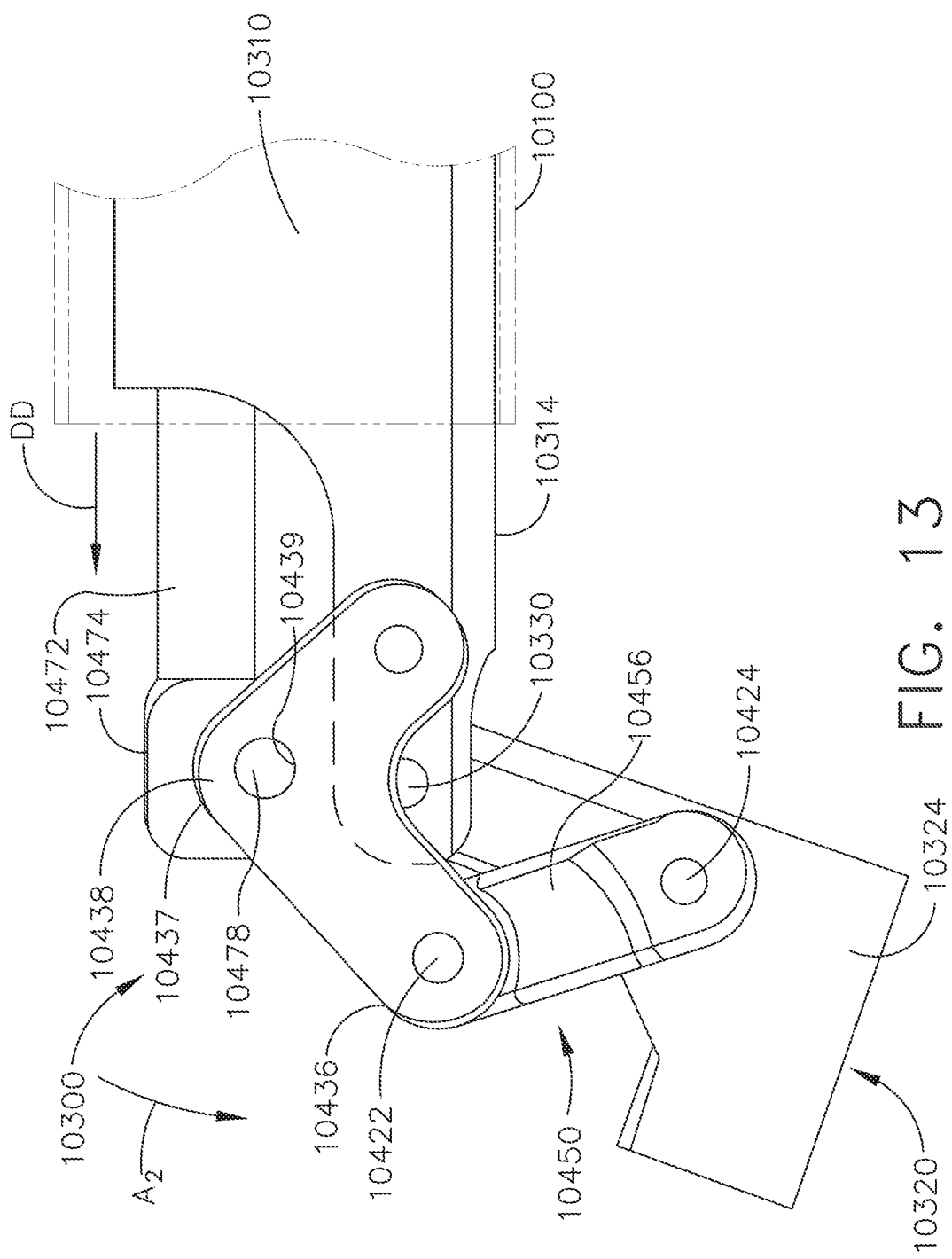
FIG. 13 is a side elevational view of the articulation joint of the surgical instrument of FIG. 4 articulated in a second direction.
Figure 15:
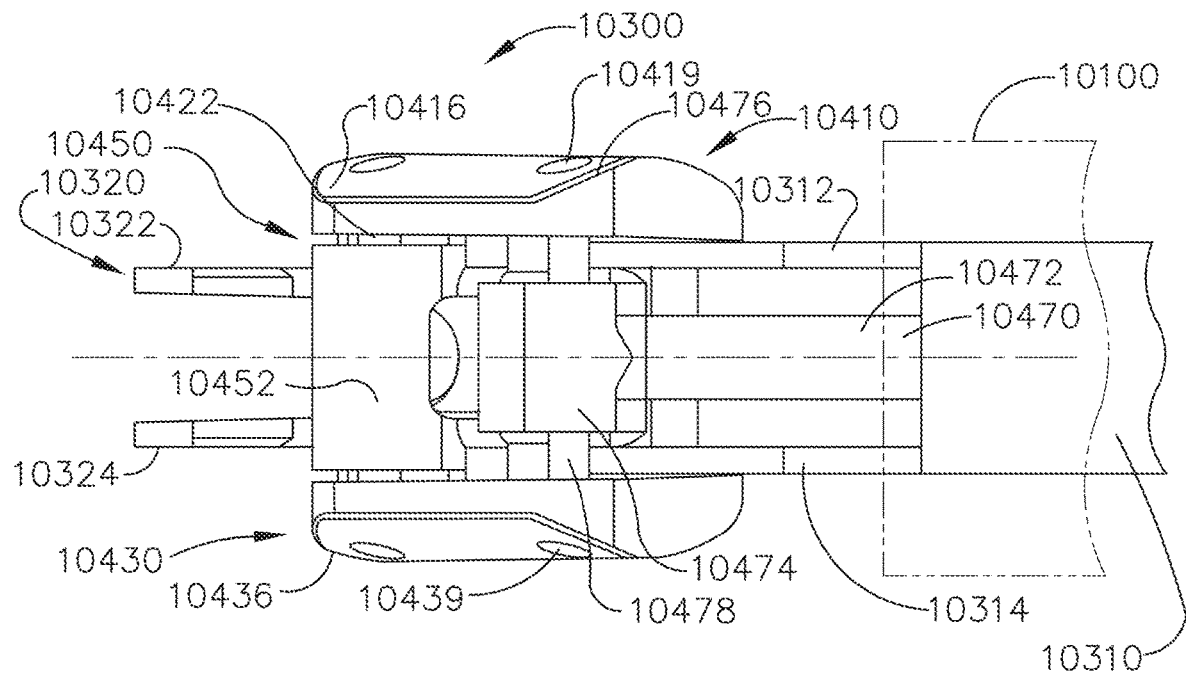
FIG. 15 is a top view of the articulation joint of FIG. 13.
Figure 14:
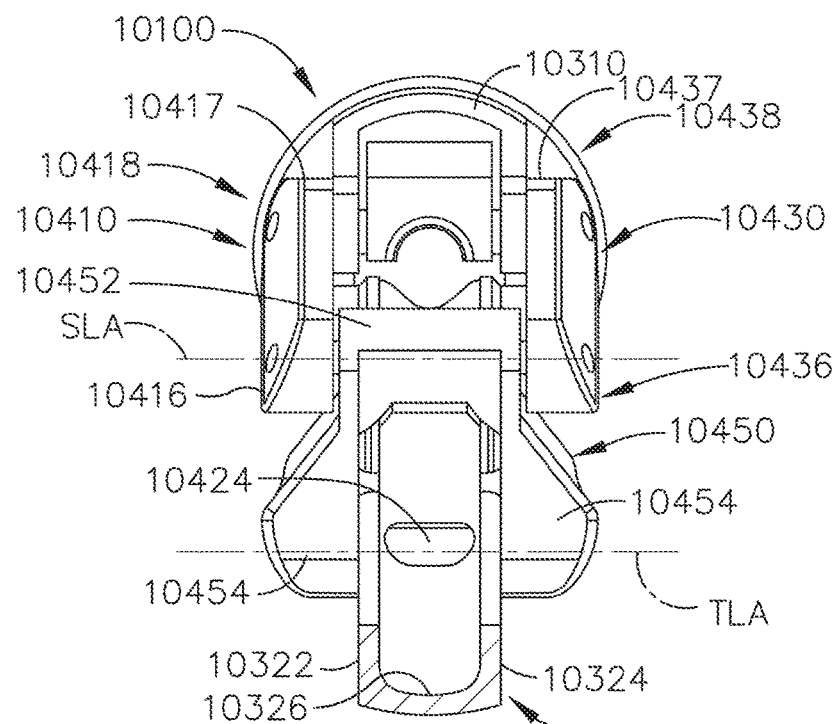
FIG. 14 is an end elevational view of the articulation joint of FIG. 13.

In certain instances, the articulation joint 10300 further comprises a proximal end effector frame member 10320 that also comprises a portion of the end effector frame assembly 10210. The proximal end effector frame member 10320 comprises two upstanding support sides 10322, 10324 that define a U-shaped cradle 10326. The proximal end effector frame member 10320 is received between the attachment arms 10312, 10314 and is pivotally supported therein by an articulation pin 10330 that defines an articulation axis AA. The articulation joint 10300 facilitates selective articulation of the proximal end effector frame member 10320 through ranges of articulation on each side of the shaft axis SA. For example, the articulation joint 10300 facilitates articulation of the proximal end effector frame member 10320 from an unarticulated position (FIGS. 6-9) to a first maximum articulated position in a first articulation direction $A_1$ on one side of the shaft axis SA (FIG. 5 and FIGS. 10-12) as well as to a second maximum articulated position in a second articulation direction $A_2$ (FIGS. 13-15).

In various instances, the surgical end effector 10200 is selectively articulated about the articulation axis AA relative to the proximal shaft segment 10100 by an articulation system generally designated as 10400. In one example, the articulation system 10400 comprises a right proximal link 10410 located on a right side of the shaft axis, a left proximal link 10430 located on a left side of the shaft axis and a centrally disposed second link 10450. See FIG. 6. The right proximal link 10410 comprises a right proximal link body 10412 that is roughly L-shaped and comprises a right proximal link proximal end 10414 and a right proximal link distal end 10416. Similarly, the left proximal link 10430 comprises a left proximal link body 10432 that is roughly L-shaped and comprises a left proximal link proximal end 10434 and a left proximal link distal end 10436. In the illustrated example, the right proximal link proximal end 10414 is pivotally supported relative to the attachment arm 10312 and the left proximal link proximal end 10434 is pivotally supported relative to the attachment arm 10314. The right proximal link proximal end 10414 is pivotally coupled to the attachment arm 10312 and the left proximal link proximal end 10434 is pivotally coupled to the attachment arm 10314 by a first link pin 10420. The first link pin 10420 defines a first link axis FLA that is transverse to the shaft axis SA and facilitates pivotal travel of the right proximal link 10410 and the left proximal link 10430 about the first link axis FLA relative to the proximal shaft frame member 10310. See FIGS. 5 and 11.

Figure 6:
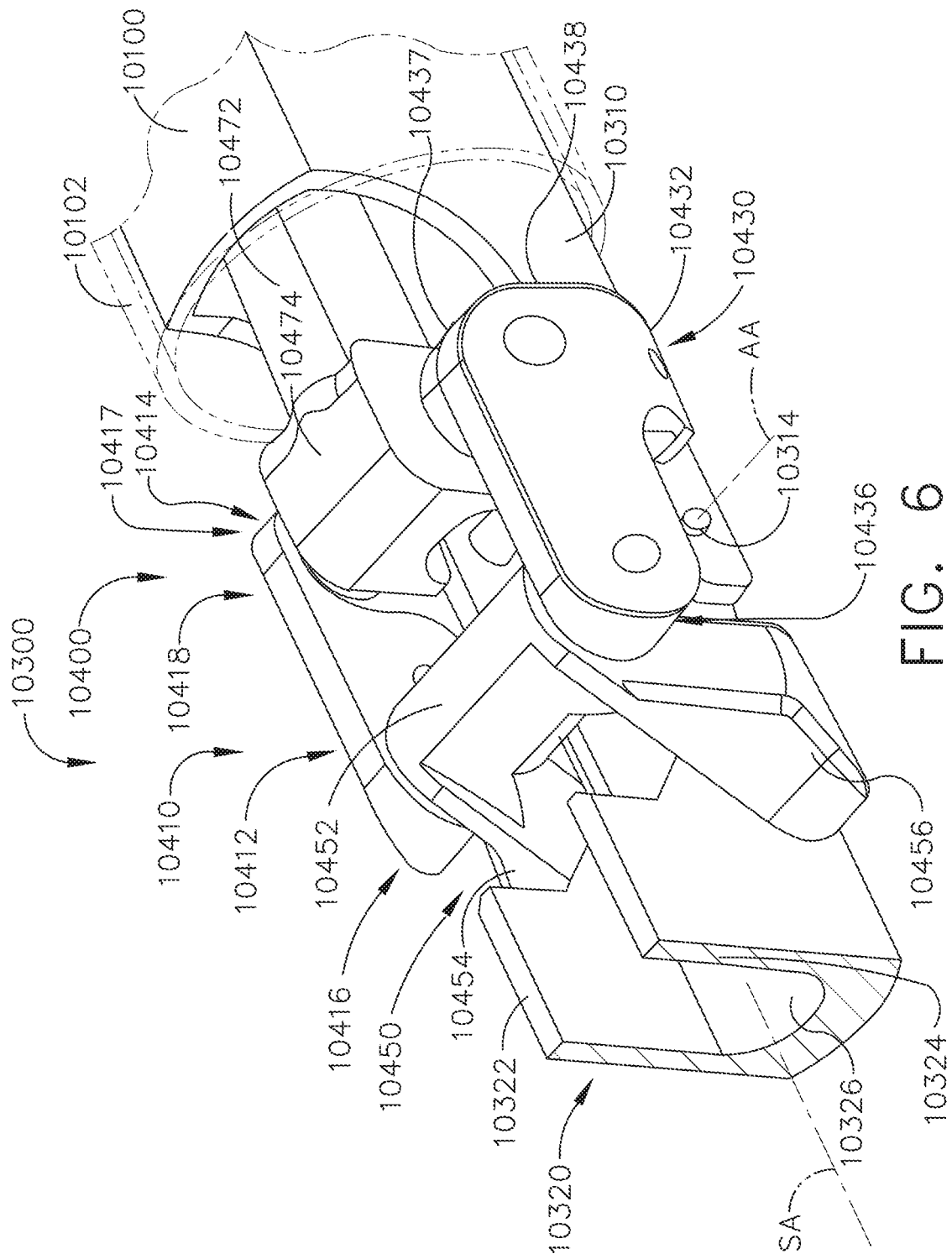
FIG. 6 is another perspective view of the articulation joint of FIG. 5 in an unarticulated position.
Figure 7:
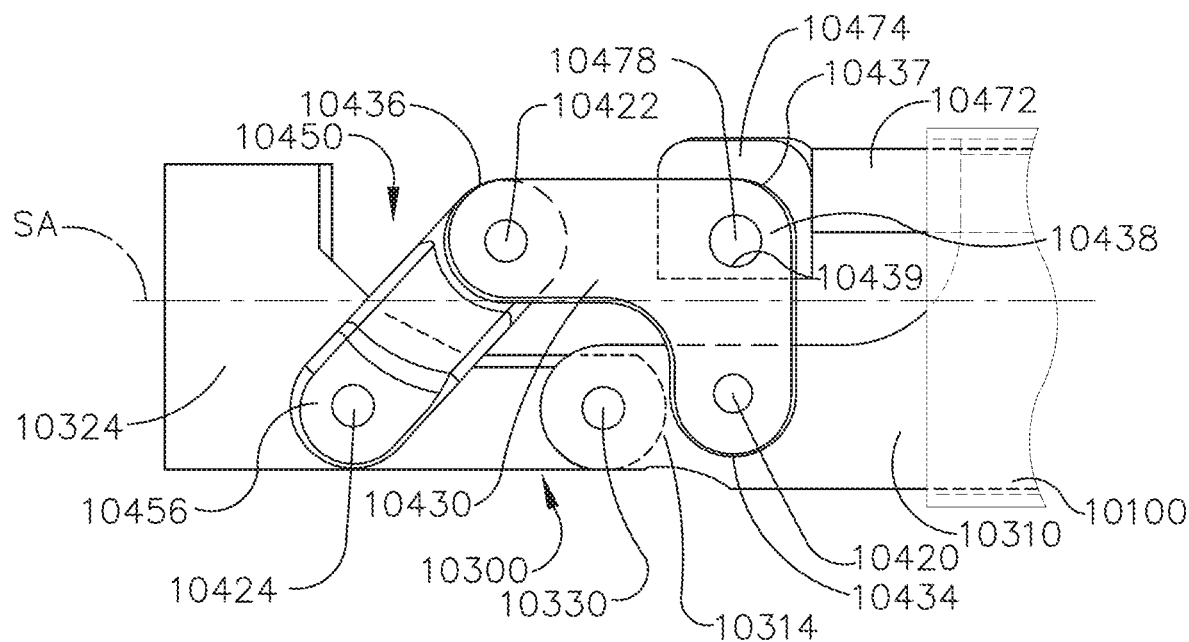
FIG. 7 is a side elevational view of the articulation joint of FIG. 6.

Turning to FIG. 6, in certain instances, the second link 10450 is substantially U-shaped and comprises a second link proximal end 10452 that is received between the right proximal link distal end 10416 and the left proximal link distal end 10436 and spans the distance therebetween. The second link proximal end 10452 is pivotally coupled to the right proximal link distal end 10416 and the left proximal link distal end 10436 by a second link pin 10422. See FIG. 7. The second link pin 10422 defines a second link axis SLA that is transverse to the shaft axis SA and facilitates relative pivotal travel of the second link 10450 relative to the right proximal link 10410 and the left proximal link 10430 about the second link axis SLA. The second link 10450 further comprises a right second link arm 10454 and a left second link arm 10456 that each extend distally from the second link proximal end 10452. The right second link arm 10454 and the left second link arm 10456 are pivotally attached to the proximal end effector frame member 10320 by a third link pin 10424. The third link pin 10424 defines a third link axis TLA that is transverse to the shaft axis SA and facilitates pivotal travel of the second link 10450 relative to the proximal end effector frame member 10320 about the third link axis TLA. See FIGS. 7 and 9.

The articulation system 10400 further comprises an axially movable articulation actuator 10470 that is configured to apply axial articulation motions to the right proximal link 10410 and the left proximal link 10430. In various instances, the articulation actuator may be axially aligned with the shaft axis SA. In the illustrated arrangement, the articulation actuator 10470 comprises an articulation shaft 10472 that includes a distal end formation 10474 that is pivotally coupled to the right proximal link 10410 and the left proximal link 10430. For example, the distal end formation 10474 comprises a right protruding right link pin 10476 that is configured to pivotally extend into a right pivot hole 10419 that is provided in a right first pivot location 10418 through a right first corner portion 10417 of the right proximal link 10410. See FIG. 9. Stated another way, the right link pin 10476 pivotally engages the right proximal link 10410 at a right first pivot location 10418 that is between the right proximal link proximal end 10414 and the right proximal link distal end 10416 of the right proximal link 10410. Likewise, the distal end formation 10474 comprises a left protruding left link pin 10478 that is configured to pivotally extend into a left pivot hole 10439 that is provided in a left first pivot location 10438 that is through a left first corner portion 10437 of the left proximal link 10430. Stated another way, the left link pin 10478 pivotally engages the left proximal link 10430 at a left first pivot location 10438 that is located between the left proximal link proximal end 10434 and the left proximal link distal end 10436 of the left proximal link 10430.

The surgical end effector 10200 may be selectively articulated about the articulation axis AA by moving the articulation actuator 10470 in a proximal direction PD or a distal direction DD. For example, to articulate the surgical end effector 10200 in the first articulation direction $A_1$, the articulation actuator 10470 is axially moved in a proximal direction PD. See FIG. 5 and FIGS. 10-12. To articulate the surgical end effector 10200 in the second articulation direction $A_2$, the articulation actuator 10470 is axially moved in a distal direction DD. See FIGS. 13-15. The articulation actuator 10470 extends through the proximal shaft segment 10100 to operably interface with an articulation drive system supported in the housing.

Figure 16:
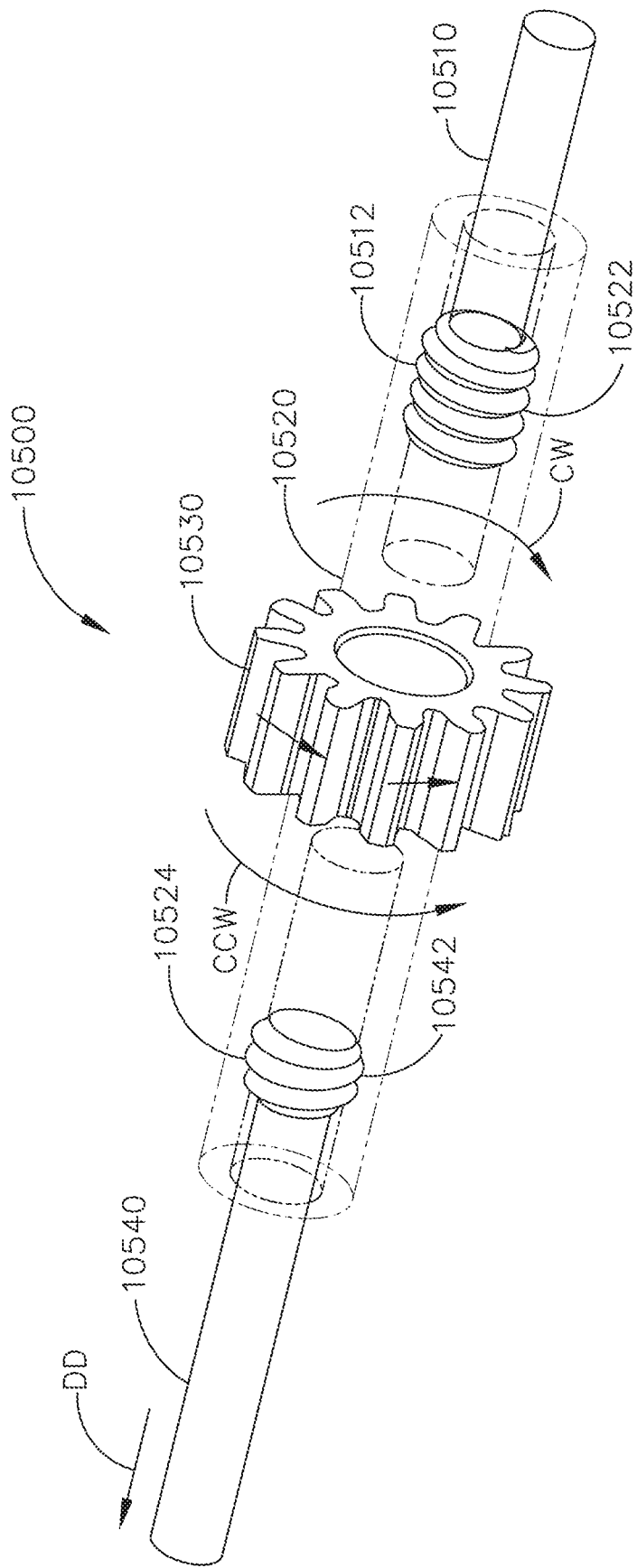
FIG. 16 is a perspective view of a portion of an axial drive system embodiment, in accordance with at least one aspect of the present disclosure.

A variety of axial drive system arrangements are known. FIG. 16 illustrates a portion of an axial drive system 10500 that may be employed (in or on the housing) to apply axial drive motions to the articulation actuator 10470, for example. In certain instances, as can be seen in FIG. 16, the axial drive system 10500 comprises a fixed proximal shaft 10510 that includes a left handed threaded segment 10512 that is supported in a drive shaft 10520 (shown in phantom lines). The threaded segment 10512 is in threaded engagement with a corresponding segment of threads 10522 in the drive shaft 10520. The drive shaft 10520 is supported for rotational travel by a drive gear 10530 that is journaled thereon. In various instances, the drive gear 10530 may meshingly interface with a motor driven gear (not shown) that is supported in or on the housing. In one embodiment, the axial drive system 10500 further includes a distal shaft 10540 that includes a right handed thread segment 10542 that is supported in a distal portion of the drive shaft 10520. The threaded segment 10542 is in threaded engagement with a corresponding segment of threads 10524 in the drive shaft 10520. In the illustrated arrangement, for example, one rotation of the drive gear 10530 in a counterclockwise CCW direction may result in 0.050 inches of linear travel of the distal shaft 10540 in the distal direction. Likewise, rotation of the drive gear 10530 in a clockwise direction CW will cause the distal shaft 10540 to linearly move in a distal direction DD. In certain instances, the distal shaft 10540 may actually comprise the articulation actuator 10470 or otherwise operably interface therewith to provide desired axial articulation control motions thereto. In at least one arrangement, for example, the amount of articulation force applied to the articulation actuator 10470 employing such arrangement may be between 10-30 pounds as it adjusts dynamically. In some instances, an ideal amount of articulation force may be 20 pounds, for example. The static resist load of such arrangement may be as high as 80-150 pounds with a practical load of 100 pounds on the distal shaft 10540. Local pivotal termination of the articulation actuator close to the articulation joint may also minimize the chance of buckling. In various instances, buckling support could be integrated into the support of the drive gear 10530 or a spring biased or sliding joint bushing could be employed on the drive shaft 10520 to allow it to pivot but not buckle under compressive loads.

Figure 8:
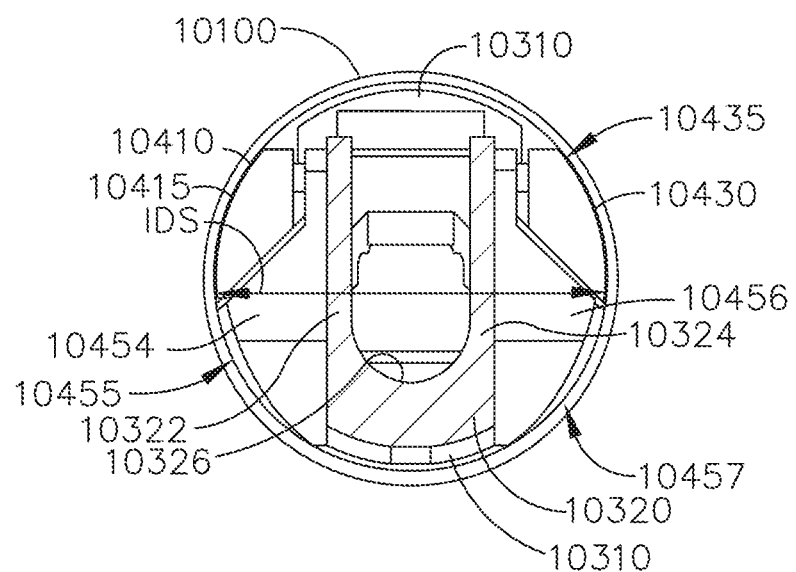
FIG. 8 is an end elevational view of the articulation joint of FIG. 7.
Figure 9:
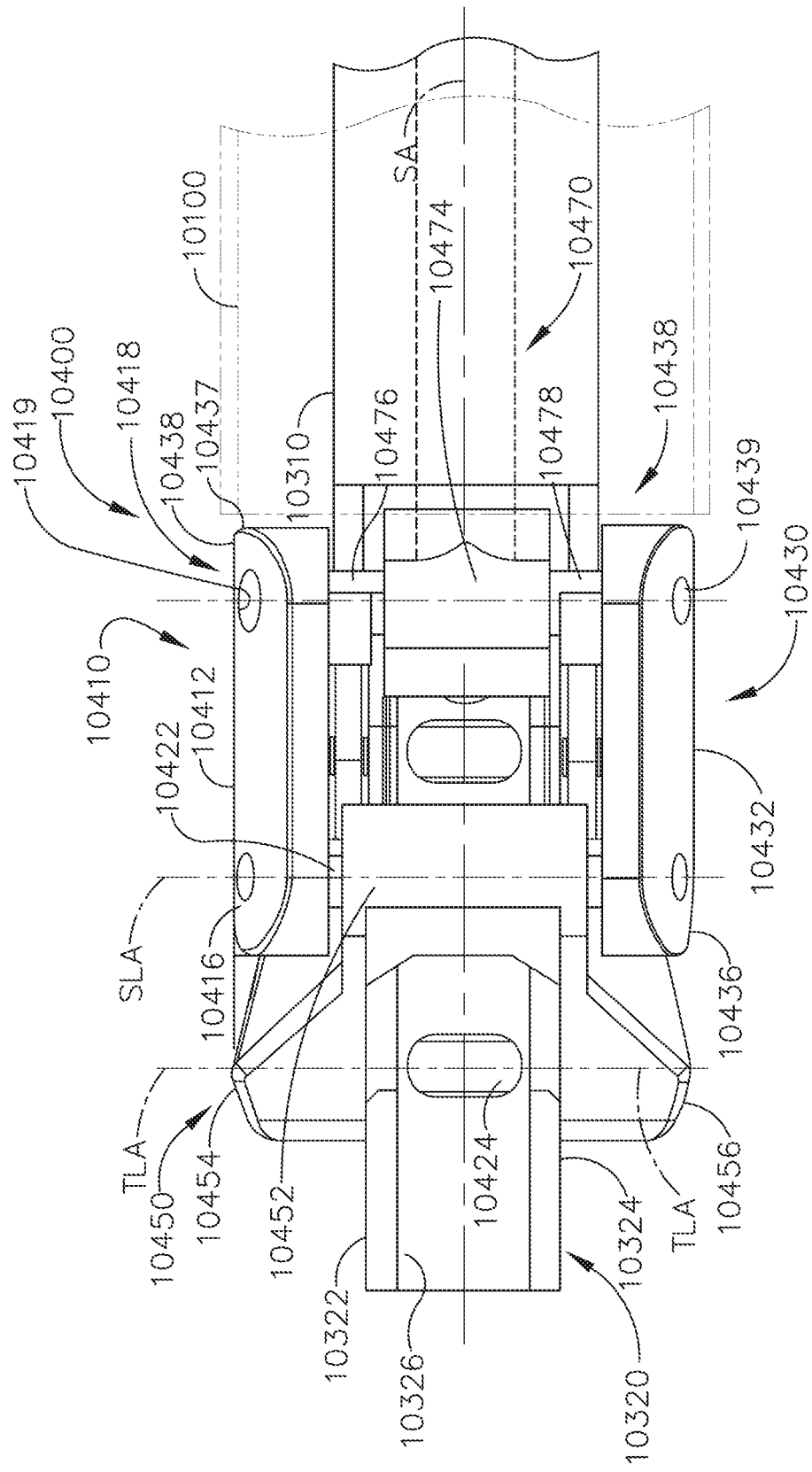
FIG. 9 is a top view of the articulation joint of FIG. 7.
Figure 10:
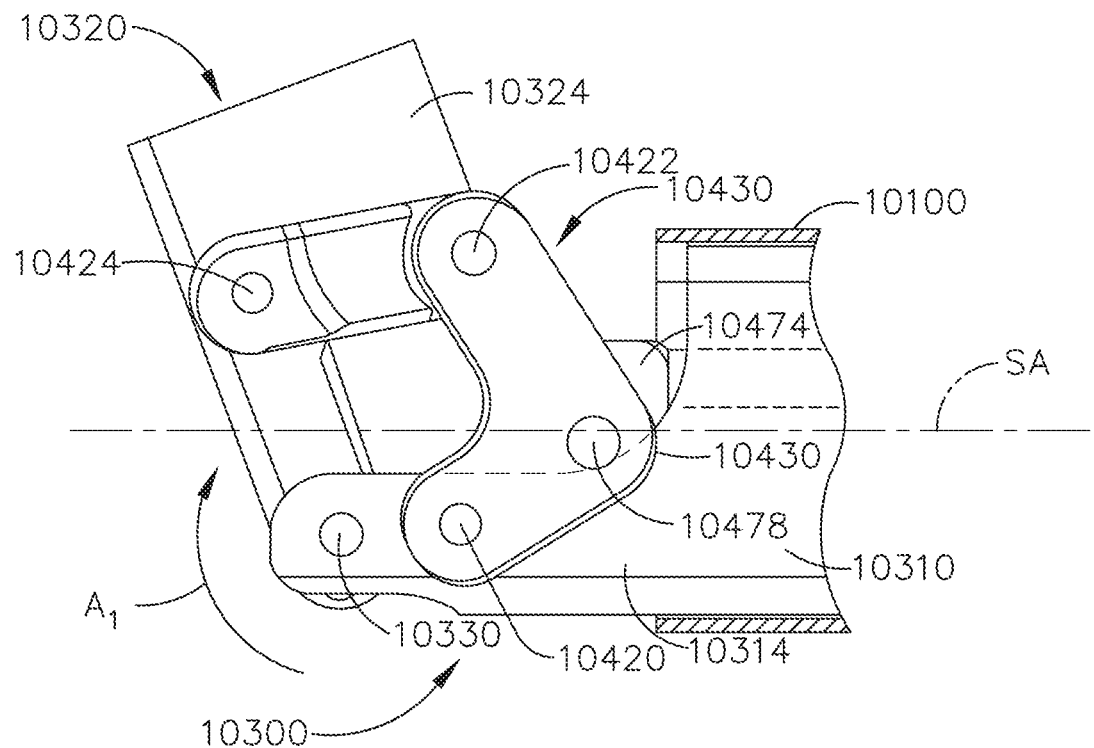
FIG. 10 is a side elevational view of the articulation joint of the surgical instrument of FIG. 4 articulated in a first direction.
Figure 11:
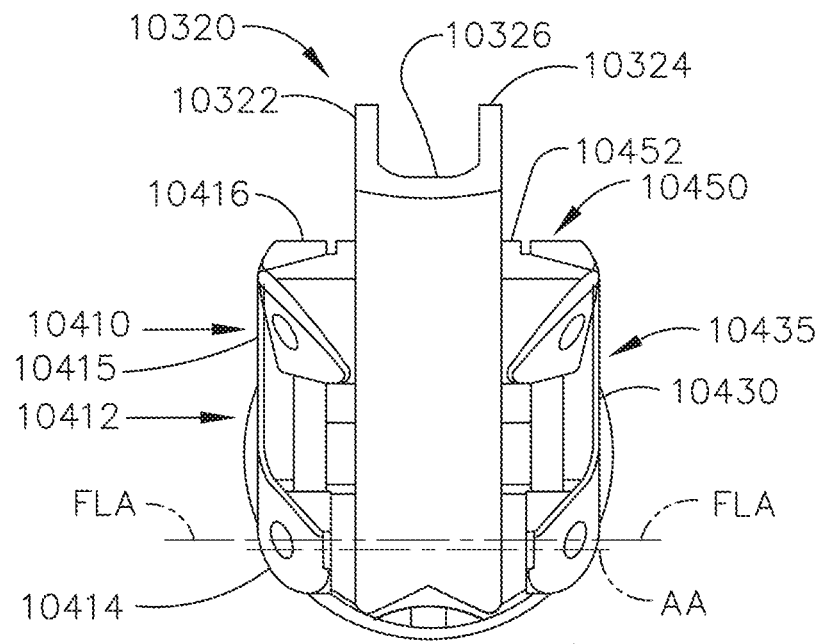
FIG. 11 is an end elevational view of the articulation joint of FIG. 10.
Figure 12:
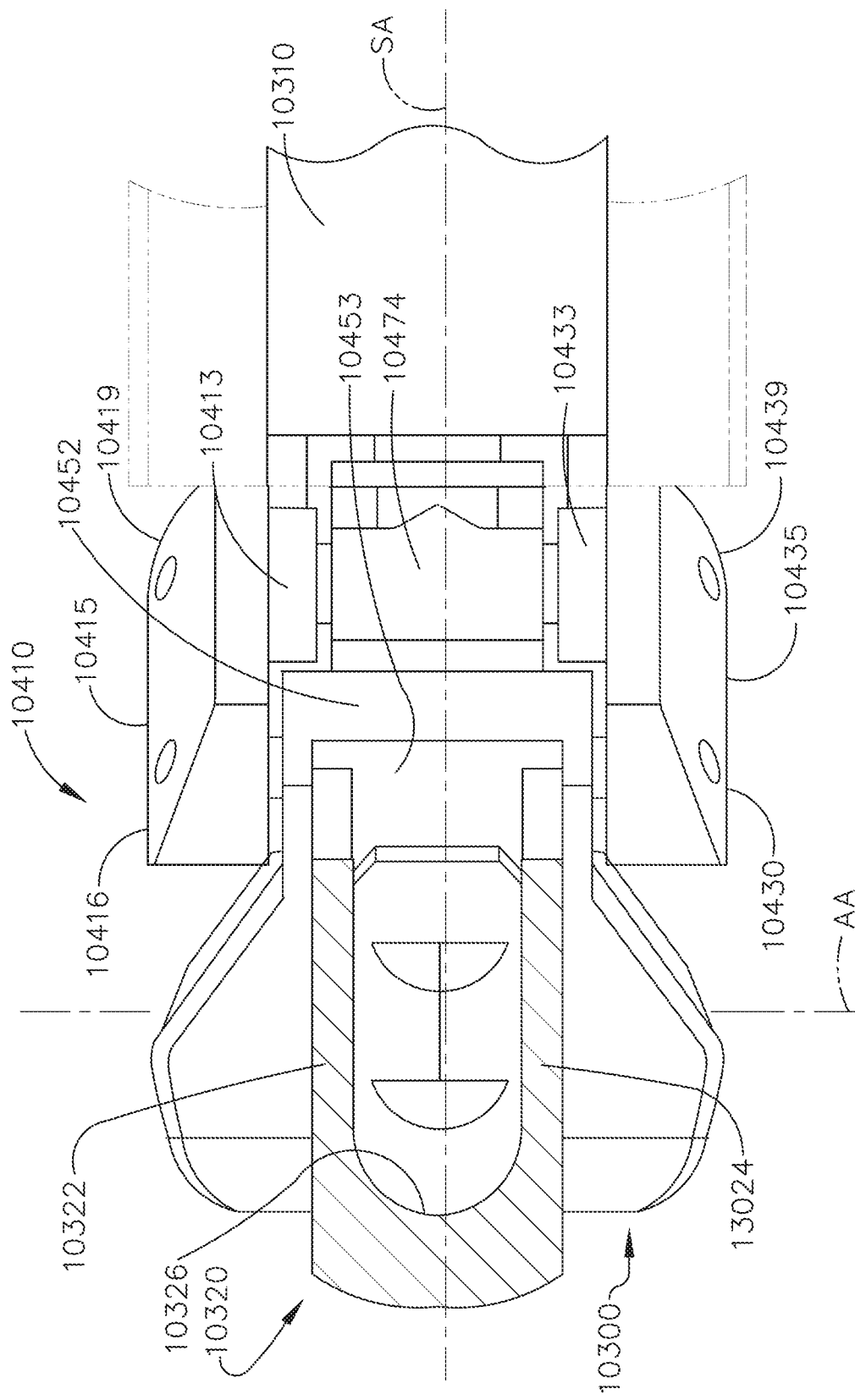
FIG. 12 is a top view of the articulation joint of FIG. 10.
Figure 18:
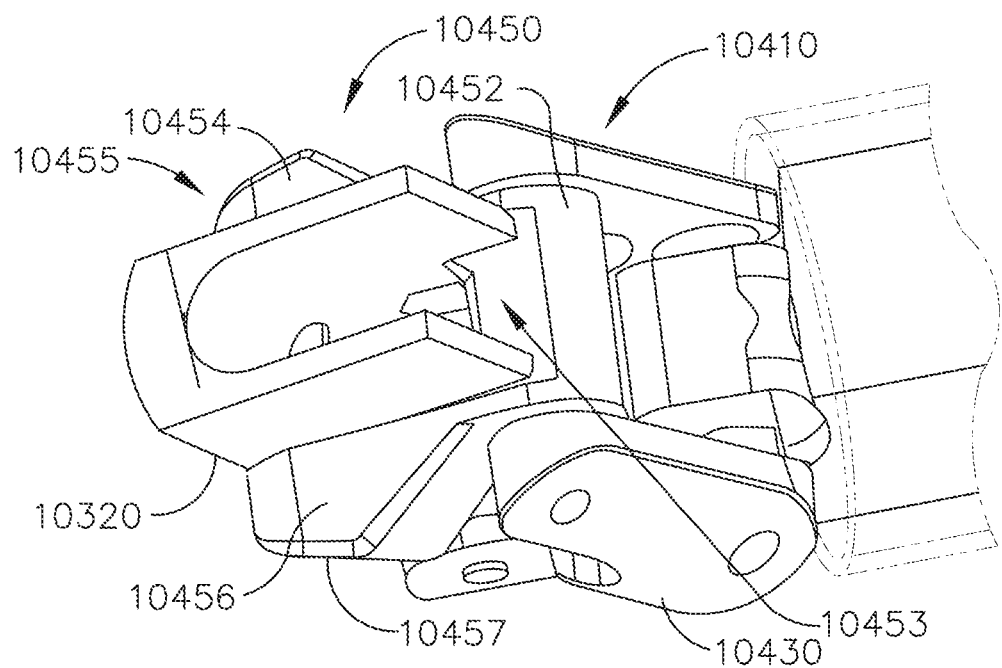
FIG. 18 is another perspective view of the articulation joint of FIG. 17.
Figure 17:
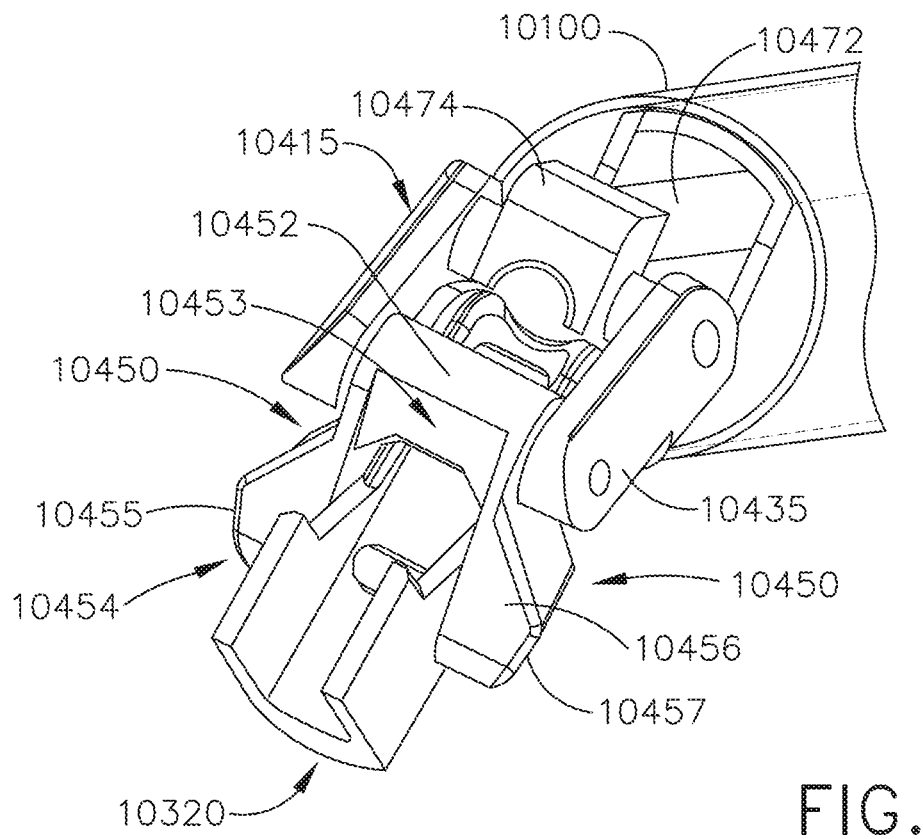
FIG. 17 is another perspective view of the articulation joint of the surgical instrument of FIG. 4.

Turning next to FIG. 17 and FIG. 18, to increase the range of articulation travel afforded by the articulation joint 10300, in at least one arrangement, the second link proximal end 10452 includes a recessed area 10453 configured to provide additional clearance for the proximal end effector frame member 10320 when the proximal end effector frame member 10320 is articulated to a maximum articulation angle. Also in at least one arrangement, the right proximal link 10410 includes a contoured or arcuate outer surface 10415 and the left proximal link 10430 includes a contoured or arcuate outer surface 10435. See FIG. 8. Similarly, the right second link arm 10454 has a contoured or arcuate outer surface 10455 and the left second link arm 10456 has a contoured or arcuate outer surface 10457. Such contoured link configurations may be much stronger than prior uncontoured or relatively flat link arrangements that have been employed in other articulation joint arrangements. As can be seen in FIG. 8, such arcuate surfaces on the right proximal link 10410 and the left proximal link 10430 generally align with the internal diameter ID of the proximal outer shaft tube 10110.

Figure 21:
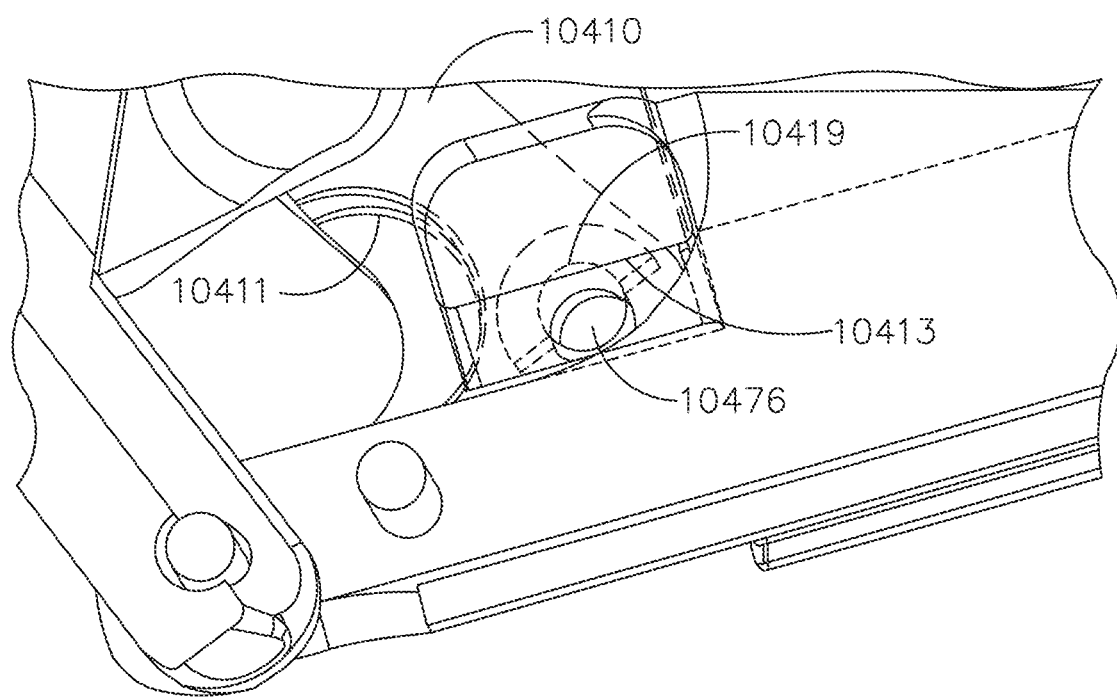
FIG. 21 is a partial cross-sectional view of the articulation joint of FIG. 4 articulated in a first direction.

As can be seen in FIG. 21, the right proximal link 10410 comprises a right cut out area 10411 that enables the right proximal link 10410 to articulate over top of a right end of 10334 articulation pin 10330. Such arrangements serve to facilitate additional articulation travel of the surgical end effector 10200 about the articulation axis AA. Further, in various instances, to provide additional strength to the right proximal link 10410 while facilitating additional articulation travel, a right articulation boss or rib segment 10413 is formed on an inside surface of the right proximal link 10410. The right articulation rib segment 10413 provides additional pivotal support to the right proximal link 10410 as it pivots relative to the right link pin 10476. However, the right articulation rib segment 10413 only extends partially around the right link pin 10476 to provide additional pivotal clearance for the right proximal link 10410 to pivot about the right link pin 10476.

Figure 19:
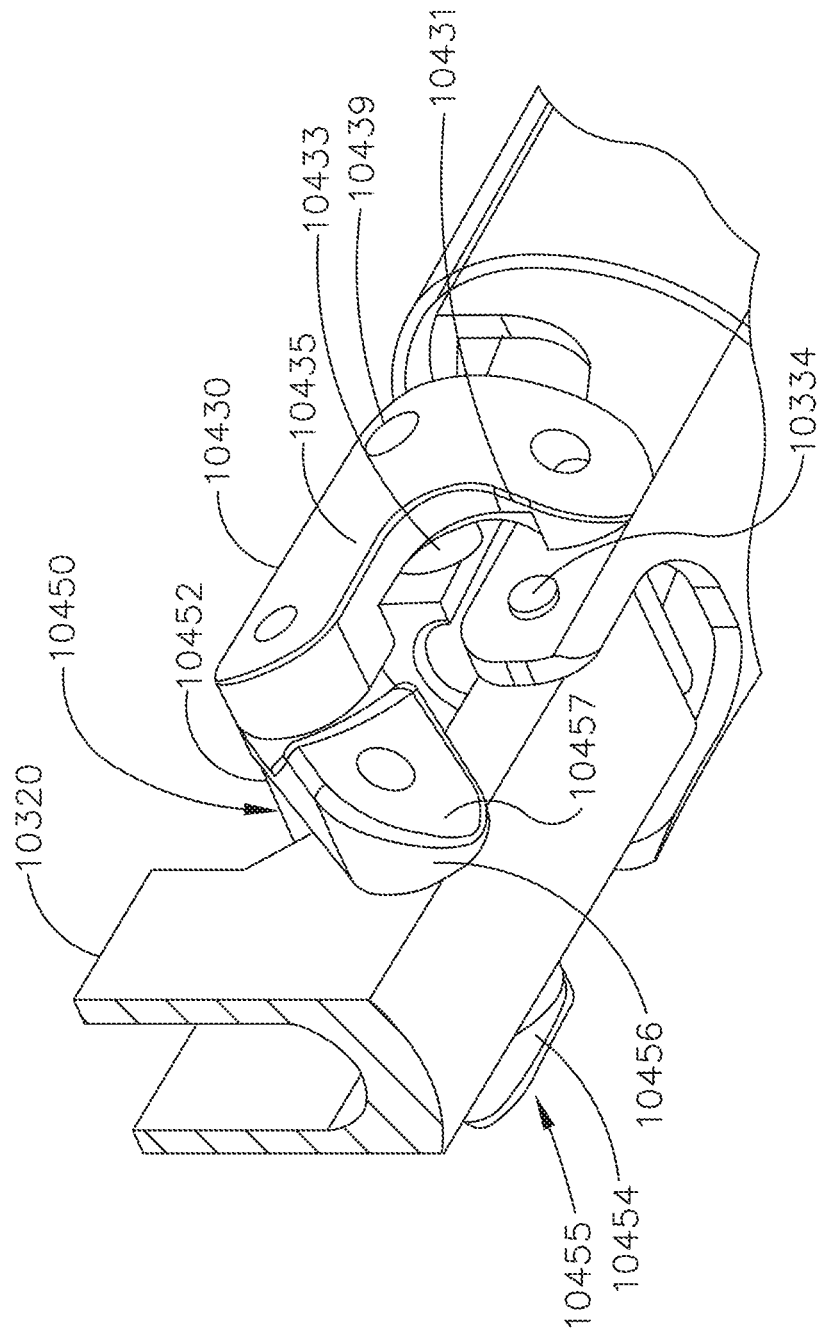
FIG. 19 is another perspective view of the articulation joint of FIG. 17 in an unarticulated position.
Figure 20:
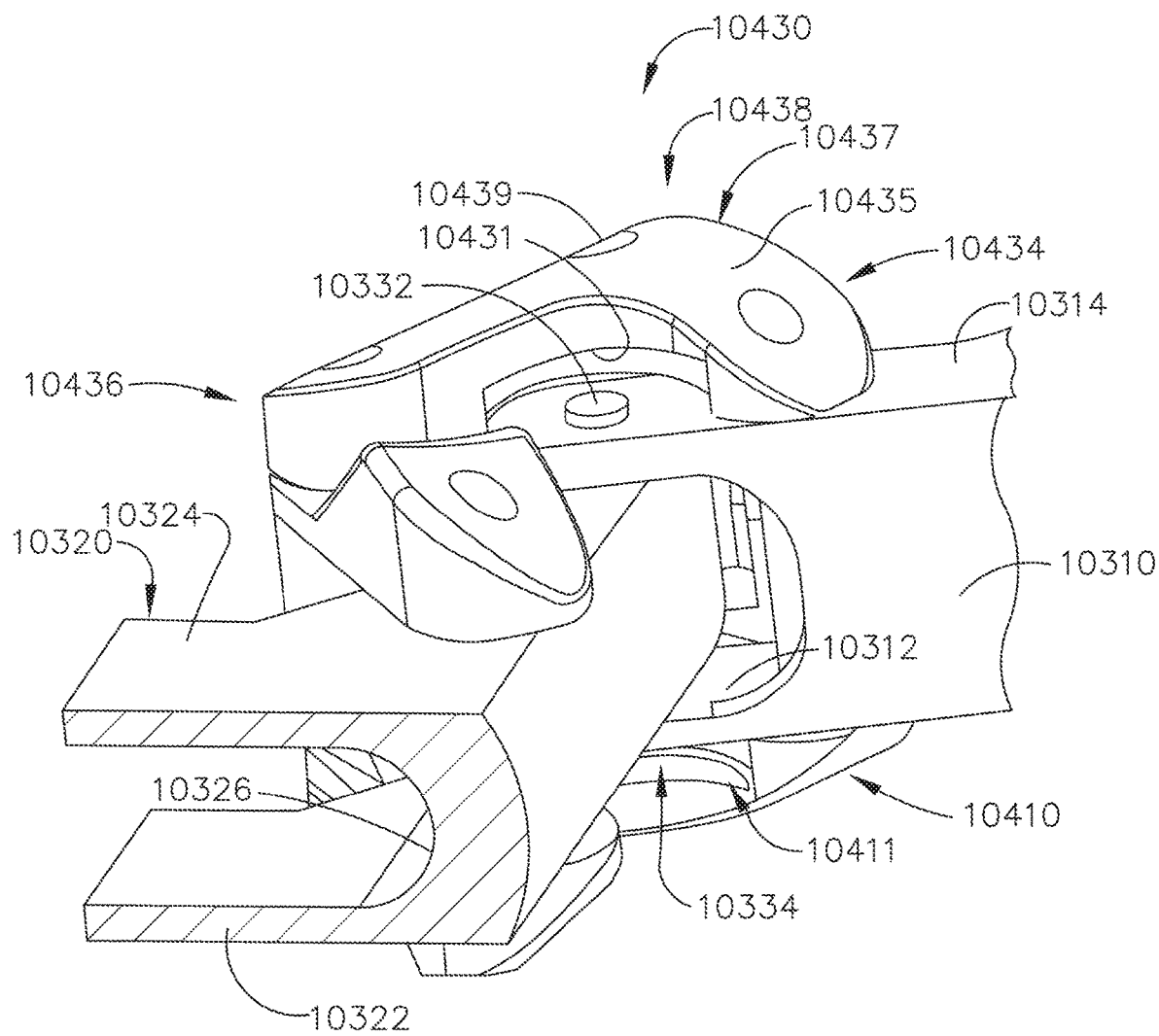
FIG. 20 is a bottom perspective view of the articulation joint of FIG. 4 articulated in a second direction.

Likewise, the left proximal link 10430 comprises a left cut out area 10431 that enables the left proximal link 10430 to articulate over top of a left end 10332 of the articulation pin 10330. See FIG. 20. Such arrangements serve to facilitate additional articulation travel of the surgical end effector 10200 about the articulation axis AA. Further, in various instances, to provide additional strength to the left proximal link 10430 while facilitating additional articulation travel, a left articulation boss or rib segment 10433 is formed on an inside surface of the left proximal link 10430. See FIG. 19. The left articulation rib segment 10433 provides additional pivotal support to the left proximal link 10430 as it pivots relative to the left link pin 10478. However, the left articulation rib segment 10433 only extends partially around the left link pin 10478 to provide additional pivotal clearance for the left proximal link 10430 to pivot about the left link pin 10478.

The above-described articulation joint arrangement, as well as the other articulation joint arrangements disclosed herein may represent vast improvements over prior articulation joint arrangements that comprise relatively planar articulation links that are located or attached between the shaft portion of the device and the surgical end effector only on one side of the shaft axis. Because the right proximal link is located on a right side of the shaft axis SA and the left proximal link is located on a left side of the shaft axis SA and the second link spans the shaft axis SA to be coupled to the right proximal link and left proximal link, the lateral stability of such articulation joint may be enhanced. For example, such articulation joint may provide improved resistance to external lateral loads experienced by the end effector when interacting with adjacent tissue or organs or to other external forces that are applied to the end effector during use.

Figure 22:
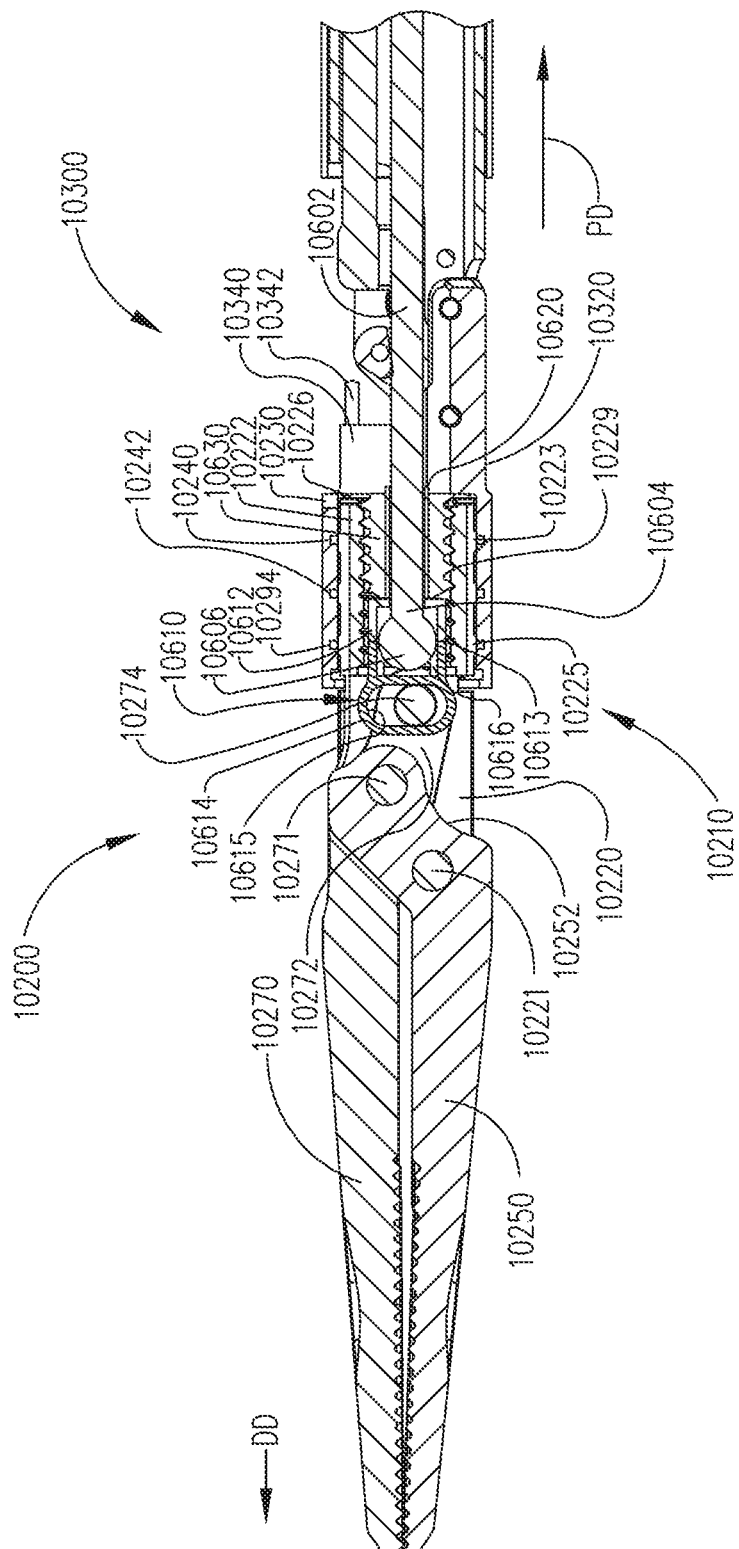
FIG. 22 is a cross-sectional side view of a portion of the surgical instrument of FIG. 4 with jaws thereof in a closed position.
Figure 23:
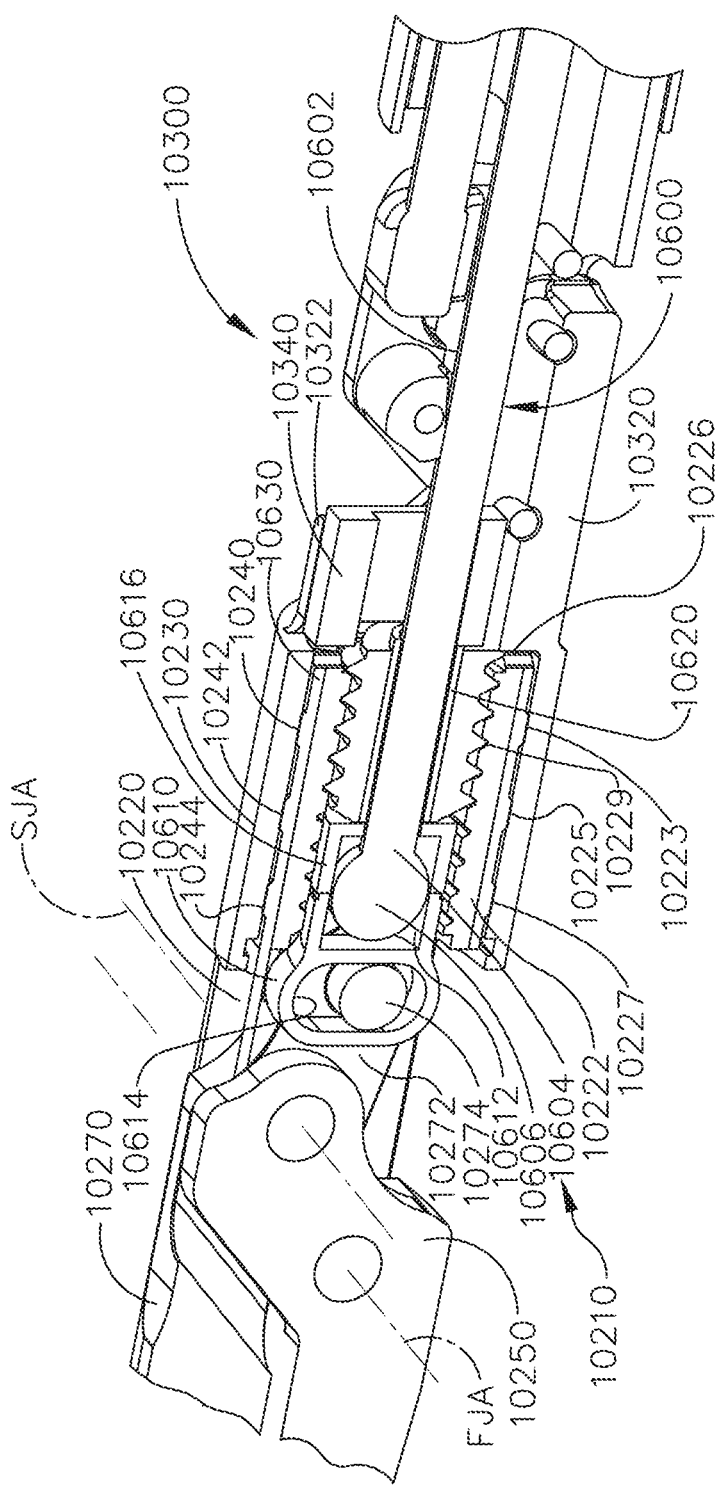
FIG. 23 is a cross-sectional perspective view of the portion of the surgical instrument of FIG. 22.

In various instances, as can be seen in FIGS. 4, 22, and 23, the surgical end effector 10200 comprises a first jaw 10250 and a second jaw 10270. The first jaw 10250 and the second jaw 10270 are each pivotally supported on the end effector frame assembly 10210 and are movable between an open position and a closed position upon an application of axial control motions applied to one of the jaws 10250, 10270. The first jaw 10250 and the second jaw 10270 may comprise any of the jaw arrangements disclosed herein, for example. Turning specifically to FIG. 22 and FIG. 23, the end effector frame assembly 10210 comprises a distal frame member 10220 that is rotatably supported in a proximal frame housing 10230 that is fixedly attached to the proximal end effector frame member 10320. For example, the proximal frame housing 10230 may be attached to the proximal end effector frame member 10320 by welding, adhesive, etc. In the illustrated example, the distal frame member 10220 comprises a proximal barrel portion 10222 that is configured to rotate within proximal frame housing 10230 as will be discussed in further detail below.

Figure 24:
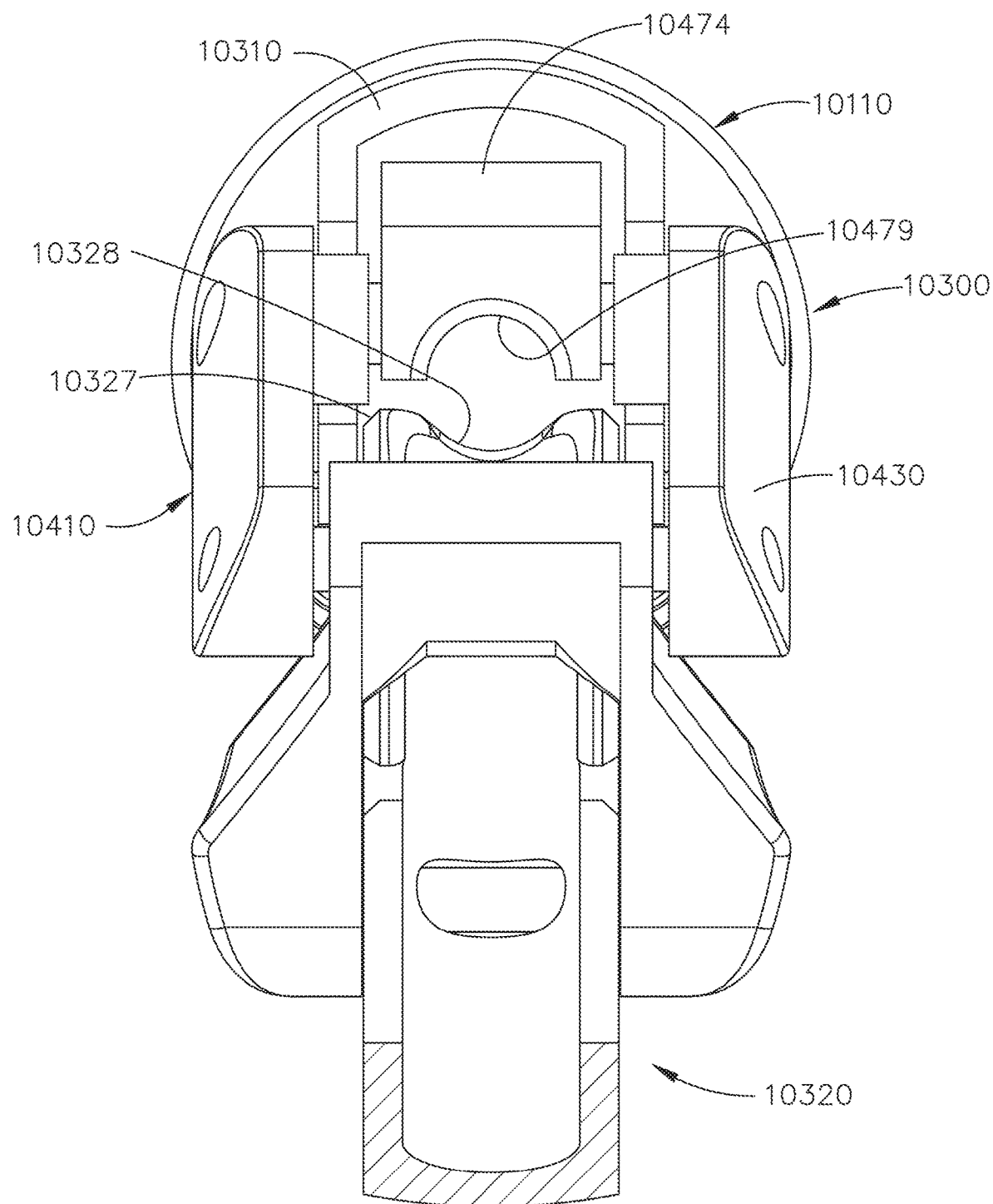
FIG. 24 is an end perspective view of the articulation joint of the surgical instrument of FIG. 4 with the articulation joint articulated in a second direction.

In various instances, the first jaw 10250 is pivotally pinned to the distal frame member 10220 for selective pivotal travel relative thereto about a first jaw axis FJA defined by a first jaw pin 10221. See FIG. 23. The second jaw 10270 is pivotally pinned to the first jaw 10250 for selective pivotal travel relative to the first jaw 10250 about a second jaw axis SJA that is defined by a second jaw pin 10271. In certain instances, the second jaw axis SJA is parallel to the first jaw axis FJA. The first jaw axis FJA and the second jaw axis SJA are both transverse to the shaft axis SA. In at least one arrangement as shown in FIG. 23, the second jaw 10270 is configured to receive axial jaw control motions from an end effector drive member 10600. In certain instances, the end effector drive member 10600 comprises a flexible rotary shaft 10602 that is capable of rotation while maintaining an ability to bend and flex to accommodate articulation of the surgical end effector 10200 in the manners described herein. As can be seen in FIG. 24, the distal end formation 10474 of the articulation shaft 10472 comprises an arcuate support surface 10479 and a proximal end portion 10327 of the proximal end effector frame member 10320 comprises an arcuate support surface 10328. The arcuate support surfaces 10479 and 10328 serve to support the flexible rotary drive shaft 10602 as the surgical end effector 10200 is articulated on each side of the shaft axis SA through an entire range of articulation.

Figure 26:
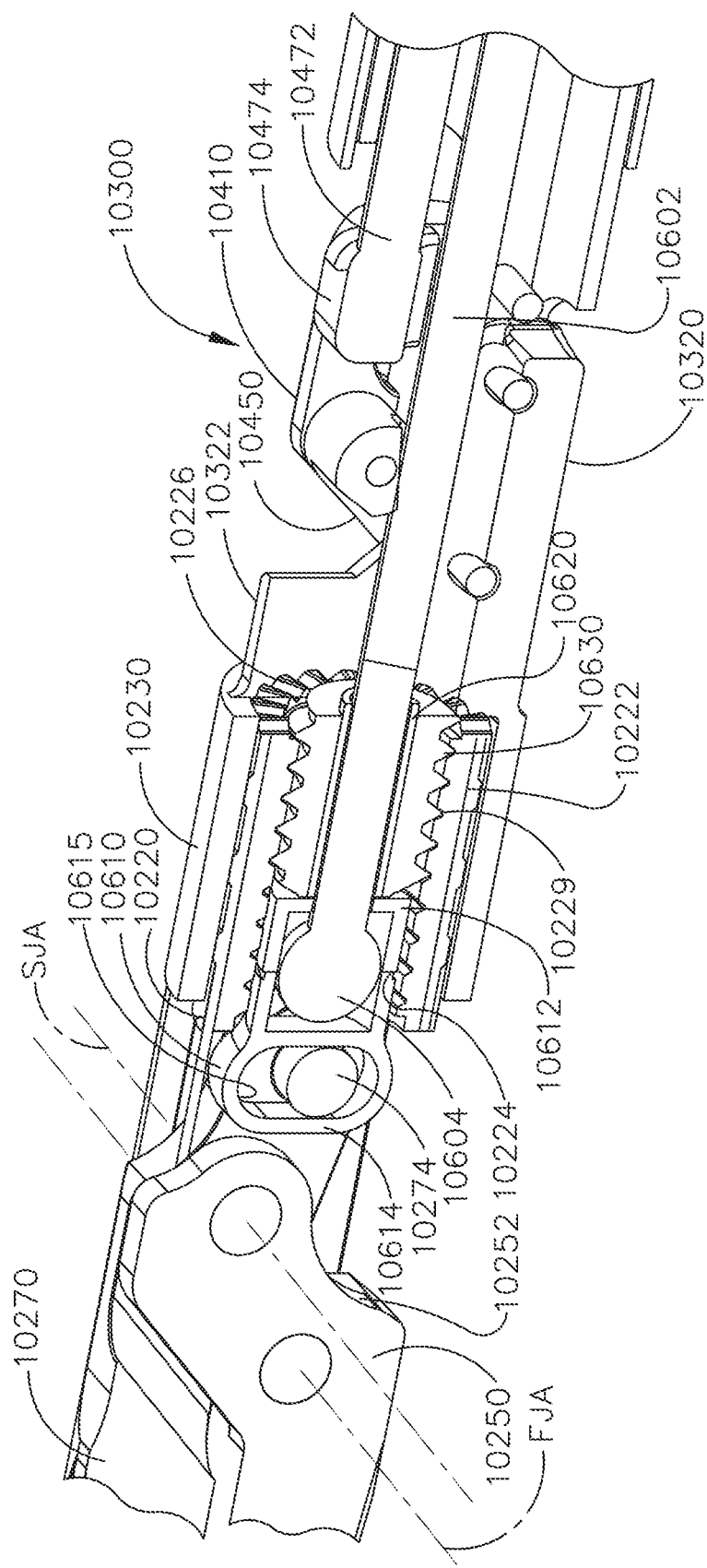
FIG. 26 is a cross-sectional perspective view of the surgical instrument of FIG. 25 with jaws thereof in a closed position.
Figure 27:
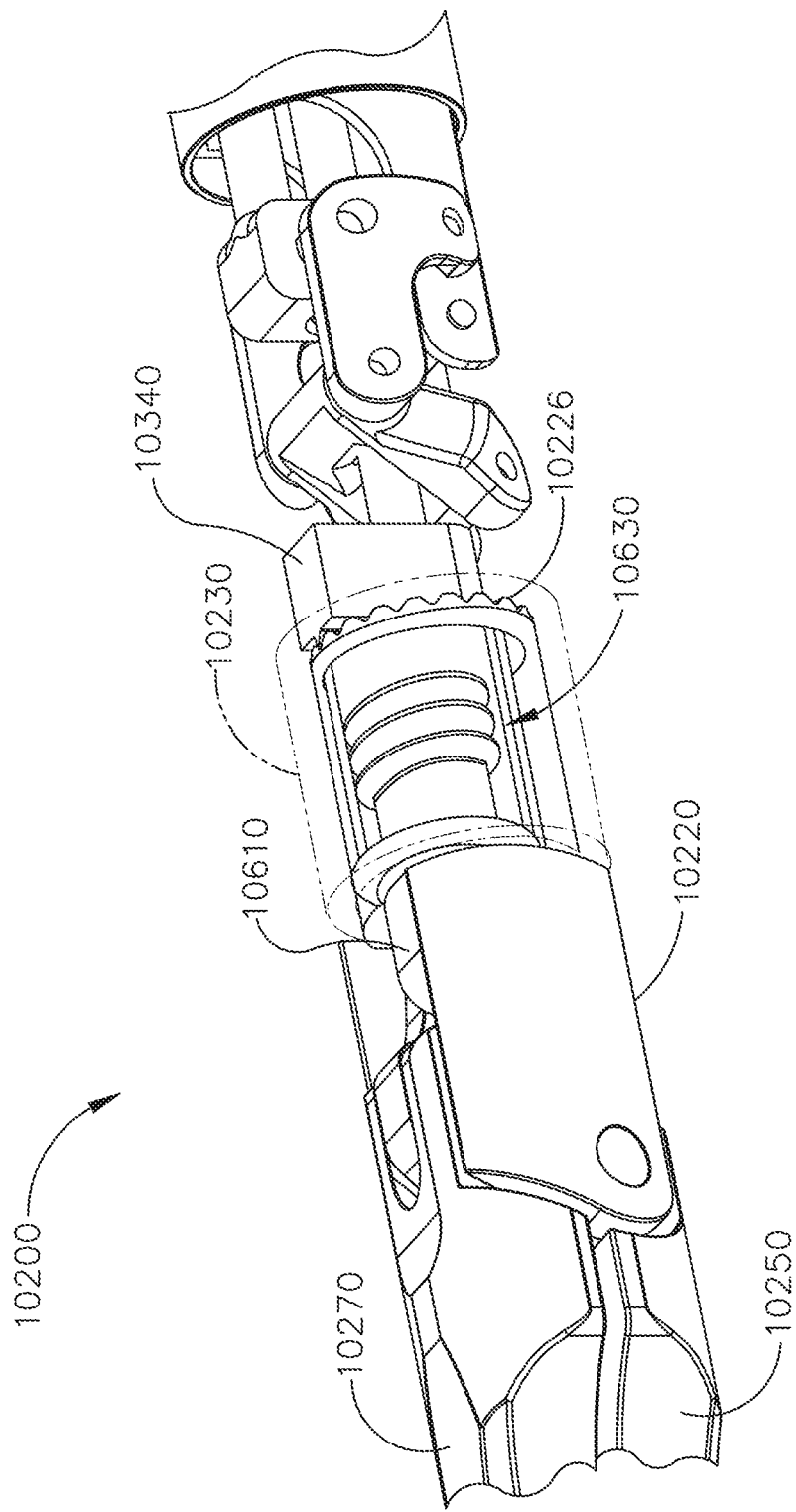
FIG. 27 is another perspective view of the surgical instrument of FIG. 26 with portions thereof shown in phantom.

Returning to FIGS. 22 and 23, a proximal end 10272 of the second jaw 10270 comprises a second jaw attachment pin 10274 that is configured to operably interface with an actuator yoke assembly 10610. In the illustrated example, the actuator yoke assembly 10610 comprises a proximal yoke housing segment 10612 and a distal yoke housing segment 10614 that are coupled together to facilitate relative rotation therebetween. For example, the proximal yoke housing segment 10612 and the distal yoke housing segment 10614 may be coupled by a spring clip 10613 or other faster arrangement such that the proximal yoke housing segment 10612 is rotatable relative to the distal yoke housing segment 10614 while remaining attached thereto. As can be seen in FIGS. 22 and 26, the distal yoke housing segment 10614 includes an elongate slot 10615 that facilitates vertical movement of the second jaw attachment pin 10274 therein. The first jaw 10250 comprises a cam surface 10252 that is configured to cammingly interact with the distal yoke housing segment 10614 when the actuator yoke assembly 10610 is driven distally to cam the first jaw 10250 into an open position about the first jaw pin 10221. A distal end 10604 of the flexible drive shaft 10602 is rotatably coupled to the actuator yoke 10610 to facilitate rotation of the flexible drive shaft 10602 relative to the actuator yoke assembly 10610. In one arrangement, the distal end 10604 comprises a ball feature 10606 that is rotatably housed within a rotation housing 10616 formed within the distal yoke housing segment 10614 and the proximal yoke housing segment 10612. The actuator yoke assembly 10610 is received within a bore 10224 within the proximal barrel portion 10222 to facilitate axial travel of the distal yoke housing segment 10614 therein as well as axial and rotational travel of the proximal yoke housing segment 10612 therein.

Figure 25:
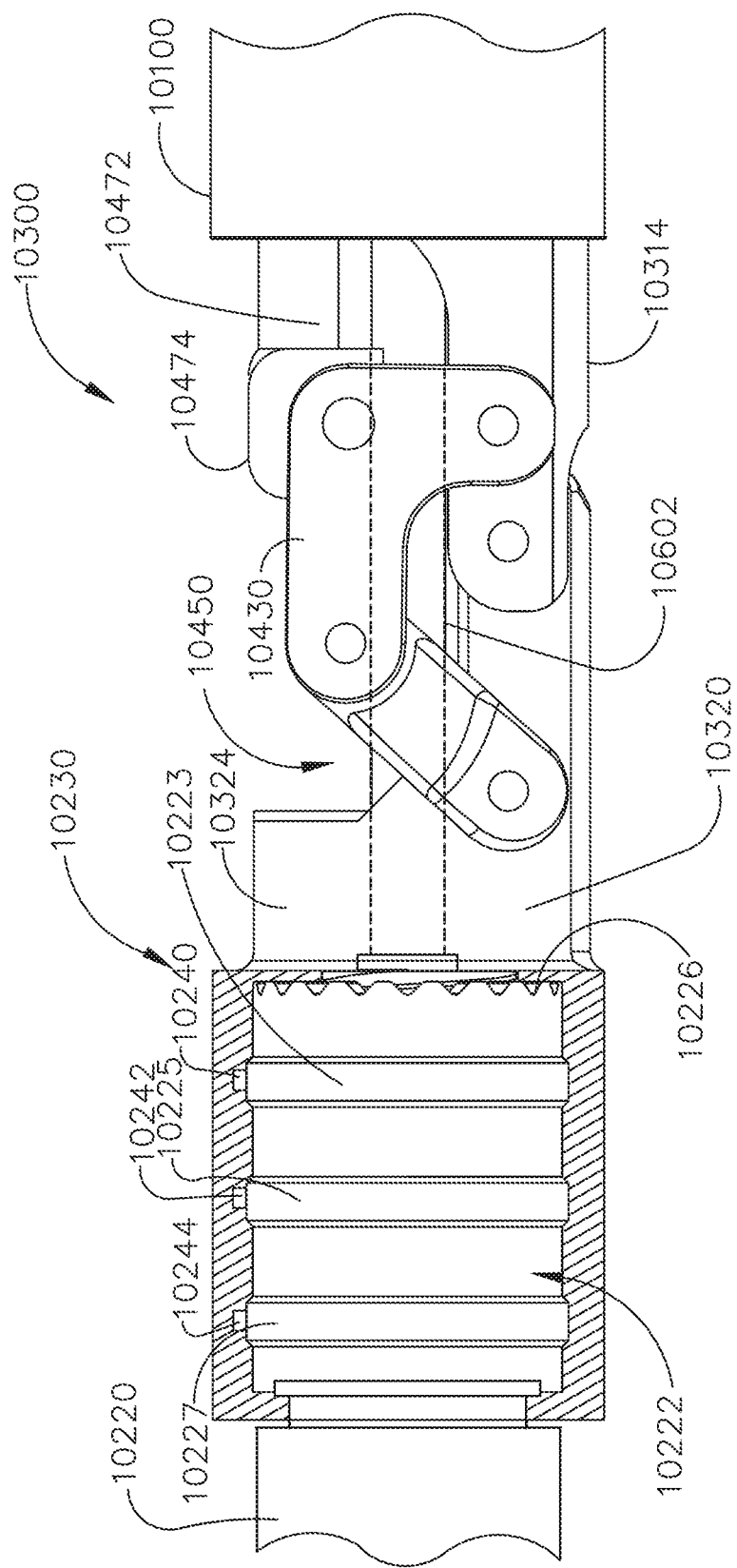
FIG. 25 is a side elevational view of a portion of the surgical instrument of FIG. 4 with portions thereof shown in phantom.

To facilitate locking of the surgical end effector 10200 in a desired rotary position about the shaft axis SA, a series of radial locking grooves 10226 are formed in a proximal end of the barrel portion 10222. See FIGS. 25 and 26. The series of radial locking grooves 10226 are configured to be lockingly engaged by a lock insert 10340 that is received between the upstanding support sides 10322, 10324 of the proximal effector frame member 10320. In various arrangements, the lock insert 10340 is biased in a distal direction into locking engagement with the locking grooves 10226 by a biasing member or a spring (not shown). A flexible unlocking cable 10342 or other flexible actuator is coupled to the lock insert 10340 and extends through the proximal shaft segment 10100 to interface with a control system in the housing. In various instances, for example, the flexible unlocking cable 10342 may interface with a motor or other control arrangement configured to selectively pull the unlocking cable proximally to move the lock insert out of locking engagement with the locking grooves 10226 on the proximal barrel portion 10222.

Referring to FIG. 22, a threaded member 10630 is mounted on a bushing 10620 that is non-rotatably mounted to the flexible rotary drive shaft 10602. The threaded member 10630 is also attached to the proximal yoke housing segment 10612 by welding, adhesive, molding, etc. Thus, rotation of the flexible rotary drive shaft 10602 will result in the rotation of the threaded member 10630 as well as the proximal yoke housing segment 10612, but not the distal yoke housing segment 10614. The threaded member 10630 is in threaded engagement with a plurality of internal threads 10229 formed in the proximal barrel portion 10222 of the distal frame member 10220. When the lock insert 10340 is in locking engagement with the locking grooves 10226 in the proximal barrel portion 10222, rotation of the rotary drive shaft 10602 and the threaded member 10630 in a first direction will drive the actuator yoke assembly 10610 in the distal direction DD to move the first jaw 10250 and the second jaw 10270 into an open position. Because the lock insert 10340 is in locking engagement with the lock grooves 10226, the proximal barrel portion 10222 (and the surgical end effector 10200) is prevented from rotating about the shaft axis SA when the rotary flexible drive shaft 10602 is rotated. Instead, the threaded drive nut 10630 rotates within the proximal barrel portion 10222 and moves distally to drive the actuator yoke assembly 10610 in the distal direction as well. While the proximal yoke housing segment 10612 rotates, the distal yoke housing segment 10614 does not rotate.

The surgical end effector 10200 of the illustrated example is also selectively rotatable about the shaft axis SA to further enhance the positionability of the surgical end effector 10200 during use. To rotate the surgical end effector 10200 about the shaft axis SA, the unlocking cable 10342 is pulled proximally to cause the lock insert 10340 to disengage the lock grooves 10226 in the proximal barrel portion 10222. Thereafter, the flexible rotary drive shaft 10602 is rotated in a desired direction. In such instance, there is enough friction between the threaded member 10630 and the internal threads 10229 formed in the proximal barrel portion 10222 of the distal frame member 10220 such that rotation of the threaded member 10630 will cause the proximal barrel portion 10222 (and the surgical end effector 10200) to rotate about the shaft axis SA.

In one application, the surgical instrument 10000 may be used as follows in connection with performing a laparoscopic procedure wherein a trocar has been installed in a patient. To insert the surgical end effector 10200 through the trocar cannula 10010, the clinician (or robotic control system) may have to first actuate the articulation drive system to cause the articulation shaft 10472 to move the surgical end effector 10200 into an unarticulated position if it is not already in that position. See FIG. 4. Also, in certain instances, the drive system that controls the flexible rotary drive shaft 10602 may need to be actuated to bring the first jaw 10250 and the second jaw 10270 into the fully closed position if the first jaw 10250 and the second jaw 10270 are not already in that position. Once the surgical end effector 10200 is in the unarticulated position with the first jaw 10250 and the second jaw 10270 in the closed position, the surgical end effector 10200 may be inserted through the trocar cannula 10010 into the surgical site. Once the surgical end effector 10200 has been inserted into the surgical site, the clinician or robotic control system may then actuate the articulation drive system in an appropriate manner to articulate the surgical end effector 10200 into a desired articulated position relative to the tissue to be treated (target tissue). In addition, if necessary, the unlocking cable 10342 may be actuated to unlock the surgical end effector 10200 to permit the surgical end effector 10200 to be rotated about the shaft axis SA into a desired rotary position. Once in the desired rotary position, the unlocking cable 10342 may then be deactivated to permit the lock insert 10340 to return to the locked position to retain the end effector 10200 in the desired rotary position. The surgical end effector 10200 may be rotated before and/or after the surgical end effector 10200 has been articulated. Thereafter, the drive system may be actuated to rotate the flexible rotary drive shaft 10602 in a first rotary direction to drive the actuator yoke assembly 10610 distally to open the first and second jaws 10250, 10270. Once the jaws 10250, 10270 are open and the target tissue has been positioned therein, the drive system may again be actuated to rotate the flexible rotary drive shaft 10602 in a second rotary direction to drive the actuator yoke assembly 10610 proximally to pull the first and second jaws 10250, 10270 to a closed position to clamp the target tissue therebetween. Once the tissue has been treated, the jaws 10250, 10270 are opened to disengage the treated tissue and then returned to a closed position. The surgical end effector 10200 is returned to the unarticulated position to enable the surgical end effector 10200 to be withdrawn from the patient through the trocar cannula.

To facilitate transfer of electric signals/power between the housing and the surgical end effector 10200 and, more particularly, to one or both of the first and second jaws, conductors may be provided through the proximal shaft segment 10100 and span the articulation joint 10300 to terminate in a series of contacts supported in the proximal frame housing 10230. In the example illustrated in FIG. 25, three fixed contacts 10240, 10242, 10244 are mounted in the proximal frame housing 10230. An annular contact 10223 is supported around the perimeter of the proximal barrel portion 10222 of the distal frame member 10220. The fixed contact 10240 is in electrical contact with the annular contact 10223 as the distal frame member 10220 is rotated about the shaft axis SA. An annular contact 10225 is supported around the perimeter of the proximal barrel portion 10222 of the distal frame member 10220. The fixed contact 10242 is supported in electrical contact with the annular contact 10225 as the distal frame member 10220 is rotated about the shaft axis SA. An annular contact 10227 is supported around the perimeter of the proximal barrel portion 10222 of the distal frame member 10220. The fixed contact 10244 is in electrical contact with annular contact 10227 as the distal frame member 10220 is rotated about the shaft axis SA. The fixed contacts 10240, 10242, 10244 may also extend into one or both of the first and second jaws 10250, 10270 to transmit signals/power thereto.

Figure 28:
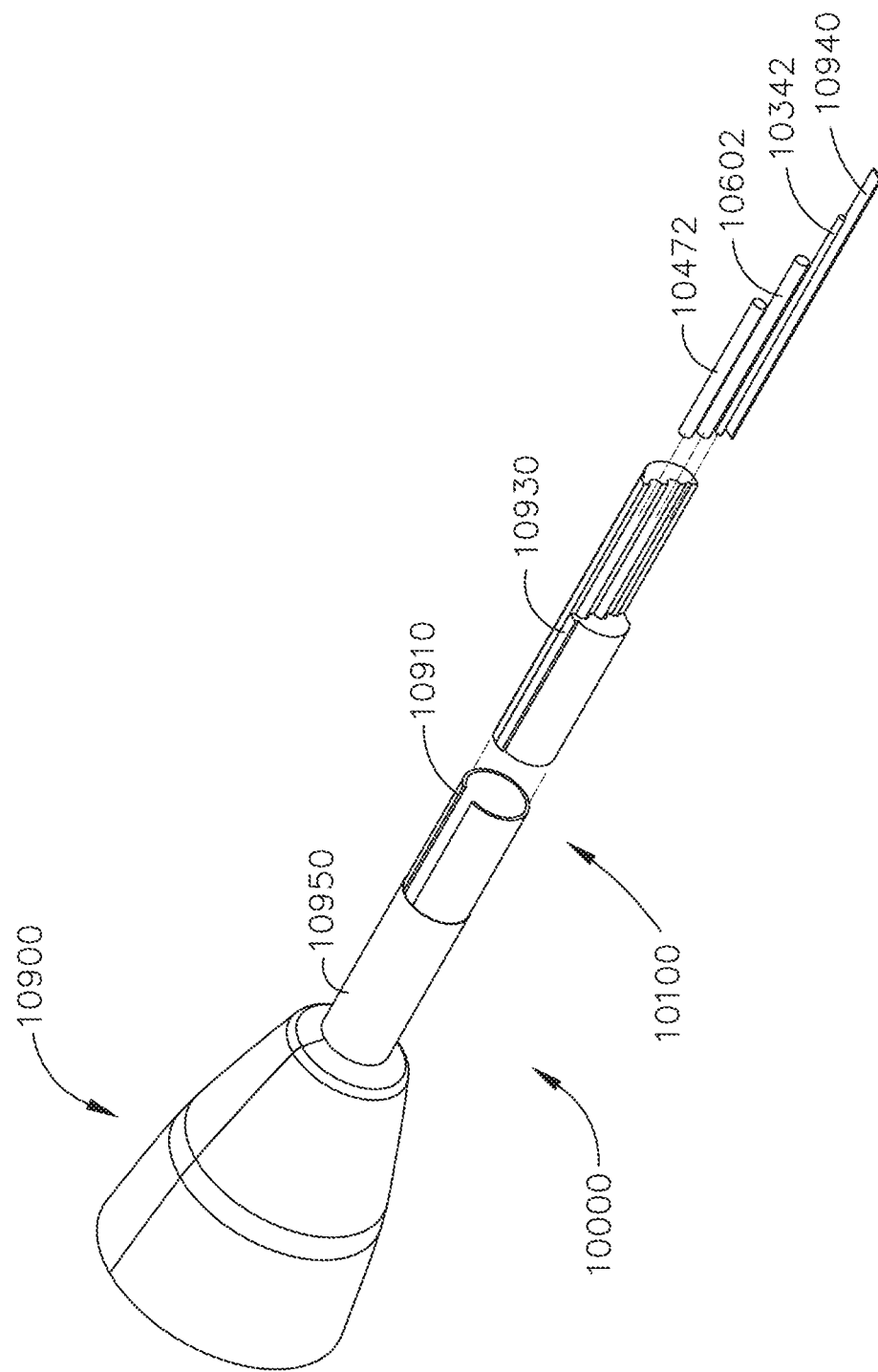
FIG. 28 is a partial cross-sectional perspective view of a proximal shaft segment embodiment, in accordance with at least one aspect of the present disclosure.
Figure 29:
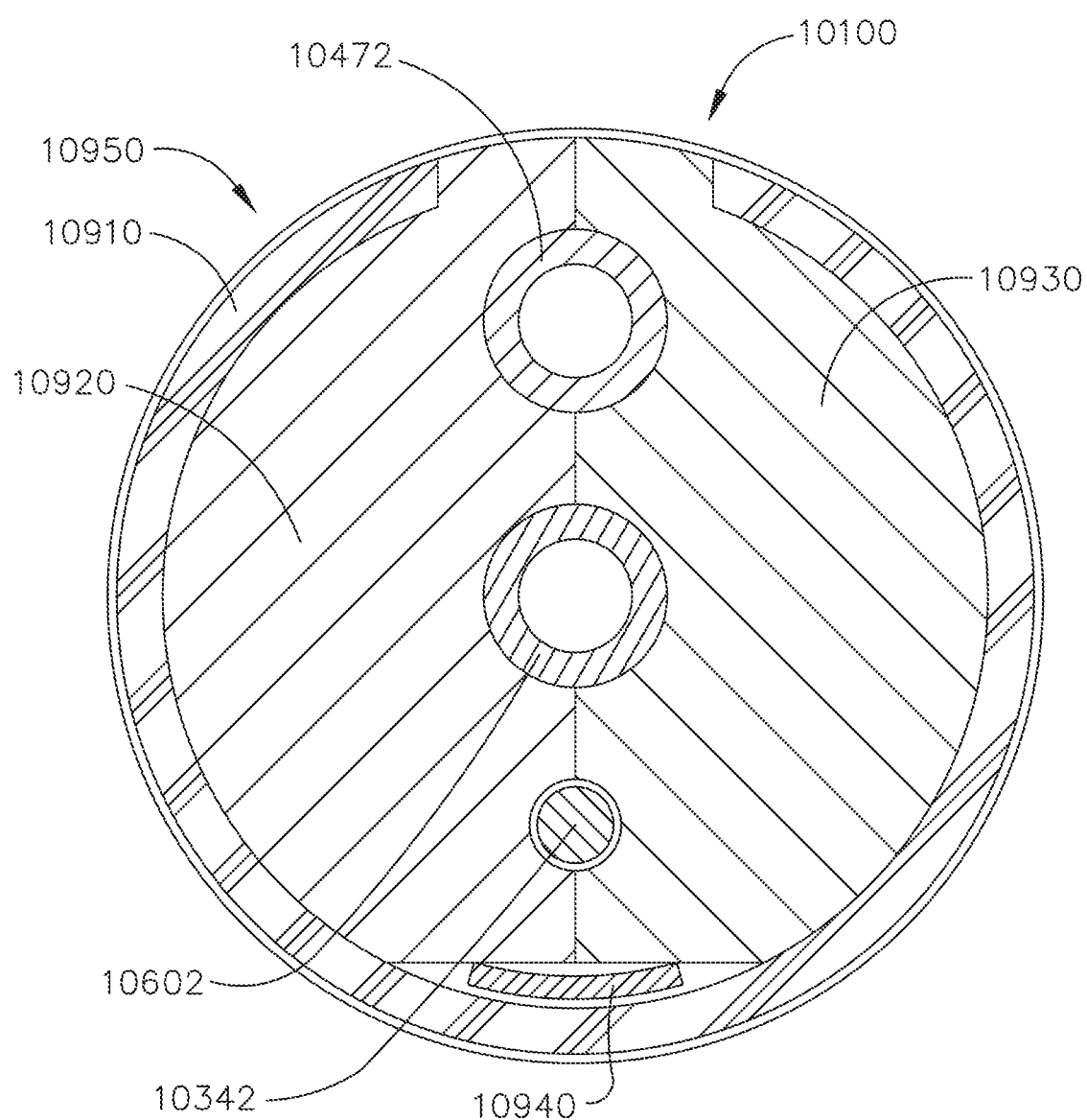
FIG. 29 is a cross-sectional end view of the proximal shaft segment of FIG. 28.

FIGS. 28 and 29 illustrate portions of the surgical instrument 10000 for facilitating transfer of electric signals/power between a housing 10900 and the surgical end effector 10200 (FIG. 4). As can be seen in FIG. 29, the proximal shaft segment 10100 may comprise a U-shaped hollow tube 10910 that supports a right shaft frame segment 10920 and a left shaft frame segment 10930. The right shaft frame segment 10920 and left shaft frame segment 10930 serve to rotatably support the rotary drive shaft 10602, the articulation shaft 10472, and the locking cable arrangement 10342 within the U-shaped hollow tube 10910. The right shaft frame segment 10920 and left shaft frame segment 10930 also support a flex circuit 10940 that may communicate with various control components/power sources within the housing 10900 and spans across the articulation joint 10300. The flex circuit 10940 may be coupled to the three fixed contacts 10240, 10242, 10244 that are mounted in the proximal frame housing 10230. Such arrangement facilitates transfer of electrical power between the housing 10900 and the surgical end effector 10200 while facilitating articulation and rotation of the surgical end effector 10200 relative to the proximal shaft segment 10100. As can also be seen in FIGS. 28 and 29, the shaft segment 10100 may be retained together by a layer of shrink wrap 10950 which may also prevent the infiltration of fluids therein.

Figure 30:
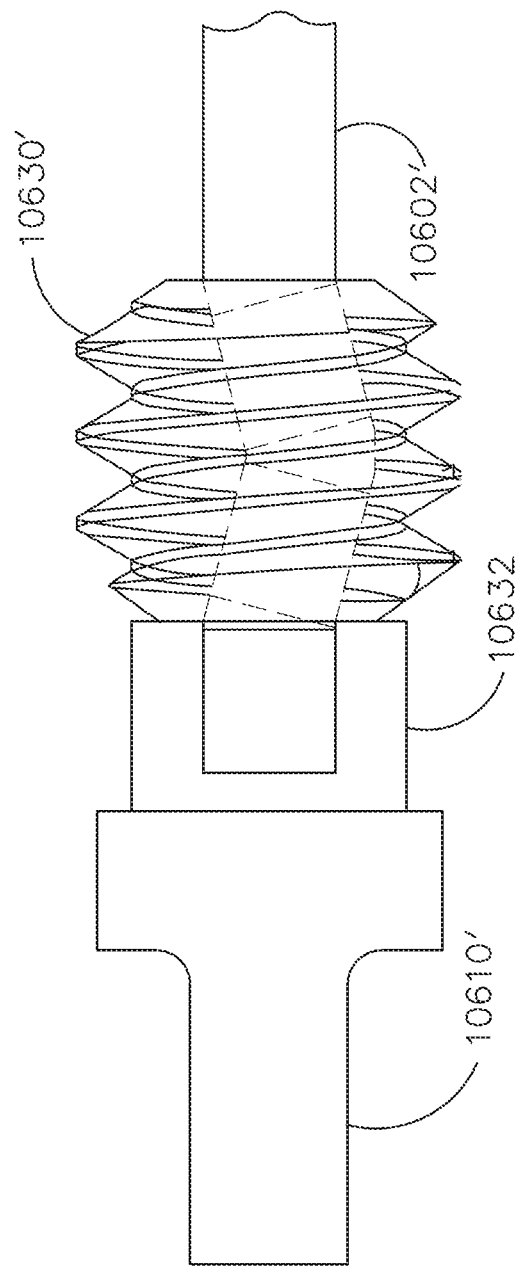
FIG. 30 is a top view of a portion of a rotary drive shaft, an actuation yoke assembly, and a threaded insert embodiment with portions of the rotary drive shaft shown in phantom, in accordance with at least one aspect of the present disclosure.
Figure 31:
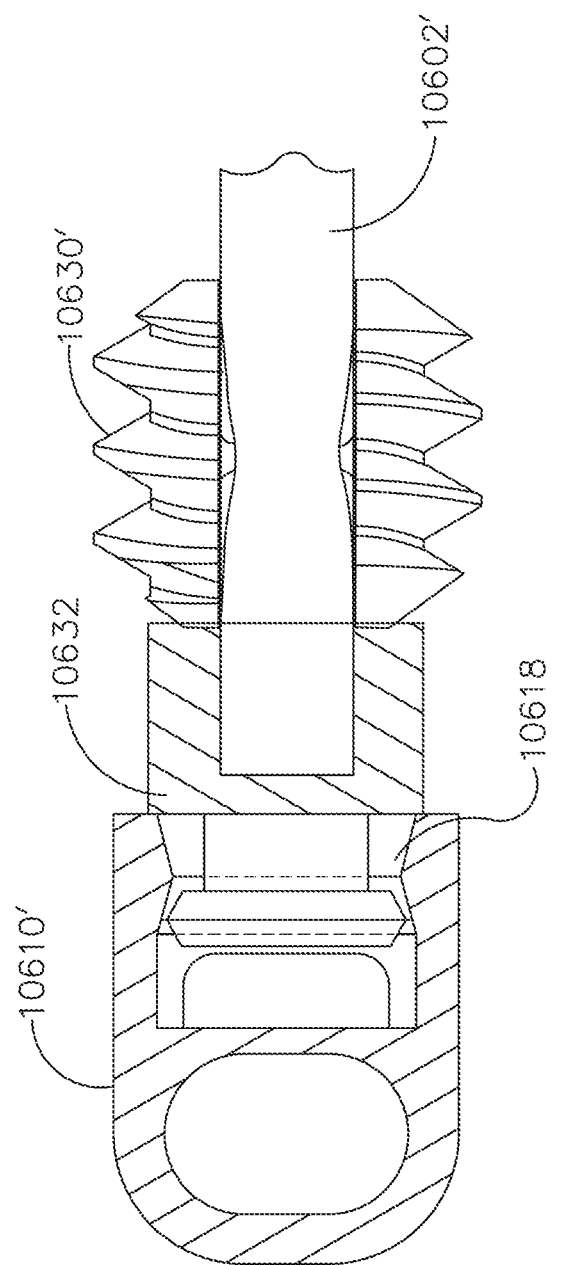
FIG. 31 is a side elevational view of the rotary drive shaft, actuation yoke assembly and threaded insert of FIG. 30.

FIGS. 30 and 31 illustrate an alternative actuator yoke 10610' that is rotatably attached to a flexible rotary drive shaft 10602'. In one arrangement, the flexible rotary drive shaft 10602' comprises a torque cable that has a diameter of approximately 0.039 inches. In certain instances, the threaded member 10630' comprises a coupler portion 10632 that is configured to be snapped into a cavity 10618 in an actuator yoke 10610'. When the coupler portion 10632 is attached to the actuator yoke 10610', the coupler portion 10632 is rotatable relative to the actuator yoke 10610'. Thus, rotation of the flexible rotary drive shaft 10602' and the threaded member 10630' will not cause the actuator yoke 10610' to rotate. The actuator yoke 10610' otherwise operates in the manner described above.

Figure 32:
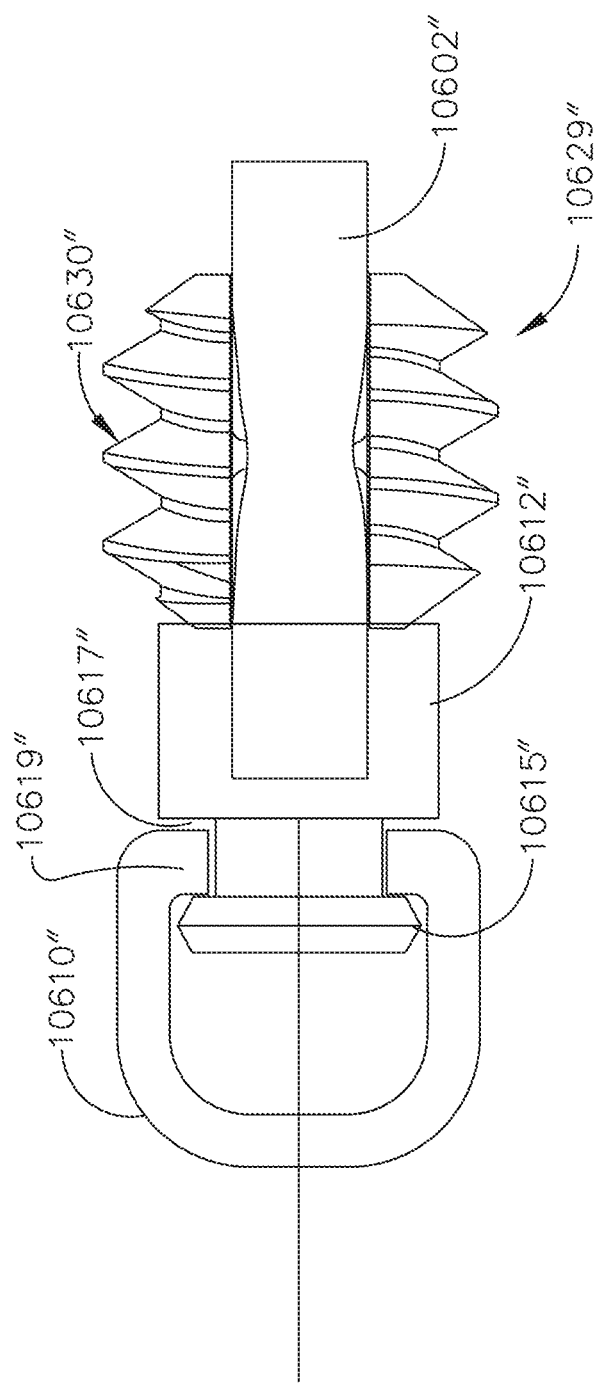
FIG. 32 is a side elevational view of a portion of another rotary drive shaft, another actuation yoke assembly, and another threaded insert embodiment, in accordance with at least one aspect of the present disclosure.
Figure 33:
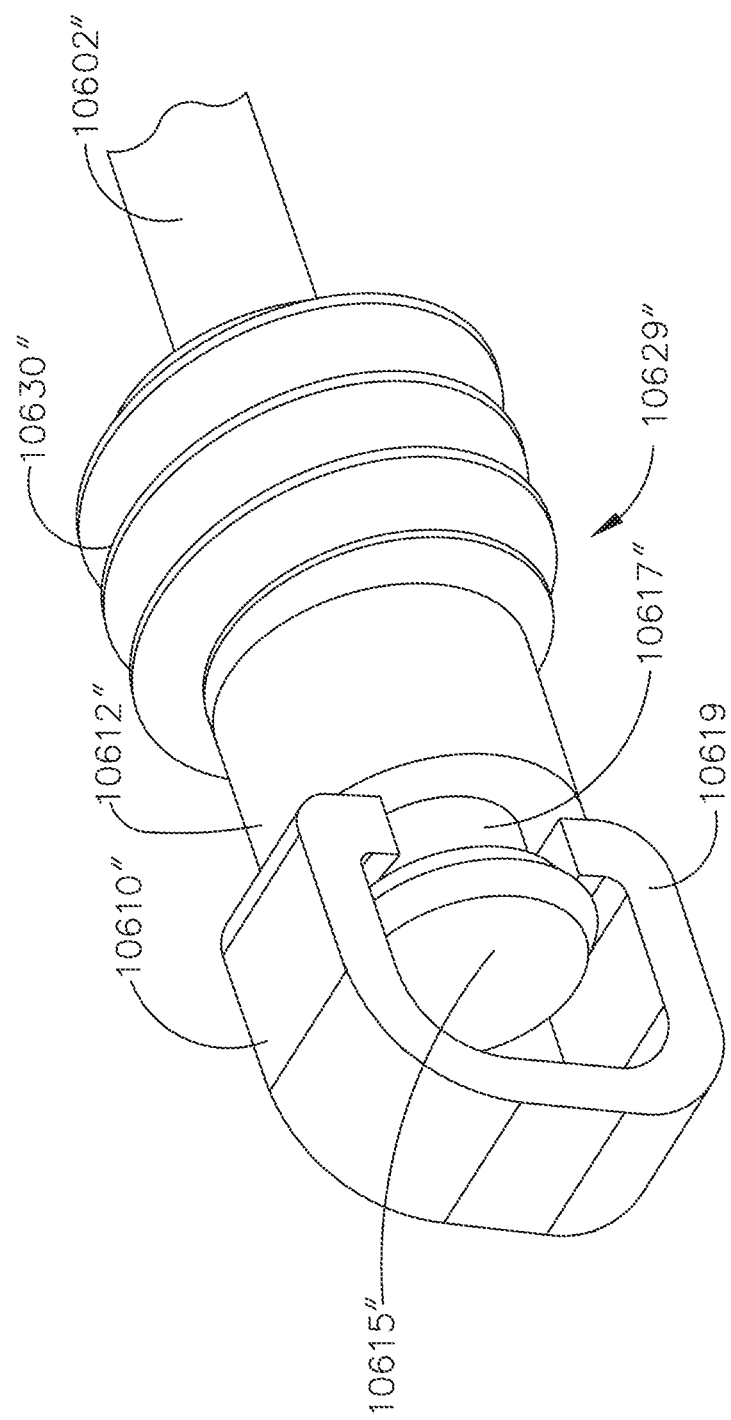
FIG. 33 is a perspective view of the rotary drive shaft, actuation yoke assembly, and threaded insert of FIG. 32.
Figure 37:
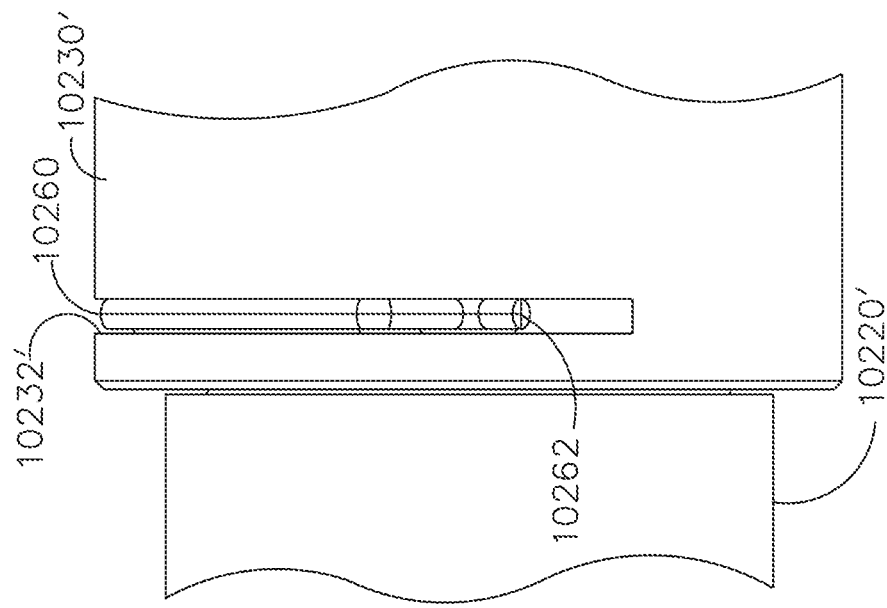
FIG. 37 is a side elevational view of a portion of the distal frame member and proximal housing member of FIG. 34.

FIGS. 32 and 33 illustrates another actuator yoke 10610" that is rotatable relative to the flexible rotary drive shaft 10602". In this arrangement, the distal end of the flexible rotary drive shaft 10602" is inserted into an insert assembly 10629" that comprises a threaded member 10630" and a proximal yoke portion 10612" that has a retainer head 10615" formed thereon that defines an annular yoke groove 10617". The insert assembly 10629" may be molded onto or crimped onto the distal end of the rotary drive shaft 10602". As can be seen in FIGS. 32 and 33, the actuator yoke 10610" comprises a clip 10619 that extends into the yoke groove 10617". Such arrangement facilitates relative rotation between the actuator yoke 10610" and the insert assembly 10629". The actuator yoke 10610" that may otherwise operate in the manners described above.

Figure 36:
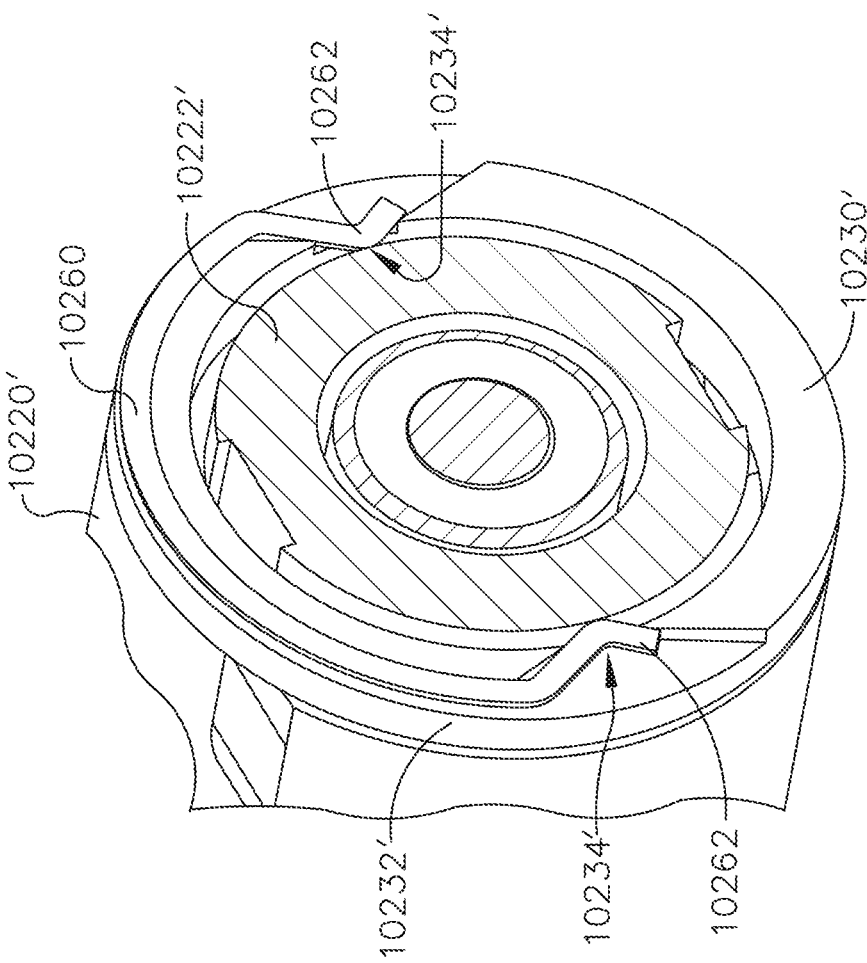
FIG. 36 is a cross-sectional end view of the distal frame member and proximal housing member of FIG. 34.

FIGS. 34-37 illustrate an alternative arrangement for rotatably supporting a proximal barrel portion 10222' of a distal frame member 10220' within a proximal frame housing 10230'. As can be seen in FIGS. 34-36, a spring clip 10260 is received within a clip groove 10232' that is provided in a portion of the perimeter of the proximal frame housing 10230'. The clip groove 10232' opens into a pair of diametrically-opposed clip notches 10234' that are configured to receive portions of clip ends 10262 of the spring clip 10260 therein. The clip ends 10262 ride on the outer perimeter of the proximal barrel portion 10222' to rotatably support the proximal barrel portion 10222' within the proximal frame housing 10230'. Such arrangement may also serve to reduce the amount of rotary friction between the proximal frame housing 10230' and the proximal barrel portion 10222'.

Figure 38:
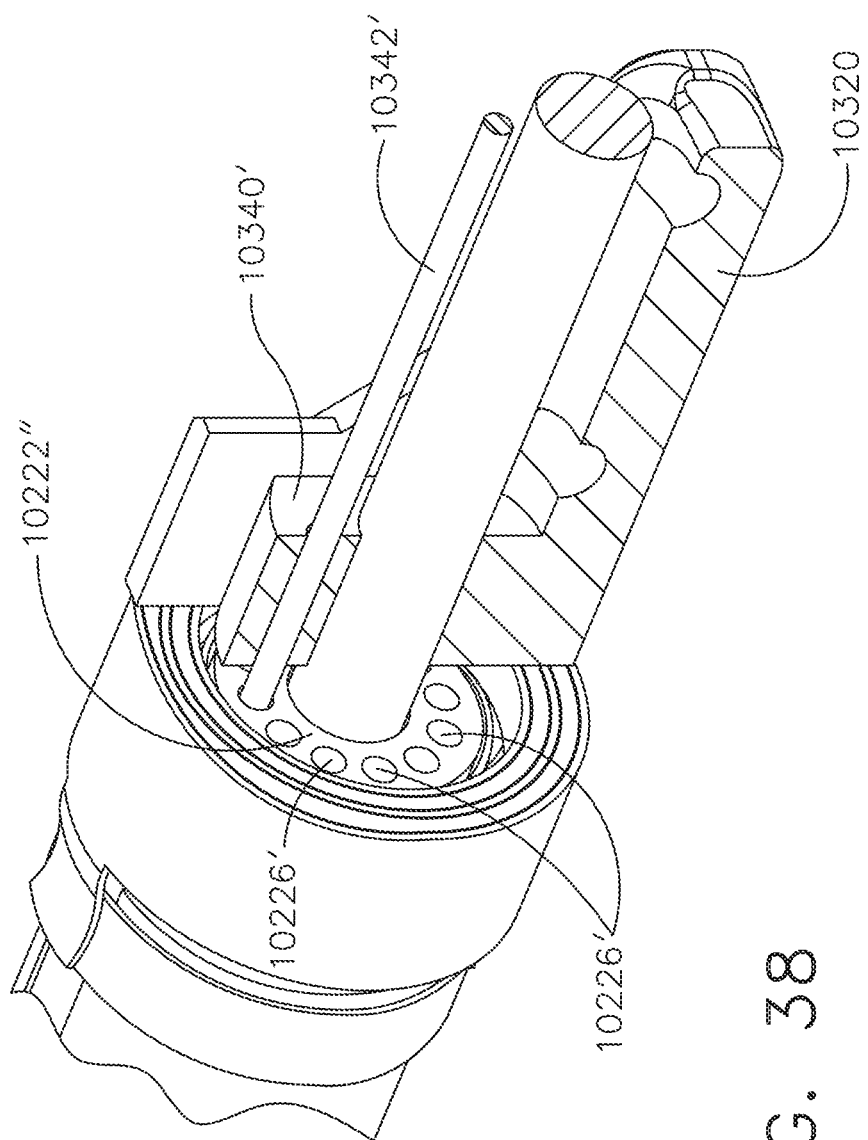
FIG. 38 is a partial cross-sectional perspective view of a portion of another surgical instrument, in accordance with at least one aspect of the present disclosure.

FIG. 38 illustrates an alternative proximal barrel portion 10222" and a locking cable arrangement 10342'. In the example illustrated in FIGS. 38 and 39, a proximal end of the proximal barrel portion 10222" includes a plurality of radially arranged locking cavities 10226' therein that are configured to be lockingly engaged by the locking cable or locking member 10342' in the manner described above. In this arrangement, a flexible locking cable or locking member 10342' is attached to a lock insert 10340' that is slidably supported in the proximal effector frame member 10320. See FIG. 38. A distal end of the locking cable or locking member 10342' protrudes distally out of the locking insert 10340' which is biased distally into a locking position by a spring (not shown). The flexible unlocking cable or unlocking member 10342' extends through the proximal shaft segment 10100 to interface with a control system in the housing. For example, in certain instances, the flexible unlocking cable or unlocking member 10342' may interface with a motor or other control arrangement to selectively pull the unlocking cable or unlocking member 10342' proximally to move the distal end of the unlocking cable or unlocking member 10342' out of locking engagement with the locking cavities 10226' on the proximal barrel portion 10222".

Figure 39:
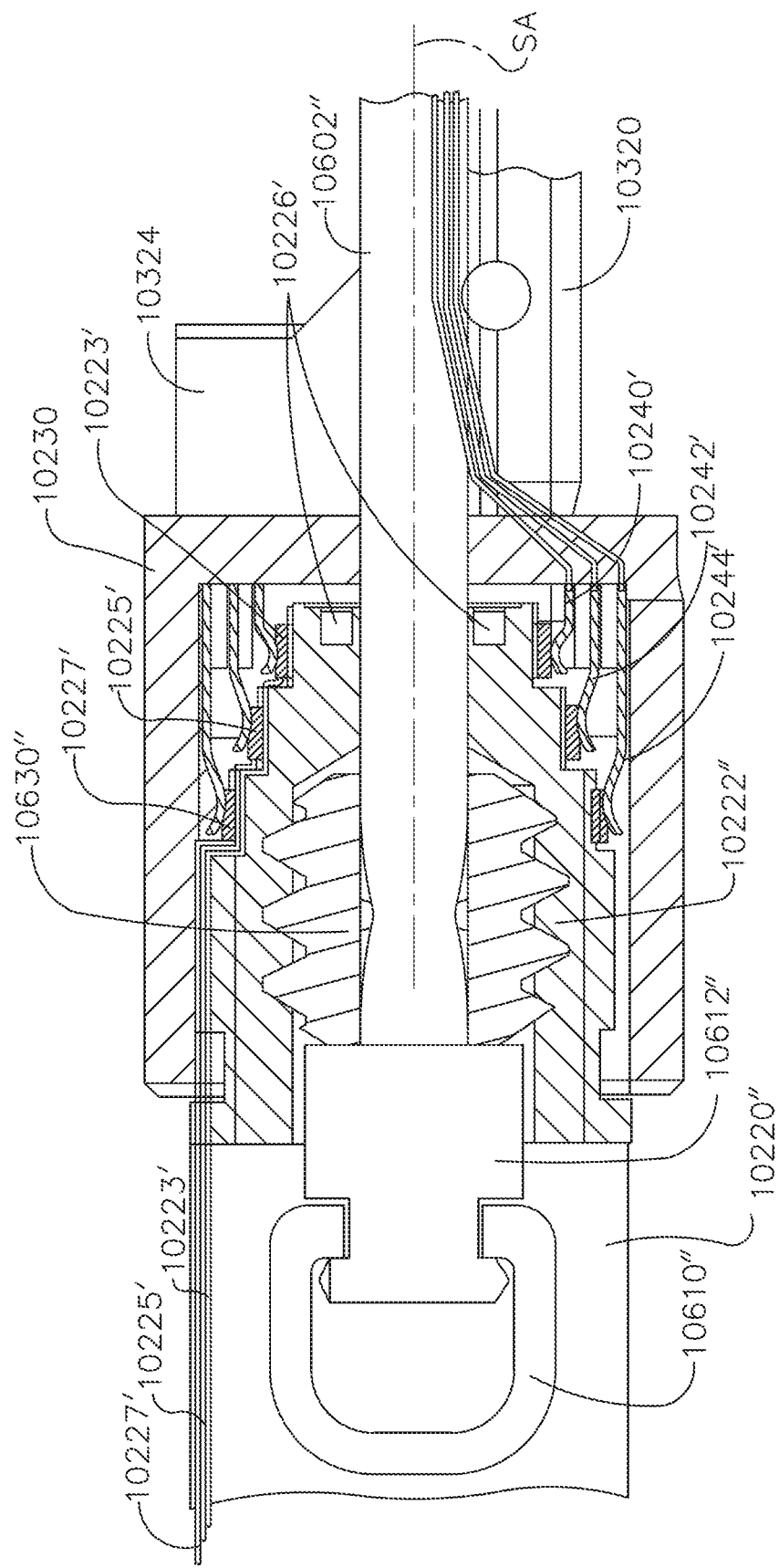
FIG. 39 is a cross-sectional side view of a portion of the surgical instrument of FIG. 38.
Figure 40:
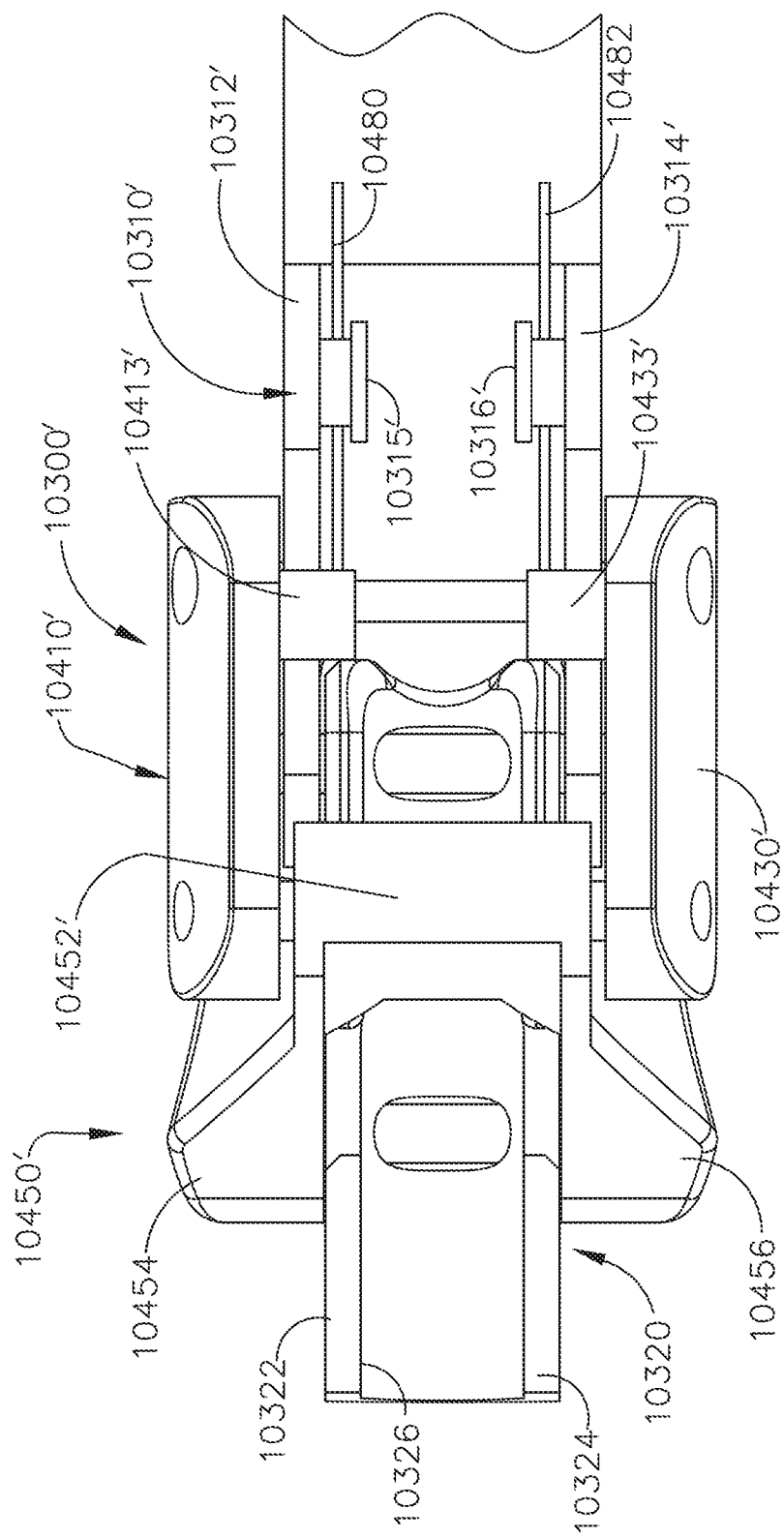
FIG. 40 is a top view of a portion of another articulation joint embodiment in an unarticulated position, in accordance with at least one aspect of the present disclosure.

As can be seen in FIG. 39, in this example, three fixed contacts 10240', 10242', 10244' are mounted in a proximal frame housing 10230'. An annular contact 10223' is supported around a stepped portion of the perimeter of the proximal barrel portion 10222" of the distal frame member 10220"'. The fixed contact 10240' is in contact with the annular contact 10223' as the distal frame member 10220" is rotated about the shaft axis SA. An annular contact 10225' is supported around the stepped perimeter of the proximal barrel portion 10222" of the distal frame member 10220". The fixed contact 10242' is in contact with the annular contact 10225' as the distal frame member 10220" is rotated about the shaft axis SA. An annular contact 10227' is supported around the stepped perimeter of the proximal barrel portion 10222" of the distal frame member 10220". The fixed contact 10244' is in contact with as the annular contact 10227' as the distal frame member 10220" is rotated about the shaft axis SA. In various instances, the contacts 10240', 10242', 10244' may also extend into one or both of the first and second jaws 10250, 10270 to transmit signals/power thereto. Such arrangement facilitates transfer of electrical power/signals between the housing and the surgical end effector 10200 while facilitating articulation and rotation of the surgical end effector 10200 relative to the proximal shaft segment 10100.

FIGS. 40-44 illustrate an alternative articulation joint 10300' that is actuated by a right articulation actuation cable or push rod 10480 and a left articulation actuation cable or push rod 10482. In various instances, the cables/push rods 10480, 10482 must be sufficiently rigid so as to be capable of applying a pushing motion to the articulation joint yet be flexible enough to accommodate full joint articulation. These cables/push rods may be configured to move in opposite directions during articulation of the end effector. In other instances, the cables may be completely flexible such that articulation is accomplished by pulling on one of the cables and allowing the opposing cable to travel with the articulation joint to accommodate the articulation. To return the end effector to an unarticulated position, the opposing cable is pulled and the first cable is permitted to travel with the joint to the unarticulated position.

Figure 41:
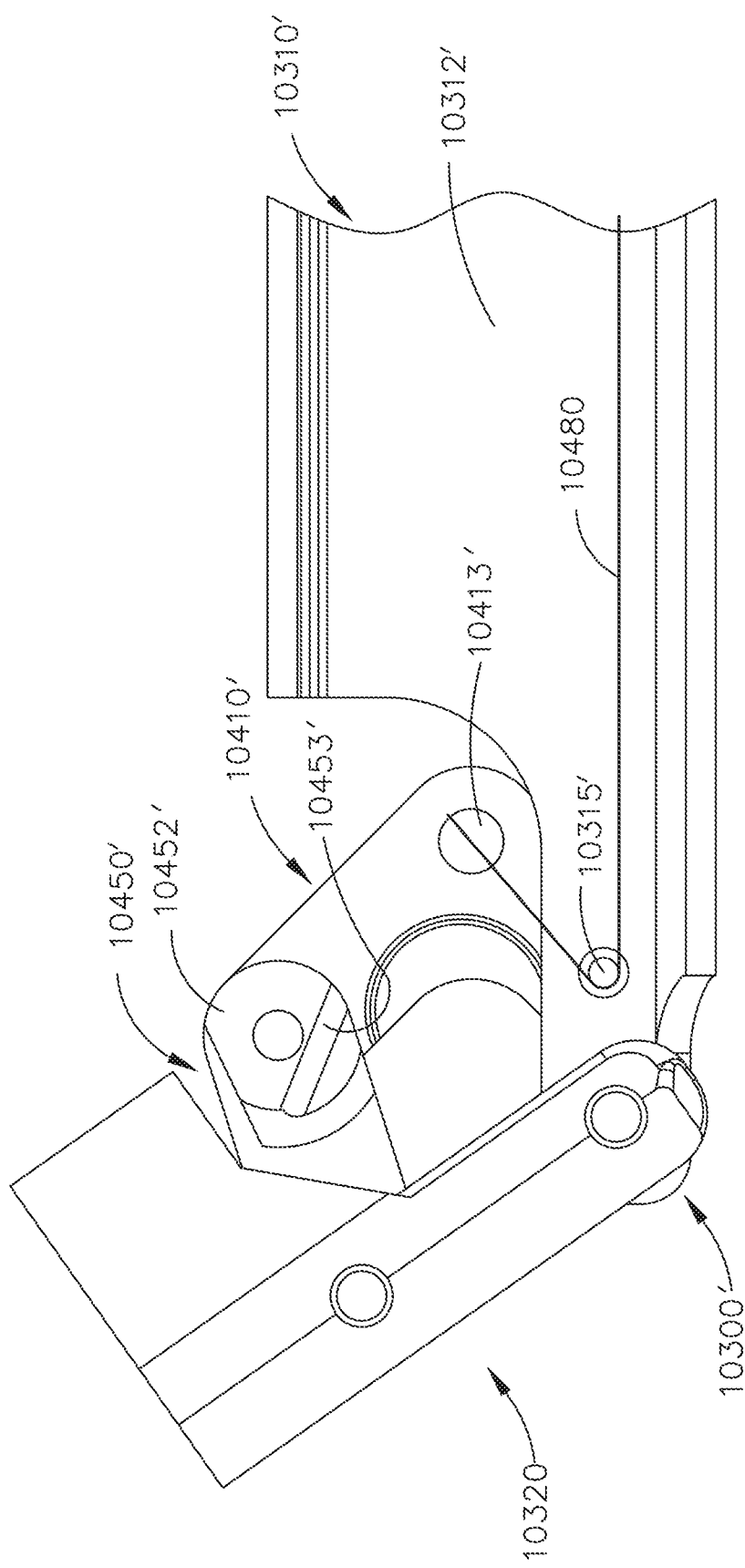
FIG. 41 is a partial cross-sectional side view of the articulation joint of FIG. 40 articulated in a first direction.
Figure 42:
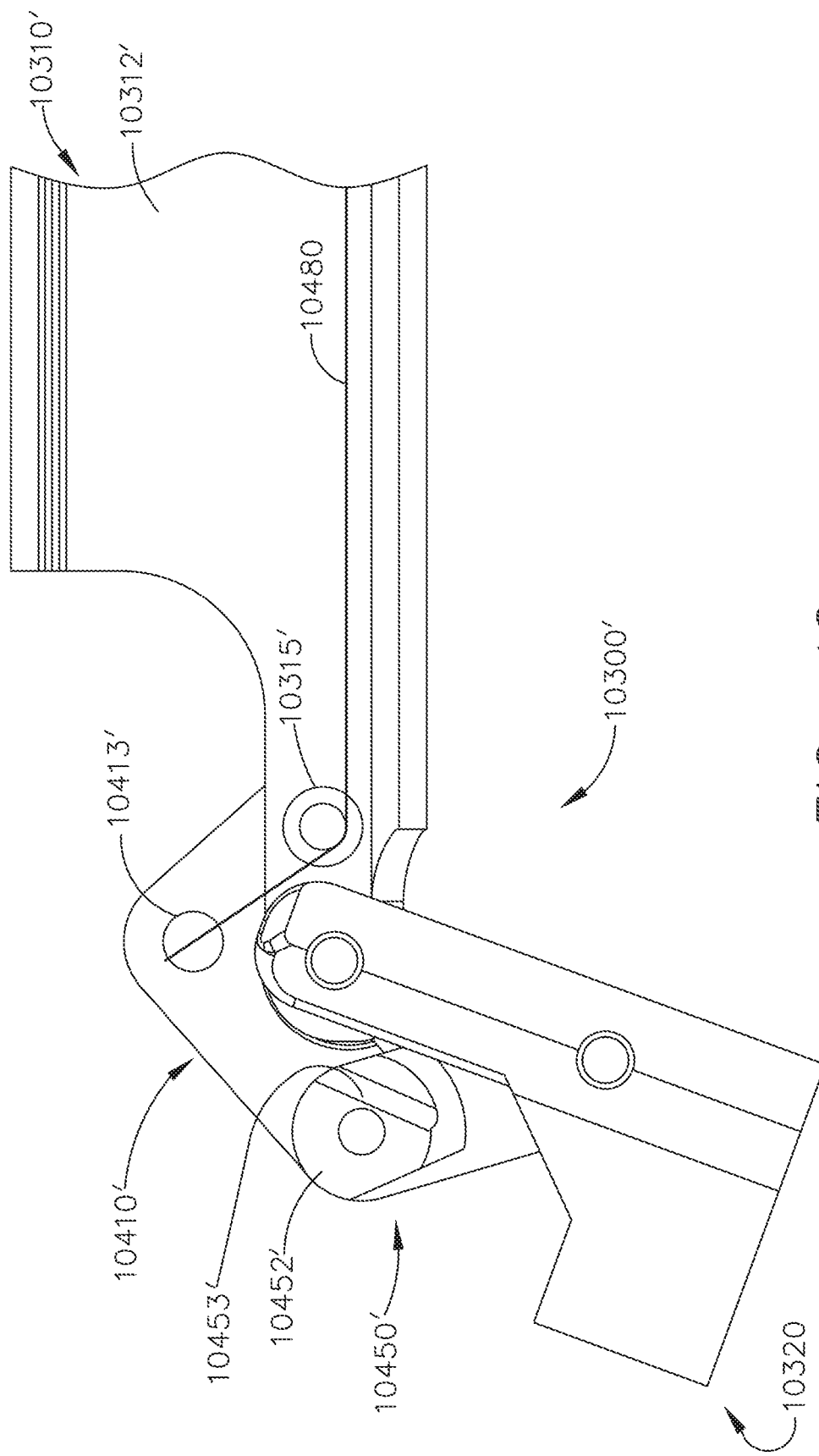
FIG. 42 is another partial cross-sectional side view of the articulation joint of FIG. 40 articulated in a second direction.
Figure 43:
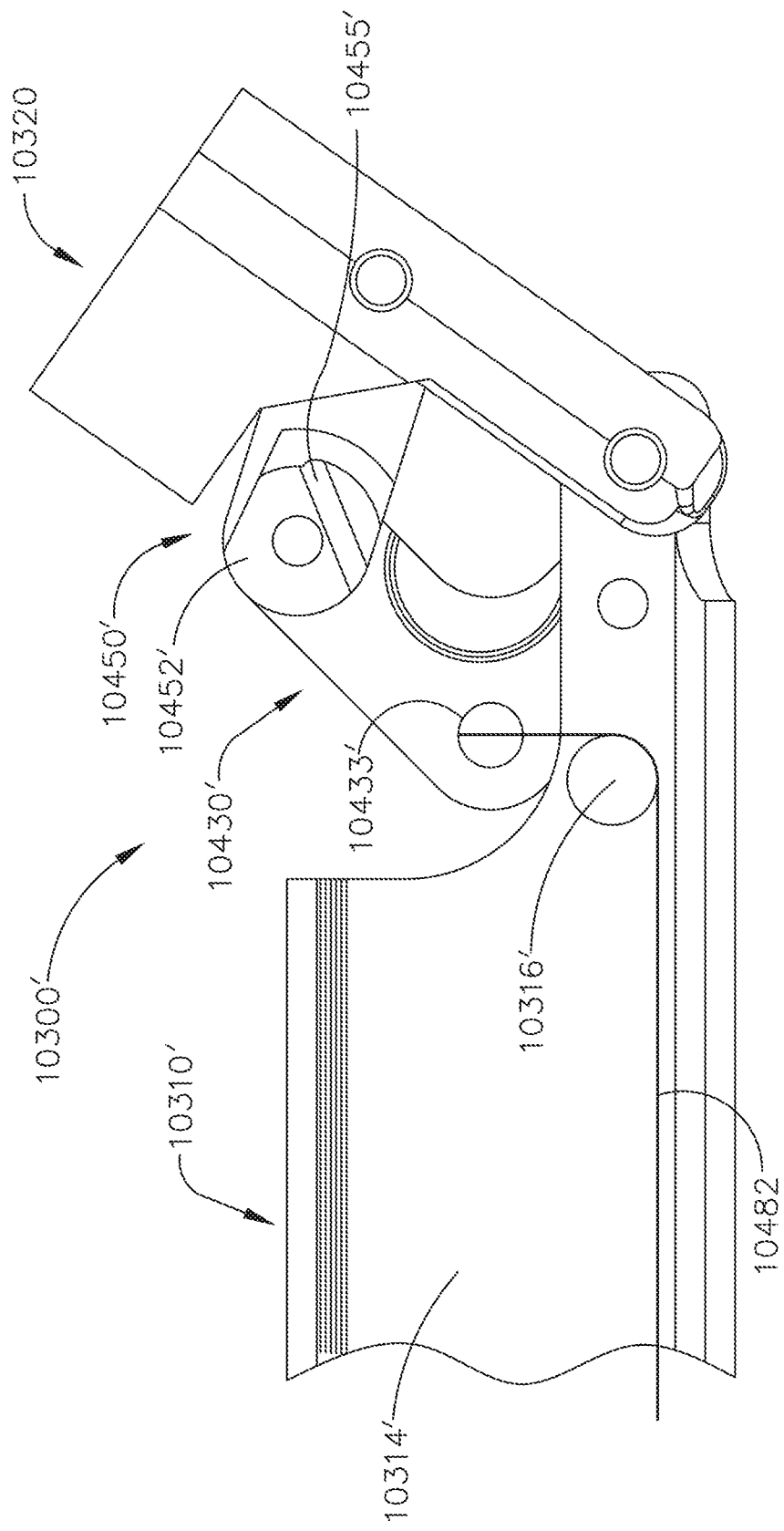
FIG. 43 is another partial cross-sectional side view of the articulation joint of FIG. 40 articulated in a first direction.
Figure 44:
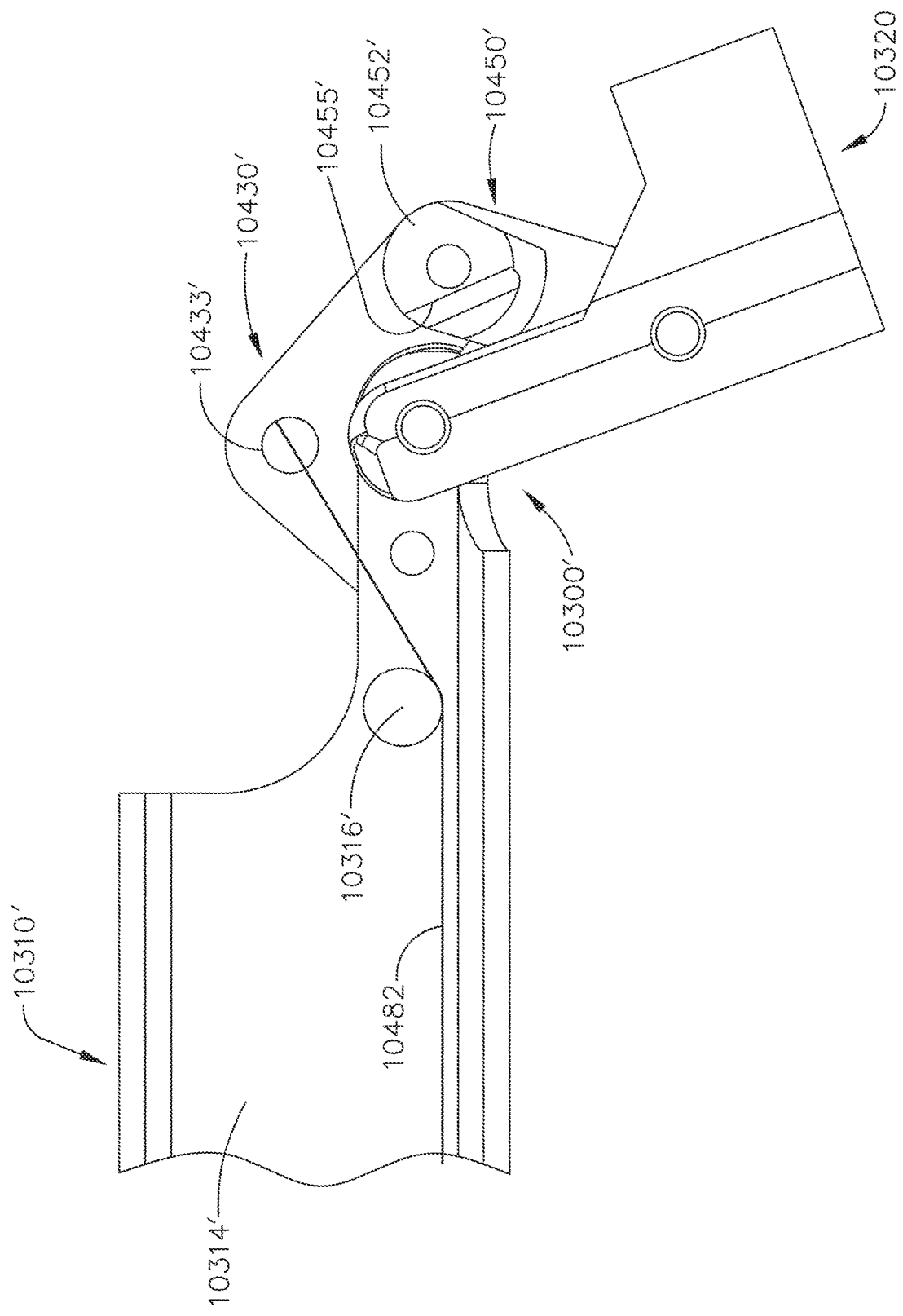
FIG. 44 is another partial cross-sectional side view of the articulation joint of FIG. 40 articulated in a second direction.
Figure 45:
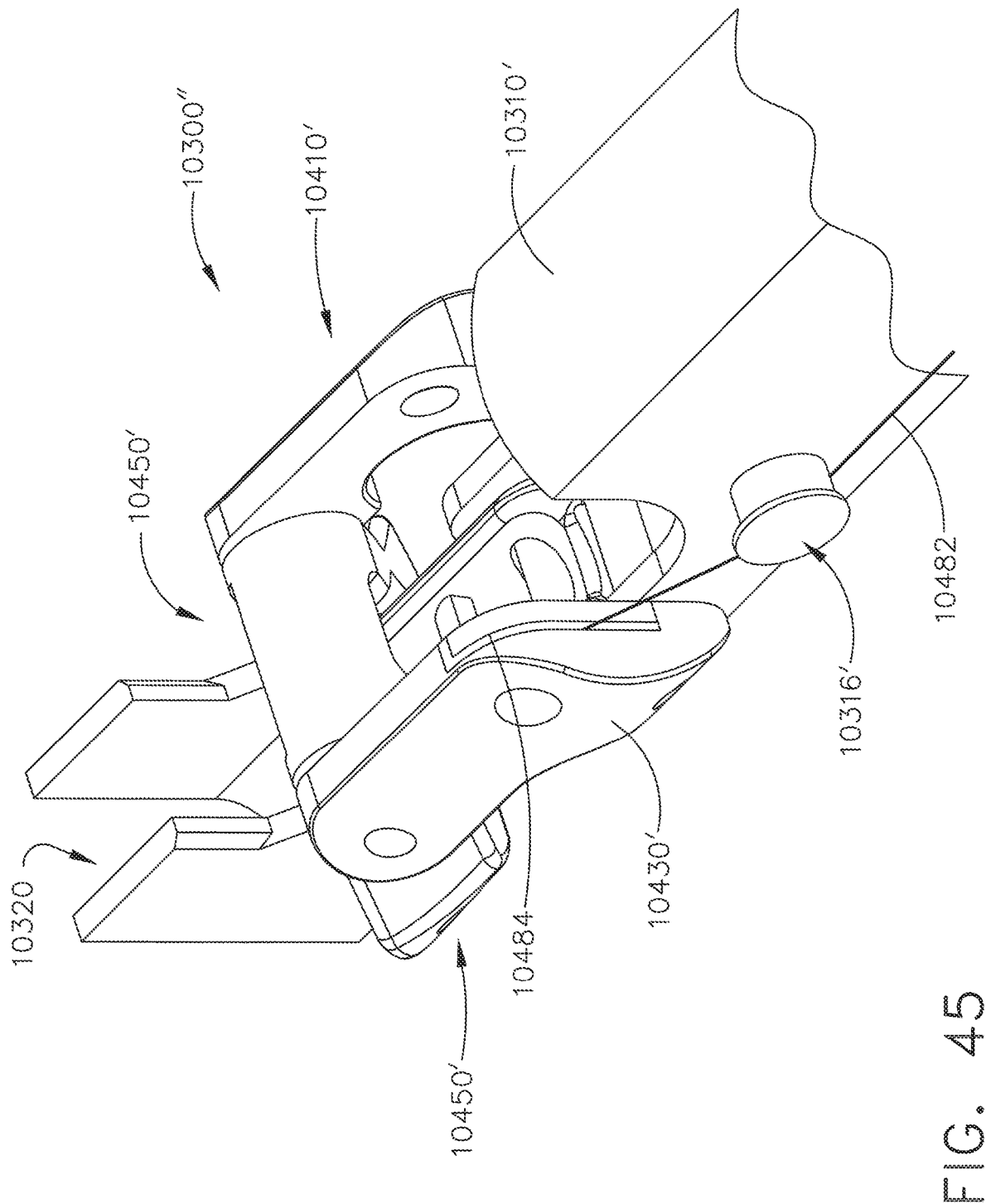
FIG. 45 is a partial perspective view of a portion of another articulation joint embodiment, in accordance with at least one aspect of the present disclosure.
Figure 46:
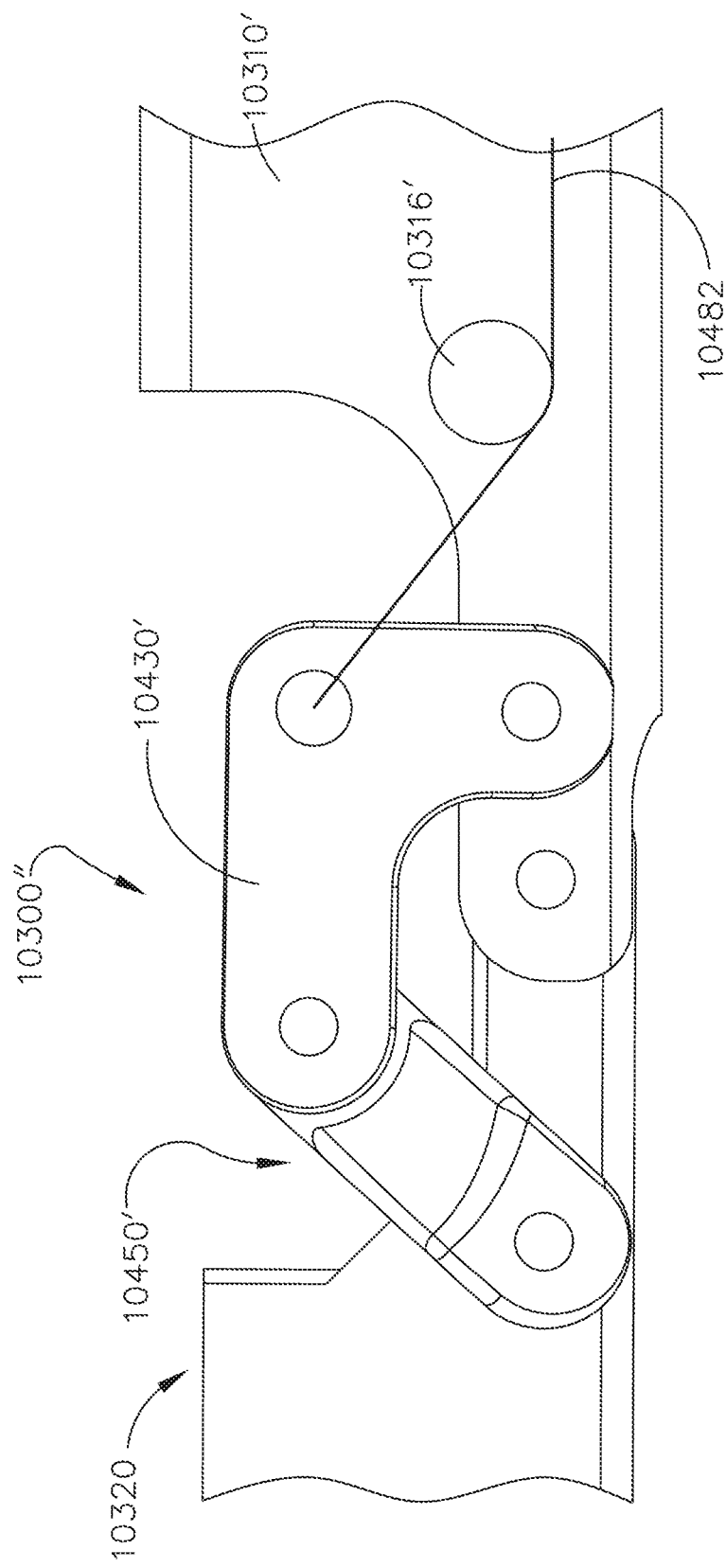
FIG. 46 is a side elevational view of the articulation joint of FIG. 45 in an unarticulated position.

The right articulation actuation cable 10480 extends through the proximal shaft frame 10310' and the proximal outer shaft tube (not shown). The right articulation cable 10480 is attached to the right articulation rib segment 10413' that protrudes from the right proximal link 10410'. The left articulation cable 10482 extends through the proximal shaft frame 10310' that has proximally extending attachment arms 10312', 10314' and is attached to the left articulation rib 10433' that protrudes from the left proximal link 10430'. The right articulation cable 10480 extends around a right support member 10315' that protrudes inward from the attachment arm 10312' and the left articulation actuation cable 10482 extends around a left support member 10316' that protrudes inwardly from the attachment arm 10314'. In various instances, the right articulation actuation cable 10480 and the left articulation actuation cable 10482 may be controlled by a motor-controlled drum or other control arrangement that is/are supported by the housing, for example. As can be seen in FIG. 41, a right clearance groove 10453' is provided in the second link proximal end 10452' of the centrally disposed second link 10450' to accommodate the right articulation actuation cable 10480 during articulation. Likewise, a left clearance groove 10455' is also provided in the second link proximal end 10452' of the centrally disposed second link 10450' to accommodate the left articulation actuation cable 10482 during articulation. See FIG. 42. FIGS. 42-44 illustrate articulation of the articulation joint 10300' using the cables 10480, 10482. FIGS. 45 and 46 illustrate an alternative articulation joint 10300" wherein the left articulation actuation cable 10482 is routed on the outside of the proximal shaft frame 10310' and is received within a clearance groove 10484 in the left proximal link 10430' and is attached thereto. This embodiment only employs one articulation actuation cable 10482, but a right articulation cable (not shown) could also be employed.

Figure 47:
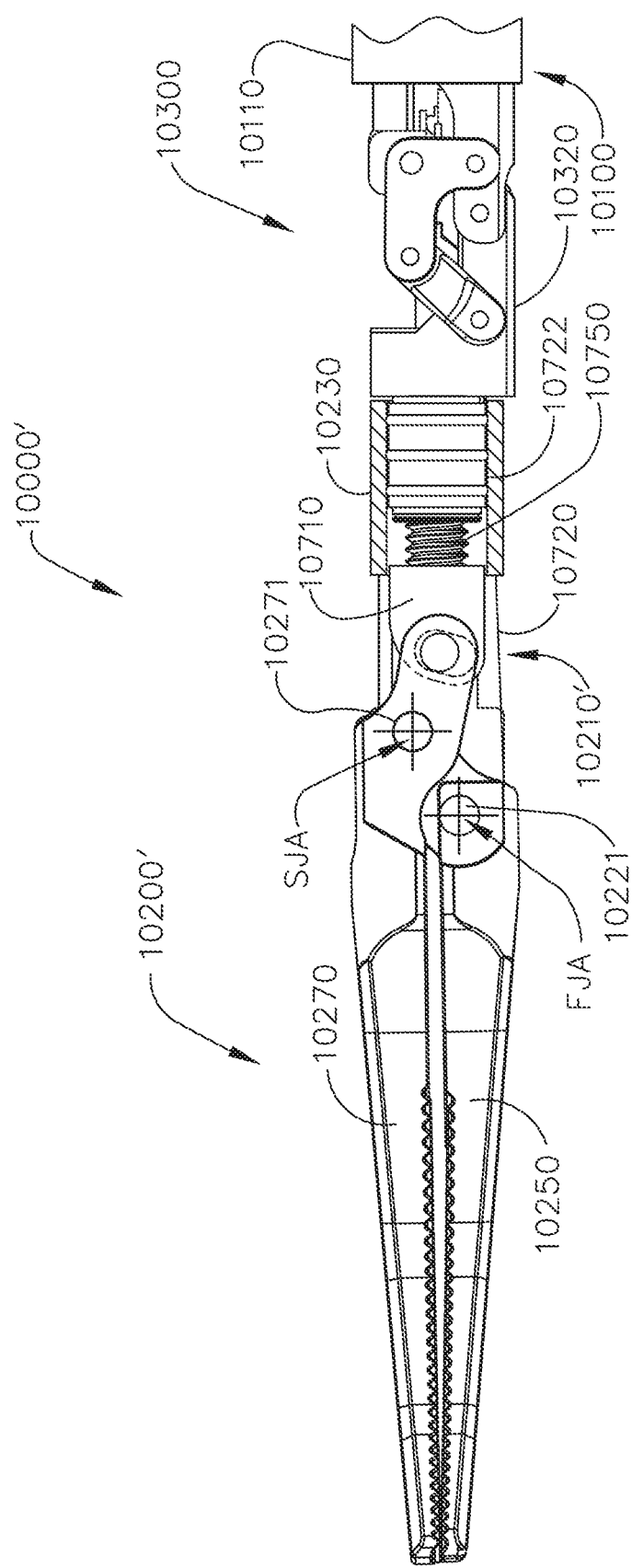
FIG. 47 is a side view of a portion of another surgical instrument with a surgical end effector thereof in an unarticulated position and jaws thereof in a closed position with portions thereof shown in phantom, in accordance with at least one aspect of the present disclosure.
Figure 48:
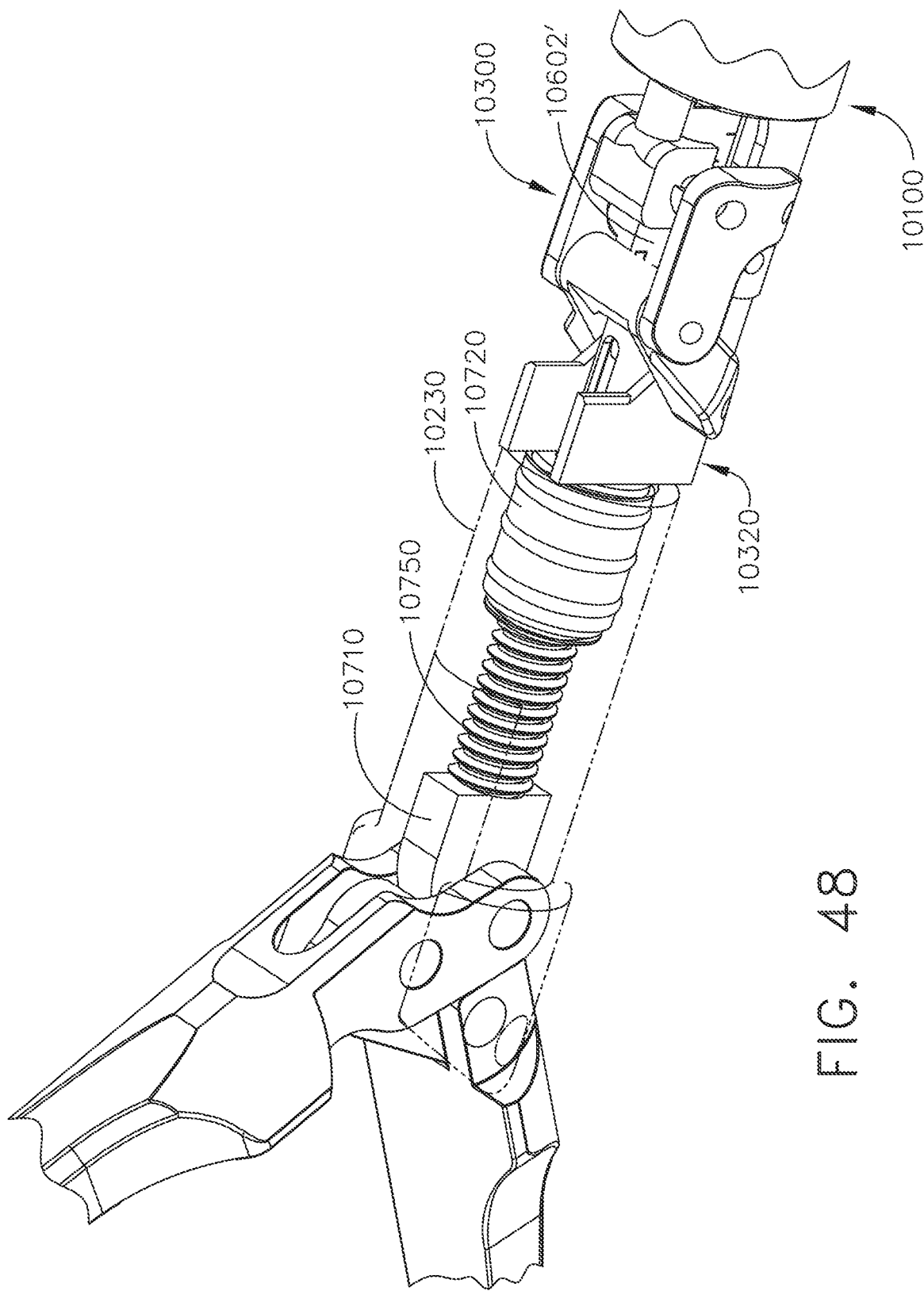
FIG. 48 is a partial perspective view of a portion of the surgical instrument of FIG. 47 with some elements thereof shown in phantom.
Figure 49:
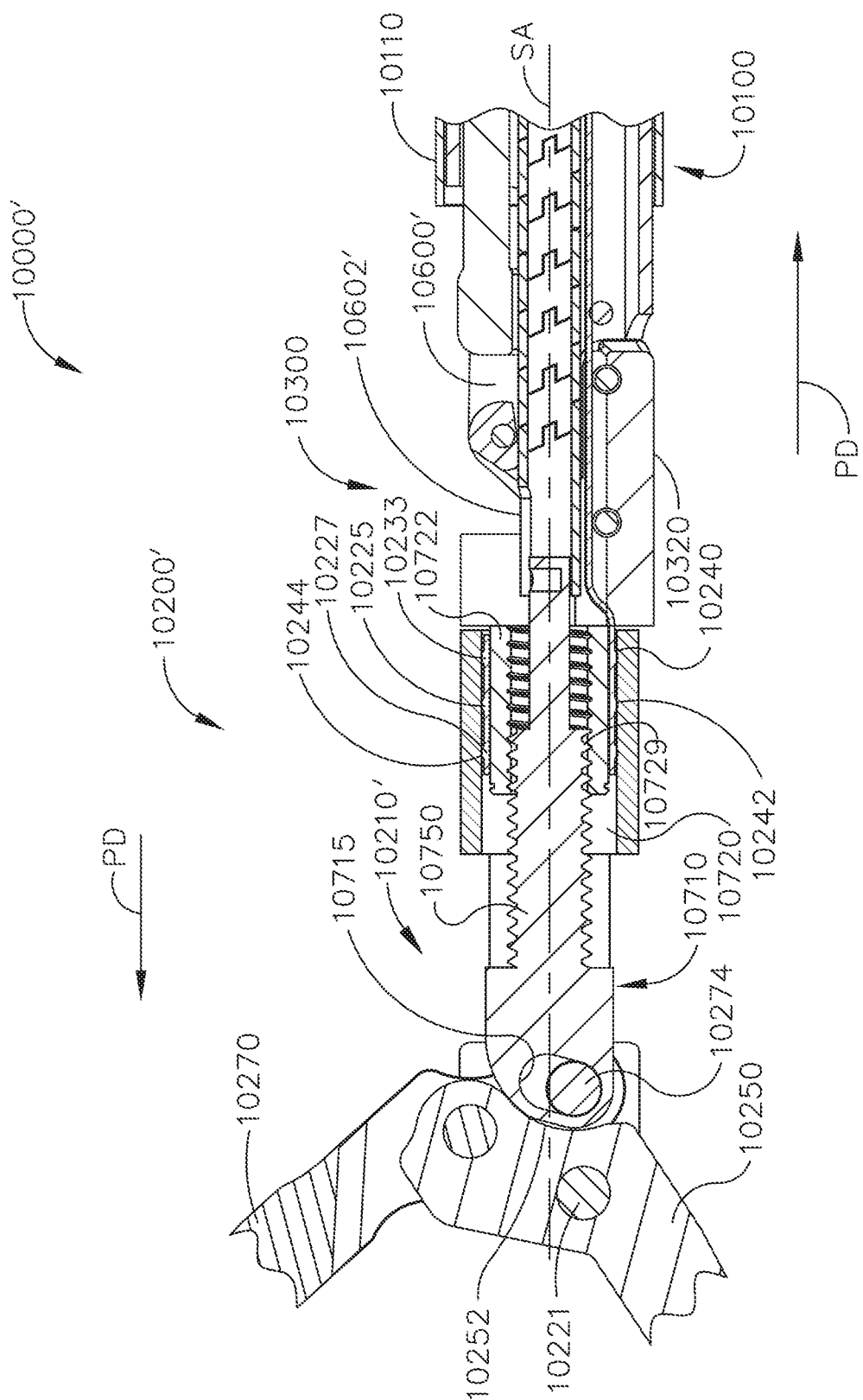
FIG. 49 is a cross-sectional side view of a portion of the surgical instrument of FIG. 47 with the jaws thereof in an open position.

FIGS. 47-49 illustrate another surgical instrument 10000' that comprises a surgical end effector 10200'. In various instances, surgical end effector 10200' may be identical to surgical end effector 10200 except for the differences discussed below. The surgical end effector 10200' comprises an end effector frame assembly 10210' that comprises a distal frame member 10720 that is rotatably supported in a proximal frame housing 10230. The proximal frame housing 10230 is fixedly attached to the proximal end effector frame member 10320. For example, the proximal frame housing 10230 may be attached to the proximal end effector frame member 10320 by welding, adhesive, etc. In the illustrated example, the distal frame member 10720 is non-rotatably attached to a proximal barrel member 10722 that is configured to rotate within proximal frame housing 10230 as will be discussed in further detail below. A distal end of the proximal barrel member 10722 comprises a plurality of radial grooves or recesses therein that are configured to be lockingly engaged by a locking insert (not shown) and/or an unlocking cable (not shown) in the various manners described herein.

In the illustrated example, the first jaw 10250 is pivotally pinned to the distal frame member 10720 for selective pivotal travel relative thereto about a first jaw axis FJA defined by a first jaw pin 10221. The second jaw 10270 is pivotally pinned to the first jaw 10250 for selective pivotal travel relative to the first jaw 10250 about a second jaw axis SJA that is defined by a second jaw pin 10271. In the illustrated example, the surgical end effector 10200' employs actuator yoke assembly 10710 that differs in some aspects from actuator yoke assembly 10610. In the illustrated example, the actuator yoke assembly 10710 comprises an elongate slot 10715 that facilitates vertical movement of the second jaw attachment pin 10274 therein. See FIG. 50. The cam surface 10252 of the first jaw 10250 is configured to cammingly interact with the actuator yoke assembly 10710 when the actuator yoke assembly 10710 is driven distally to cam the first jaw 10250 into an open position about the first jaw pin 10221.

In certain instances, an end effector drive member 10600' comprises a flexible rotary shaft 10602' that is capable of rotation while maintaining an ability to bend and flex to accommodate articulation of the surgical end effector 10200' in the manners described herein. In various instances, the flexible rotary shaft 10602' operably interfaces with a motor or other source of rotary motion supported in the housing and comprises a laser-cut hollow tube that is capable of flexing or bending to accommodate articulation of the surgical end effector 10200'. As can be see FIG. 49, a threaded shaft member 10750 protrudes proximally from the actuator yoke assembly 10710 and is threadably received within a threaded passage 10729 in the proximal barrel member 10722 and is coupled to the flexible rotary shaft 10602'. The threaded shaft member 10750 is rotatably coupled to the actuator yoke assembly 10710 to enable the threaded shaft member 10750 to rotate relative to the actuator yoke 10710 assembly while remaining attached thereto, as described herein.

In certain instances, the first and second jaws 10250, 10270 are opened and closed as follows. To open and close the jaws 10250, 10270, as was discussed in detail above, the lock insert is in locking engagement with the proximal barrel member 10722 to prevent the rotation thereof. Thereafter, rotation of the rotary drive shaft 10602' in a first direction will rotate the threaded shaft member 10750 within the threaded bore or passage 10729 in the proximal barrel member 10722 and drive the actuator yoke assembly 10710 in the distal direction DD to move the first jaw 10250 and the second jaw 10270 toward an open position. Because the locking insert is in locking engagement with the proximal barrel member 10722, the surgical end effector 10200' is prevented from rotating about the shaft axis SA when the rotary flexible drive shaft 10602' is rotated. Thus, rotation of the rotary drive shaft 10602' in a first direction will axially drive the actuator yoke 10710 distally when the locking insert is in locking engagement with the proximal barrel member 10722. Rotation of the rotary drive shaft 10602' in a second direction opposite the first direction will axially drive the actuator yoke 10710 proximally and pull the jaws 10250, 10270 toward a closed position.

To rotate the surgical end effector 10200' about the shaft axis SA, the unlocking cable is pulled proximally to cause the locking insert to disengage the lock grooves in the proximal barrel member 10722. Thereafter, the flexible rotary drive shaft 10602' is rotated in a desired direction. In such instance, there is enough friction between the threaded shaft 10750 and the internal threads 10729 defined in the proximal barrel member 10722 such that rotation of the threaded shaft 10750 will cause the proximal barrel portion 10722 (and the surgical end effector 10200') to rotate about the shaft axis SA.

In certain instances to facilitate transfer of electric signals/power from a housing to the surgical end effector 10200' and more particularly to one or both of the first and second jaws 10250, 10270, conductors may be provided through the proximal shaft segment 10100 and span the articulation joint 10300 to terminate in a series of contacts supported in the proximal frame housing 10230. In various instances, three fixed contacts 10240, 10242, 10244 are mounted in the proximal frame housing 10230. See, e.g., FIG. 25. An annular contact 10223 is supported around the perimeter of the proximal barrel member 10722 of the distal frame member 10720. The fixed contact 10240 is configured to be in electrical contact with the annular contact 10223 as the distal frame member 10720 is rotated about the shaft axis SA. An annular contact 10225 is supported around the perimeter of the proximal barrel member 10722 of the distal frame member 10720. The fixed contact 10242 is configured to be in electrical contact with as the annular contact 10225 as the distal frame member 10720 is rotated about the shaft axis SA. An annular contact 10227 is supported around the perimeter of the proximal barrel member 10722 of the distal frame member 10720. The fixed contact 10244 is configured to be in electrical contact with the annular contact 10227 as the distal frame member 10720 is rotated about the shaft axis SA. The contacts 10240, 10242, 10244 may also extend into one or both of the first and second jaws 10250, 10270 to transmit signals/power thereto. Such arrangement facilitates transfer of electrical power/signals between the housing and the surgical end effector 10200' while facilitating articulation and rotation of the surgical end effector 10200' relative to the proximal shaft segment 10100.

Figure 50:
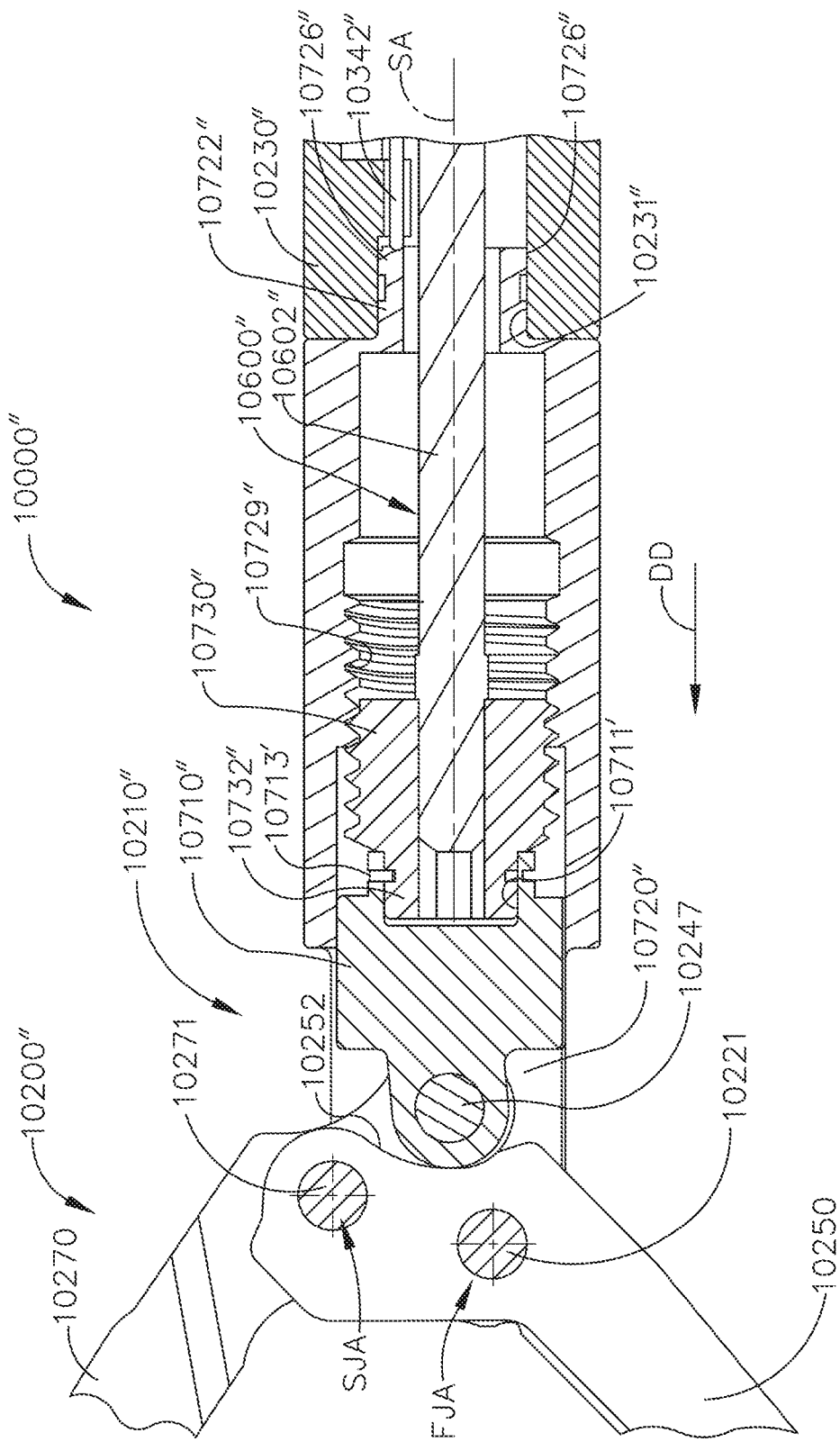
FIG. 50 is a partial cross-sectional view of another surgical instrument with the jaws thereof in an open position, in accordance with at least one aspect of the present disclosure.
Figure 51:
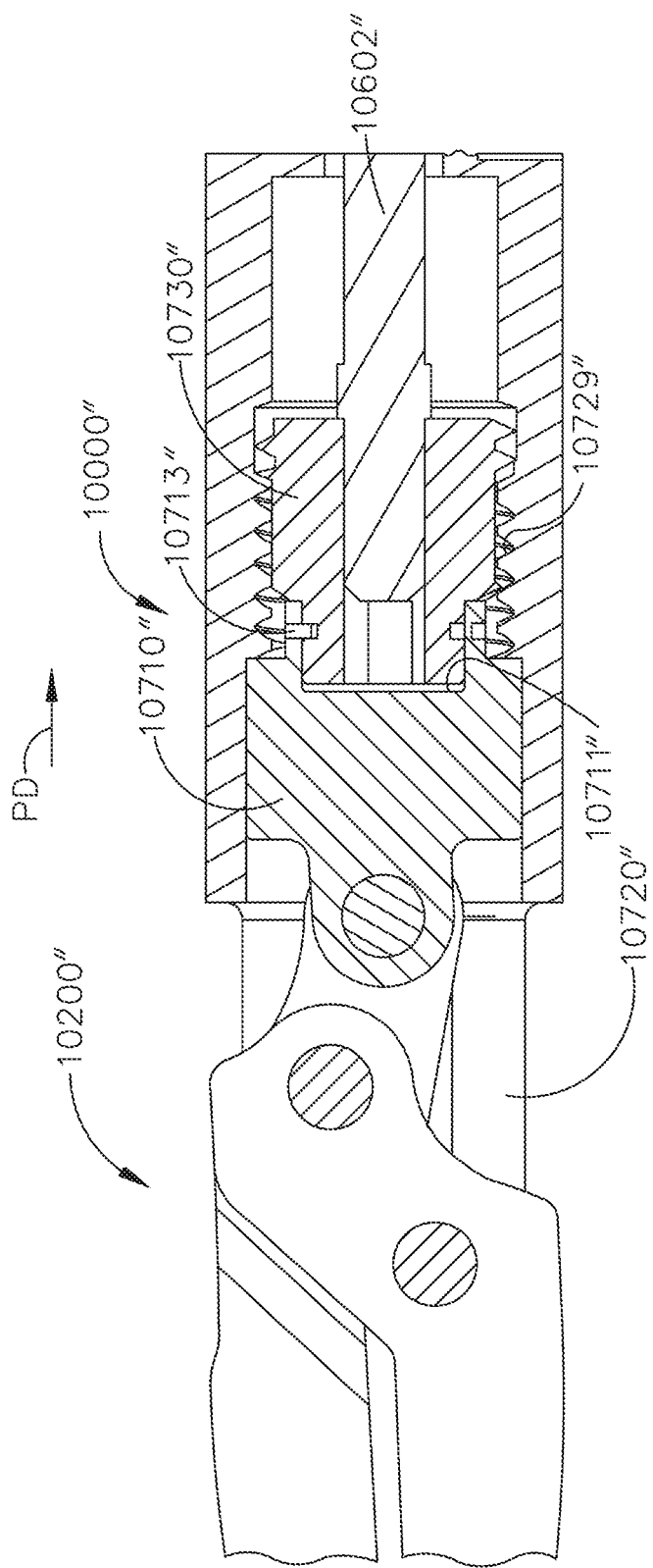
FIG. 51 is another partial cross-sectional view of the surgical instrument of FIG. 50 with the jaws thereof in a closed position.

FIGS. 50 and 51 illustrate another surgical instrument 10000" that comprises a surgical end effector 10200". In certain instances, surgical end effector 10200" is identical to surgical end effector 10200 except for the differences discussed below. The surgical end effector 10200" comprises an end effector frame assembly 10210" that comprises a distal frame member 10720". The distal frame member 10720" includes a proximally-extending proximal end portion 10722" that is rotatably supported within a bore 10231" in a proximal frame housing 10230". A plurality of recesses 10726" are provided in a proximal end of the proximal end portion 10722". In various instances, the recesses 10726" are adapted to be engaged by a flexible unlocking cable or unlocking rod 10342" in the various manners described herein. See FIG. 50.

Still referring to FIGS. 50 and 51, the surgical end effector comprises a first jaw 10250 and a second jaw 10270. The first jaw 10250 is pivotally pinned to the distal frame member 10720" for selective pivotal travel relative thereto about a first jaw axis FJA defined by a first jaw pin 10221. The second jaw 10270 is pivotally pinned to the first jaw 10250 for selective pivotal travel relative to the first jaw 10250 about a second jaw axis SJA that is defined by a second jaw pin 10271. In certain instances, the surgical end effector 10200" employs an actuator yoke assembly 10710" that differs in some aspects from actuator yoke assembly 10610. In the illustrated example, the actuator yoke assembly 10710" is pivotally coupled to the second jaw 10270 by a second jaw attachment pin 10274. The first jaw 10250 comprises a cam surface 10252 that is configured to cammingly interact with the actuator yoke assembly 10710" when the actuator yoke assembly 10710" is driven distally to cam the first jaw 10250 into an open position about the first jaw pin 10221.

The surgical instrument 10000" comprises an end effector drive member 10600". In certain instances, the end effector drive member 10600" comprises a flexible rotary shaft 10602" that is capable of rotation while being able to bend and flex to accommodate articulation of the surgical end effector 10200" in the manners described herein. In various instances, the flexible rotary shaft 10602" operably interfaces with a motor or other source of rotary motion supported in a housing, for example. As can be see in FIGS. 50 and 51, a threaded nut 10730" is fixedly attached to the flexible rotary drive shaft 10602". The threaded nut 10730" is threadably received within a threaded bore 10729" in the distal frame member 10720" for rotatable threaded travel therein. The threaded nut 10730" is also attached to the actuator yoke assembly 10710" to permit relative rotation therebetween. For example, a distally protruding rotary hub 10732" is formed on the threaded nut 10730" and is rotatably received within a bore 10711" in the actuator yoke assembly 10710". The rotary hub 10732" may be rotatably retained within the bore 10711" by a split ring 10713" or other retention feature.

In certain instances, the first and second jaws 10250, 10270 are opened and closed as follows. To open and close the jaws 10250, 10270, the unlocking cable or unlocking rod 10342" must be in locking engagement with a corresponding one of the recesses 10726" in the proximal end of the proximal end portion 10722" to prevent rotation thereof. See FIG. 50. As was discussed above, in certain instances, the unlocking cable or unlocking rod 10342" may be biased in the locked position by a spring or other biasing arrangement. When the unlocking cable or unlocking rod 10342" is in the locked position, rotation of the rotary drive shaft 10602" in a first direction will rotate the threaded nut 10730" within the threaded bore 10729" in the distal frame member 10720" and drive the actuator yoke assembly 10710" in the distal direction DD. Because the unlocking cable or unlocking rod 10342" is in locking engagement with the proximal end portion 10729" of the distal frame member 10720", the surgical end effector 10200" is prevented from rotating about the shaft axis SA when the rotary drive shaft 10602" is rotated. Rotation of the rotary drive shaft 10602" will axially drive the actuator yoke assembly 10710" distally and cause the jaws 10250, 10270 to pivot towards an open position. Rotation of the rotary drive shaft 10602" in a second direction opposite the first direction will axially drive the actuator yoke assembly 10710" proximally and pull the jaws 10250, 10270 toward a closed position.

To rotate the surgical end effector 10200" about the shaft axis SA, the unlocking cable or unlocking rod 10342" is pulled proximally to thereby disengage from the corresponding recess 10726" in the proximal end portion 10729" of the distal frame member 10720". Thereafter, the rotary drive shaft 10602" is rotated in a desired direction. In such instance, there is enough friction between the threaded nut 10730" and the internal threads 10729" in the distal frame member 10720" such that rotation of the threaded nut 10730" will cause the distal frame member 10720" (and the surgical end effector 10200") to rotate about the shaft axis SA.

Figure 52:
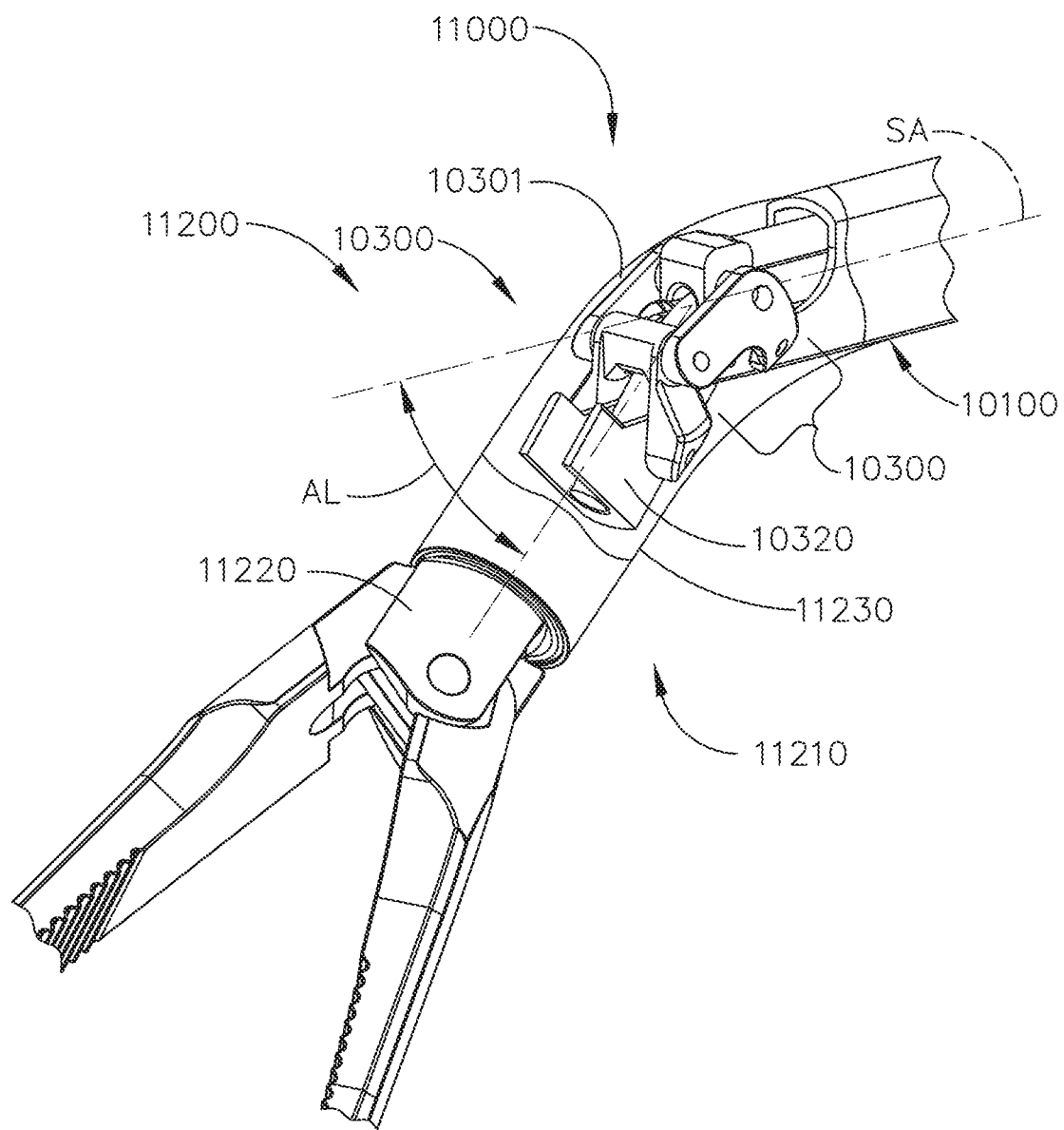
FIG. 52 is a perspective view of a portion of another articulatable surgical instrument with a surgical end effector thereof in an articulated position and jaws of the surgical end effector in an open position, in accordance with at least one aspect of the present disclosure.
Figure 53:
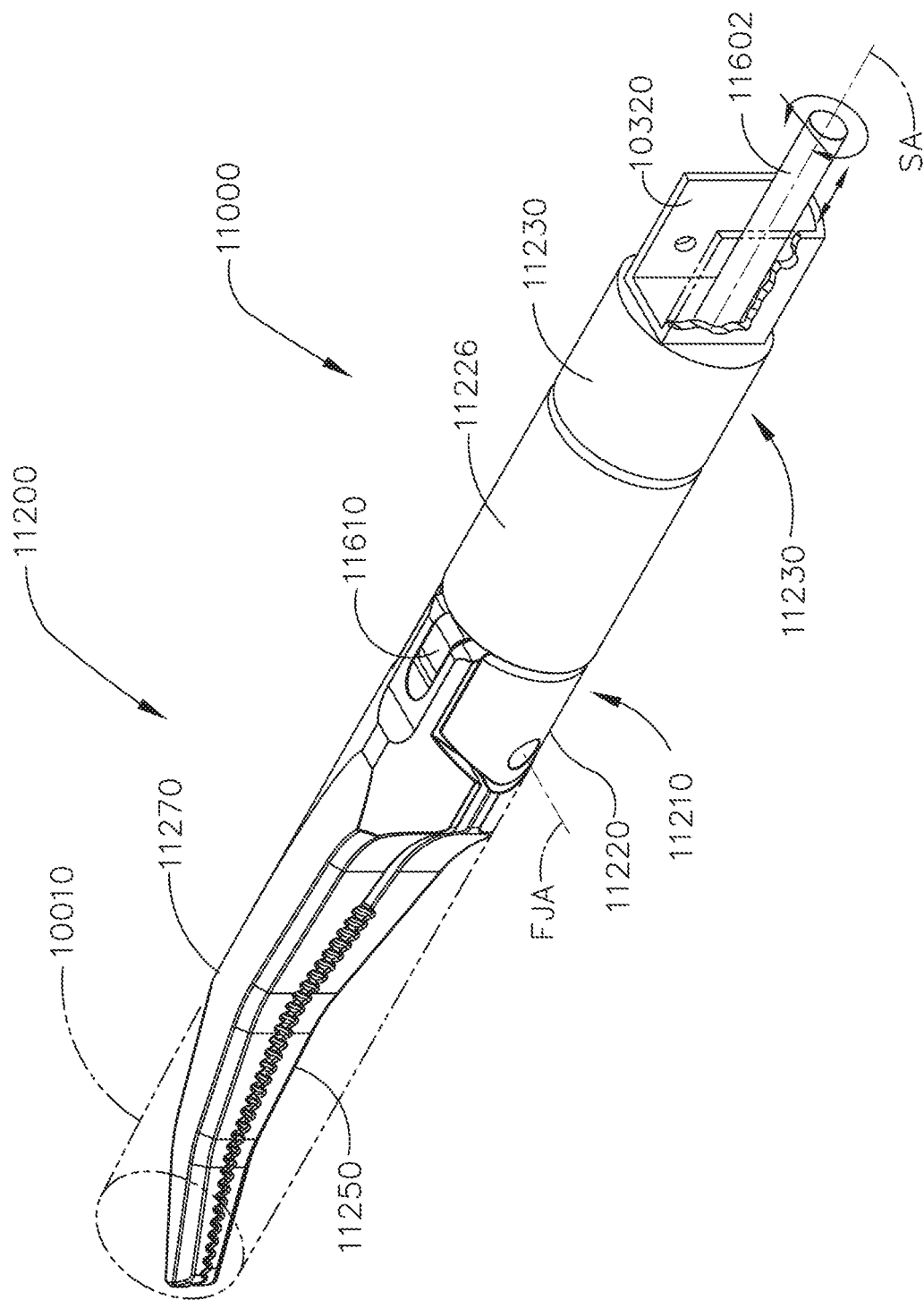
FIG. 53 is a perspective view of a portion of the surgical instrument of FIG. 52 with the surgical end effector thereof in an unarticulated position and the jaws thereof in a closed position.
Figure 54:
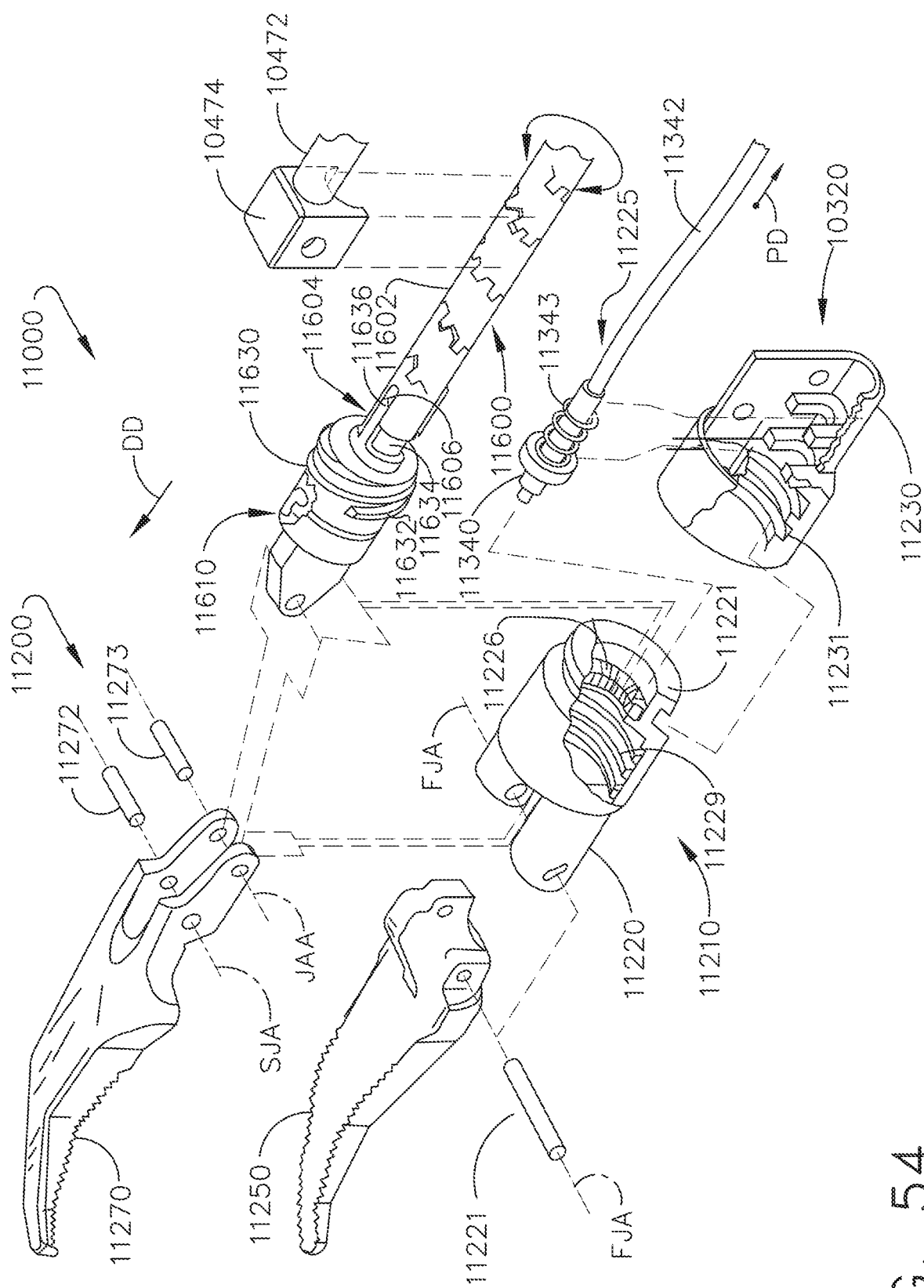
FIG. 54 is an exploded perspective assembly view of a portion of the surgical instrument of FIG. 52.

FIGS. 52-54 illustrate another surgical instrument 11000 that comprises a surgical end effector 11200 that is coupled to a proximal shaft segment 10100 by an articulation joint 10300 in the various manners described herein. In certain instances, a flexible cover 10301 may be provided over the articulation joint 10300 to prevent fluids and debris from hampering operation of the articulation joint 10300. As can also be seen in FIG. 52, such arrangement may facilitate articulation of the surgical end effector 11200 relative to the shaft axis SA through an articulation angle AL. In at least one arrangement, for example, the articulation angle AL may be slightly less than 50 degrees.

In certain instances, the surgical end effector 11200 comprises an end effector frame assembly 11210 that comprises a distal frame member 11220 that is rotatably supported in a proximal frame housing 11230 that is fixedly attached to the proximal end effector frame member 10320. For example, the proximal frame housing 11230 may be attached to the proximal end effector frame member 10320 by welding, adhesive, etc. In various instances, the distal frame member 11220 is rotatably attached to the proximal frame housing 11230 by an annular rib 11221 on the distal frame member 11220 that is received within an annular groove 11231 in the proximal frame housing 11230.

In various instances, the surgical instrument 11000 further comprises an end effector locking system 11225 that comprises a plurality of radial grooves or recesses 11226 that are formed in the distal frame member 11220. The locking system 11225 further comprises a lock insert 11340 that is adapted to lockingly engage the radial grooves 11226 in the distal frame member 11220. The lock insert 11340 is coupled to an unlocking cable or rod 11342 that extends through the articulation joint 10300 and is flexible to accommodate articulation of the surgical end effector 11200. As was discussed herein, the unlocking cable 11342 operably interfaces with a motor or other control system in the housing to pull the unlocking cable or unlocking rod 11342 in the proximal direction. A locking spring 11343 serves to bias the lock insert 11340 into locking engagement with the grooves 11226 in the distal frame member 11220 to prevent the distal frame member 11220 (and surgical end effector 11200) from rotating about the shaft axis SA.

In one example, a first jaw 11250 is pivotally pinned to the distal frame member 11220 for selective pivotal travel relative thereto about a first jaw axis FJA defined by a first jaw pin 11221. A second jaw 11270 is pivotally pinned to the first jaw 11250 for selective pivotal travel relative to the first jaw 11250 about a second jaw axis SJA that is defined by a second jaw pin 11272. In the illustrated example, the surgical end effector 11200 employs actuator yoke assembly 11610 that is pivotally coupled to the second jaw 11270 by a second jaw attachment pin 11273 for pivotal travel about a jaw actuation axis JAA that is proximal and parallel to the first jaw axis FJA and the second jaw axis SJA. The actuator yoke assembly 11610 is coupled to a threaded member 11630. In the illustrated example, the threaded member 11630 essentially comprises a worm gear 11632 that is configured to threadably engage corresponding threads in a threaded bore 11229 in the distal frame member 11220. As the threaded member 11630 is rotated about the shaft axis SA, the worm gear 11632 also causes the threaded member 11630 to translate axially.

The surgical instrument 11000 comprises an end effector drive member 11600. In at least one arrangement, an end effector drive member 11600 comprises a flexible rotary shaft 11602 that is capable of rotation while being able to bend and flex to accommodate articulation of the surgical end effector 11200 in the manners described herein. In certain instances, the flexible rotary shaft 11602 may operably interface with a motor or other source of rotary motion supported in a housing and comprises a laser-cut hollow tube that is capable of flexing or bending to accommodate articulation of the surgical end effector 11200. A distal end 11604 of the flexible rotary drive shaft 11602 has diametrically opposed slots 11606 formed therein. The slots 11606 are each configured to receive therein a corresponding fin 11636 that is formed on a proximally extending hub 11634 on the threaded member 11630. Such arrangement permits the flexible rotary shaft 11602 to convey rotary control motions to the threaded member 11630 while permitting the threaded member 11630 to translate axially relative to the distal end 11604 of the flexible rotary shaft 11602.

In certain instances, the first and second jaws 11250, 11270 are opened and closed as follows. To open and close the jaws, as was discussed in detail above, the lock insert 11340 is in locking engagement with a corresponding radial groove 11226 in the distal frame member 11220 to prevent rotation of the end effector 11200 about the shaft axis SA. Thereafter, rotation of the rotary drive shaft 11602 in a first direction will rotate the threaded member 11630 within the threaded bore or passage 11229 in the distal frame member 11220 and drive the actuator yoke assembly 11610 in the distal direction DD to move the first jaw 11250 and the second jaw 11270 toward an open position. Because the lock insert 11340 is in locking engagement with the distal frame member 11220, the surgical end effector 11200 is prevented from rotating about the shaft axis SA when the rotary flexible drive shaft 110602 is rotated. Rotation of the rotary drive shaft 11602 in a second direction opposite the first direction will axially drive the actuator yoke assembly 11610 proximally and pull the jaws 11250, 11270 toward a closed position.

In various instances, to rotate the surgical end effector 11200 about the shaft axis SA, the unlocking cable 11342 is pulled proximally to cause the lock insert 11340 to disengage the lock grooves 11226 in the distal frame member 11220. Thereafter, the flexible rotary drive shaft 11602 is rotated in a desired direction which will cause the distal frame member 11220 (and the surgical end effector 11200) to rotate about the shaft axis SA.

Figure 55:
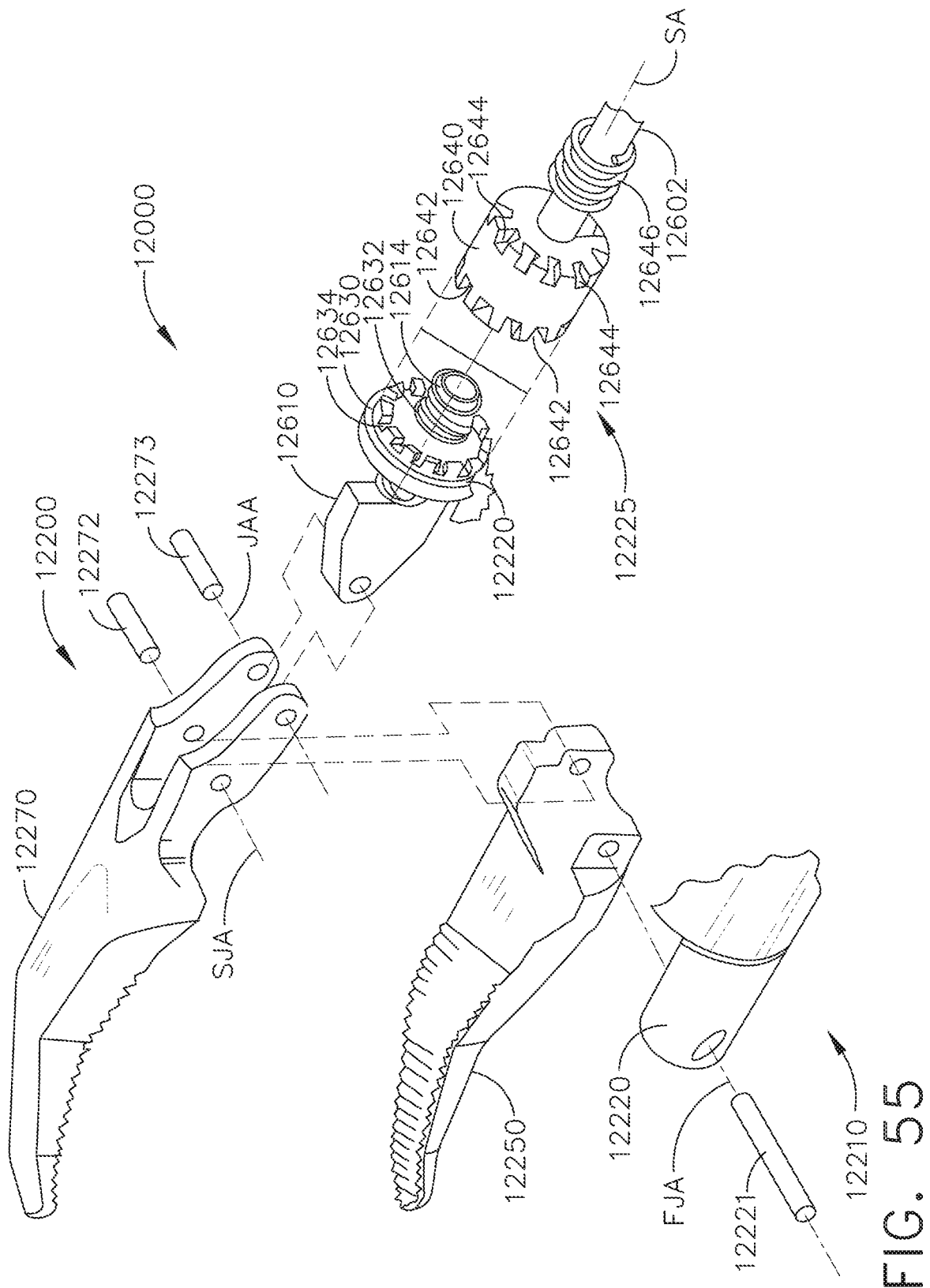
FIG. 55 is an exploded perspective assembly view of a portion of another surgical instrument, in accordance with at least one aspect of the present disclosure.
Figure 56:
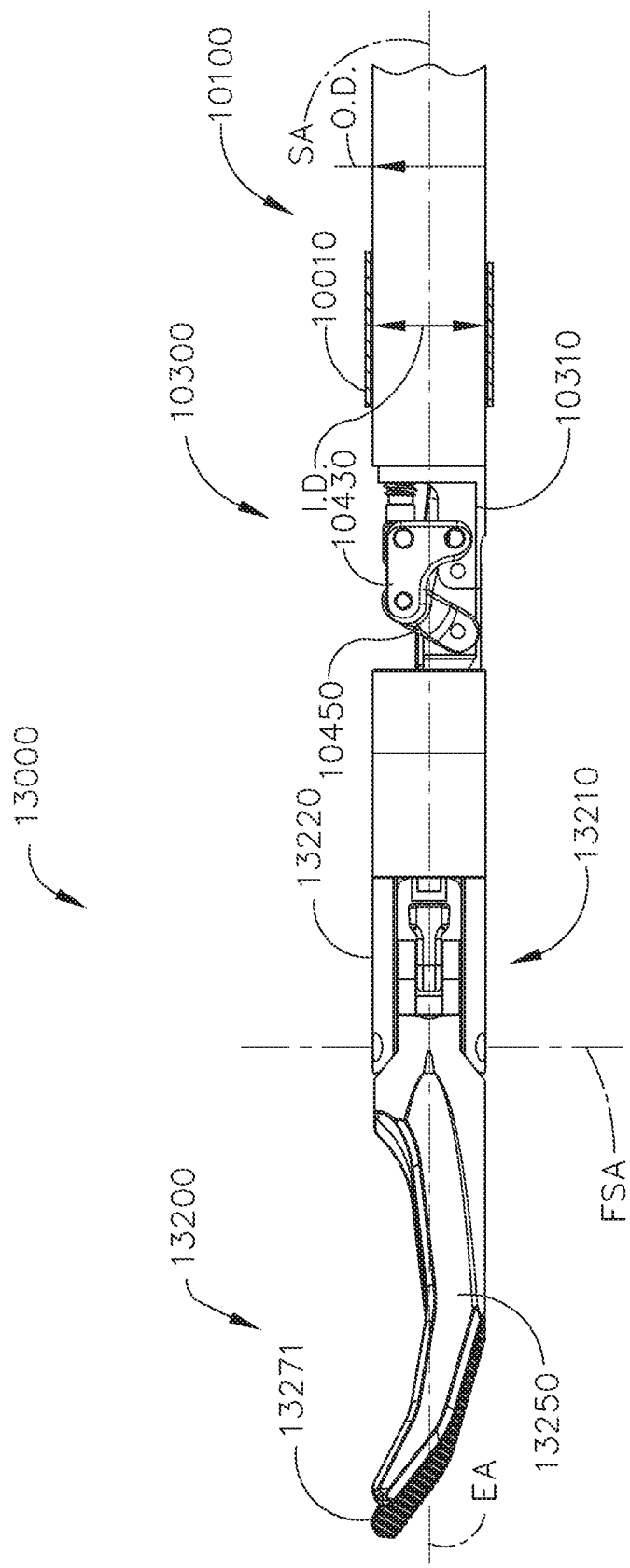
FIG. 56 is a side elevational view of a portion of another surgical instrument with a surgical end effector thereof in an unarticulated position and jaws of the surgical end effector in a partially closed position, in accordance with at least one aspect of the present disclosure.

FIG. 55 illustrates another surgical instrument 12000 that comprises a surgical end effector 12200 that may be coupled to a proximal shaft segment 10100 by an articulation joint 10300 in the various manners described herein. In certain instances, the surgical end effector 12200 comprises an end effector frame assembly 12210 that comprises a distal frame member 12220 that is rotatably supported in a proximal frame housing (not shown) that is attached to the articulation joint (not shown).

The surgical end effector 12200 comprises a first jaw 12250 and a second jaw 12270. In the illustrated example, the first jaw 12250 is pivotally pinned to the distal frame member 12220 for selective pivotal travel relative thereto about a first jaw axis FJA defined by a first jaw pin 12221. The second jaw 12270 is pivotally pinned to the first jaw 12250 for selective pivotal travel relative to the first jaw 12250 about a second jaw axis SJA that is defined by a second jaw pin 12272. In the illustrated example, the surgical end effector 12200 employs an actuator yoke assembly 12610 that is pivotally coupled to the second jaw 12270 by a second jaw attachment pin 12273 for pivotal travel about a jaw actuation axis JAA that is proximal and parallel to the first jaw axis FJA and the second jaw axis SJA. The actuator yoke assembly 12610 comprises a proximal threaded drive shaft 12614 that is threadably received in a threaded bore 12632 in a distal lock plate 12630. The threaded drive shaft 12614 is mounted to the actuator yoke assembly 12610 for relative rotation therebetween. The distal lock plate 12630 is supported for rotational travel within the distal frame member 12220. Thus rotation of the distal lock plate 12630 will result in the axial travel of the actuator yoke assembly 12610.

In certain instances, the distal lock plate 12630 comprises a portion of an end effector locking system 12225. The end effector locking system 12225 further comprises a dual-acting rotary lock head 12640 that is attached to a rotary drive shaft 12602 of the various types disclosed herein. The lock head 12640 comprises a first plurality of radially arranged distal lock features 12642 that are adapted to lockingly engage a plurality of proximally-facing, radial grooves or recesses 12634 that are formed in the distal lock plate 12630. When the distal lock features 12642 are in locking engagement with the radial grooves 12634 in the distal lock plate 12630, rotation of the rotary lock head 12640 will cause the distal lock plate 12630 to rotate within the distal frame member 12220. Also in at least one example, the rotary lock head 12640 further comprises a second series of proximally-facing proximal lock features 12644 that are adapted to lockingly engage a corresponding series of lock grooves (not shown) that are provided in the distal frame member 12220. A locking spring 12646 serves to bias the rotary lock head 12640 distally into locking engagement with the distal lock plate 12630. In various instances, the rotary lock head 12640 may be pulled proximally by an unlocking cable or other member (not shown) in the manner described herein. In another arrangement, the rotary drive shaft 12602 may be configured to also move axially to move the rotary lock head 12640 axially within the distal frame member 12220. When the proximal lock features 12644 in the rotary lock head 12640 are in locking engagement with the series of lock grooves in the distal frame member 12220, rotation of the rotary drive shaft 12602 will result in rotation of the surgical end effector 12200 about the shaft axis SA.

In certain instances, the first and second jaws 12250, 12270 are opened and closed as follows. To open and close the jaws, as was discussed in detail above, the rotary lock head 12640 is in locking engagement with the distal lock plate 12630. Thereafter, rotation of the rotary drive shaft 12602 in a first direction will rotate the distal lock plate 12630 which will axially drive the actuator yoke assembly 12610 in the distal direction DD and move the first jaw 12250 and the second jaw 12270 toward an open position. Rotation of the rotary drive shaft 12602 in an opposite second direction will axially drive the actuator yoke assembly 12610 proximally and pull the jaws 12250, 12270 toward a closed position. To rotate the surgical end effector 12200 about the shaft axis SA, the locking cable or member is pulled proximally to cause the rotary lock head 12640 to disengage from the distal lock plate 12630 and engage the distal frame member 12220. Thereafter, when the rotary drive shaft 12602 is rotated in a desired direction, the distal frame member 12220 (and the surgical end effector 12200) will rotate about the shaft axis SA.

Figure 57:
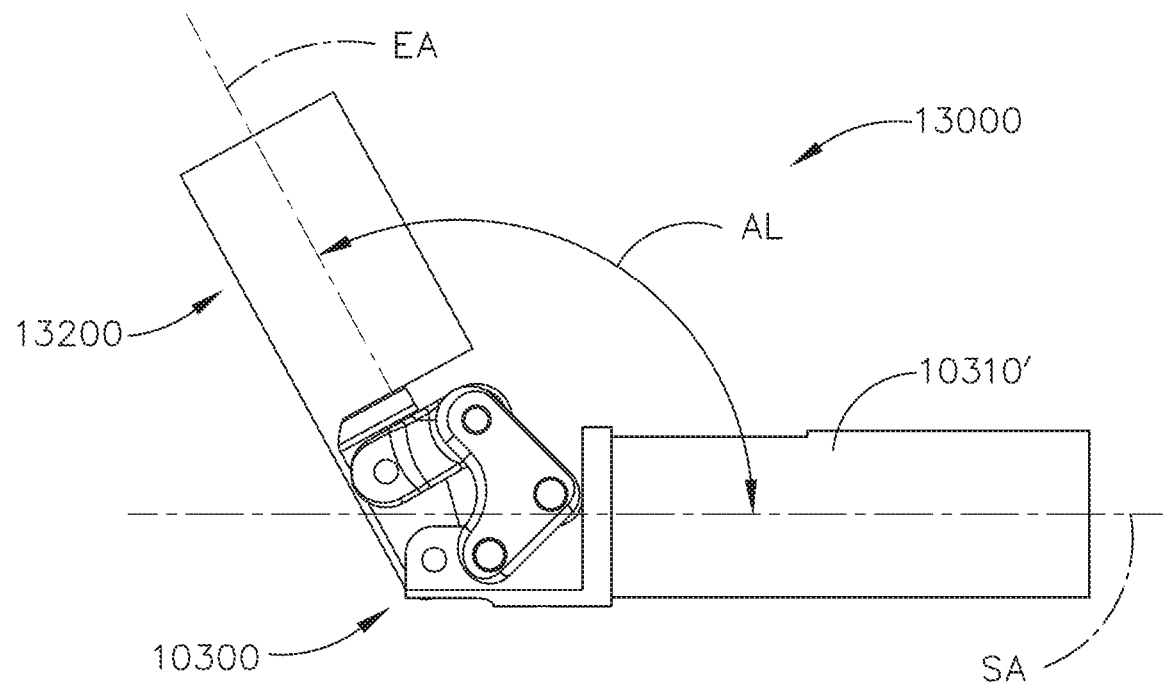
FIG. 57 is a partial side elevational view of a portion of an articulation joint of the surgical instrument of FIG. 56 articulated in a first direction.
Figure 58:
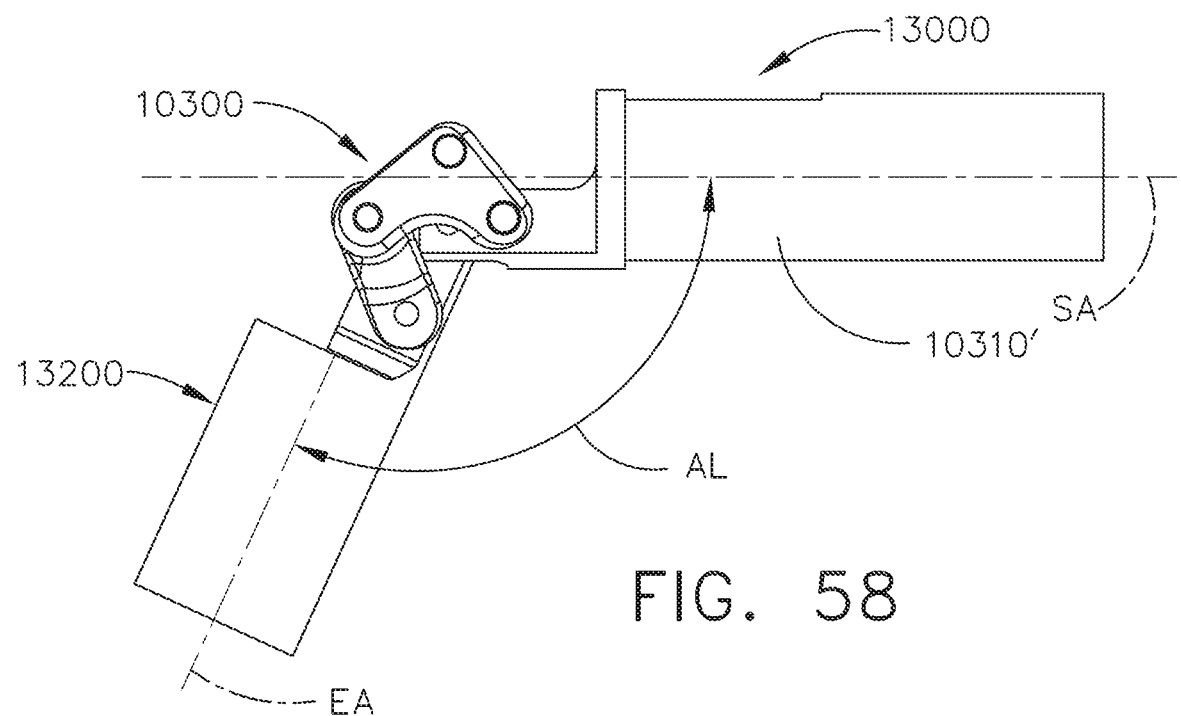
FIG. 58 is another partial side elevational view of the articulation joint of FIG. 56 articulated in a second direction.

FIGS. 56-67 illustrate another surgical instrument 13000 that comprises a surgical end effector 13200 that may be coupled to a proximal shaft segment 10100 by an articulation joint 10300 in the various manners described herein. In certain instances, the surgical end effector 13200 comprises an end effector frame assembly 13210 that defines an end effector axis EA. As can be seen in FIGS. 57 and 58, the articulation joint 10300 may facilitate selective articulation of the surgical end effector 13200 relative to the shaft axis SA through an articulation angle AL on each side of the shaft axis SA. In various instances, the articulation angle AL may be approximately sixty degrees, for example.

Figure 59:
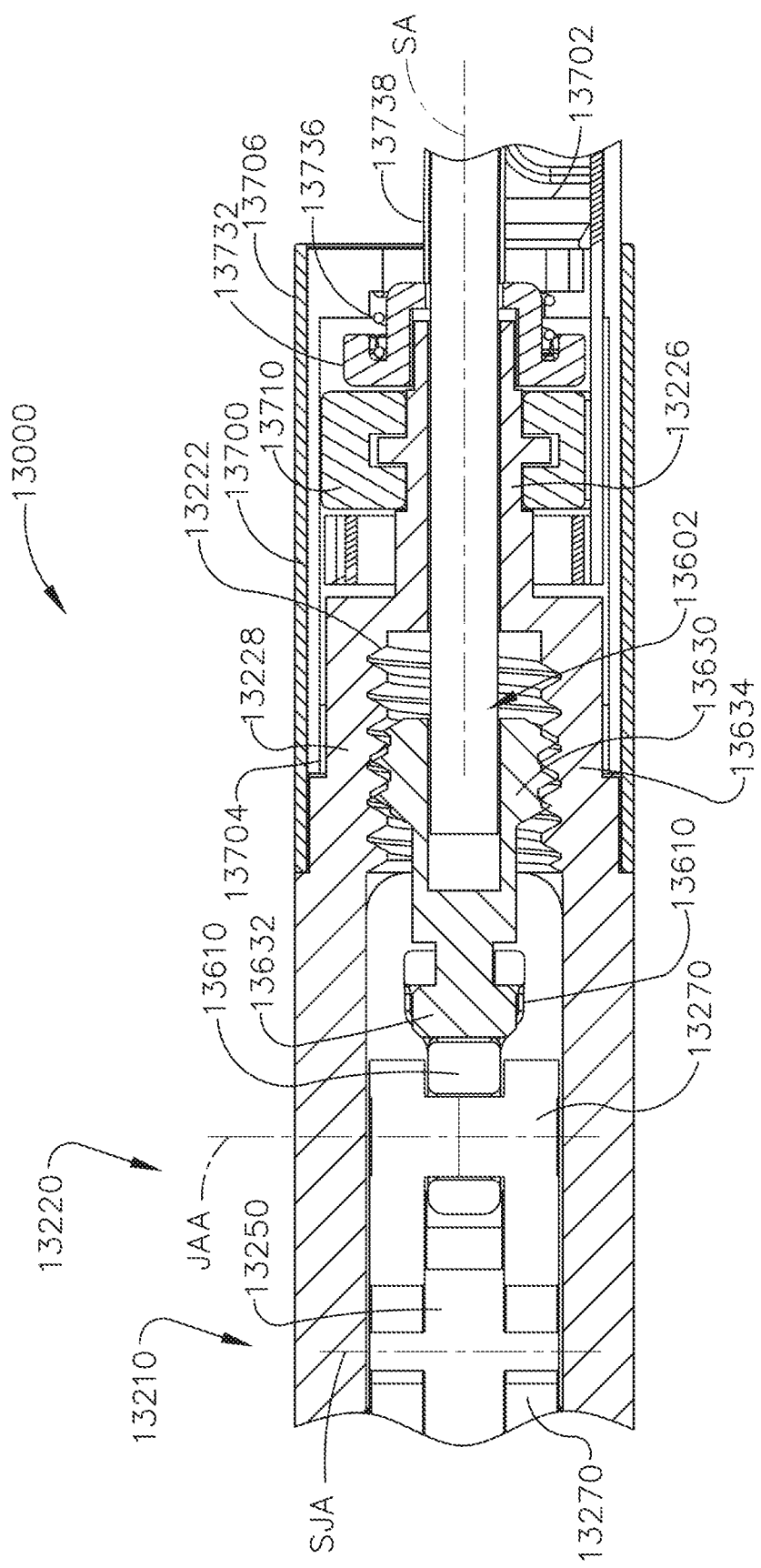
FIG. 59 is a partial cross-sectional side view of a portion of the surgical instrument of FIG. 56.
Figure 60:
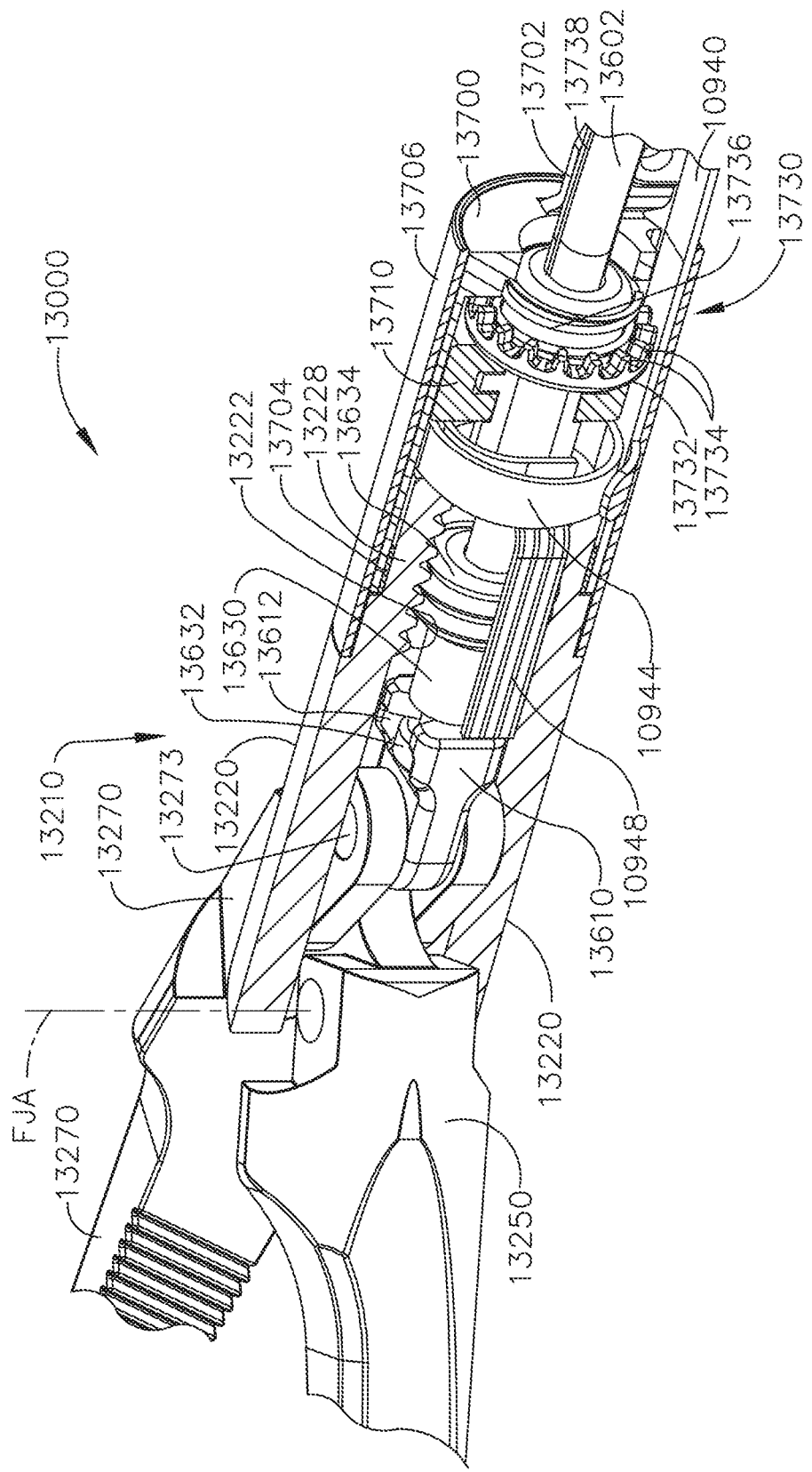
FIG. 60 is a partial perspective view of a portion of the surgical instrument of FIG. 56.
Figure 61:
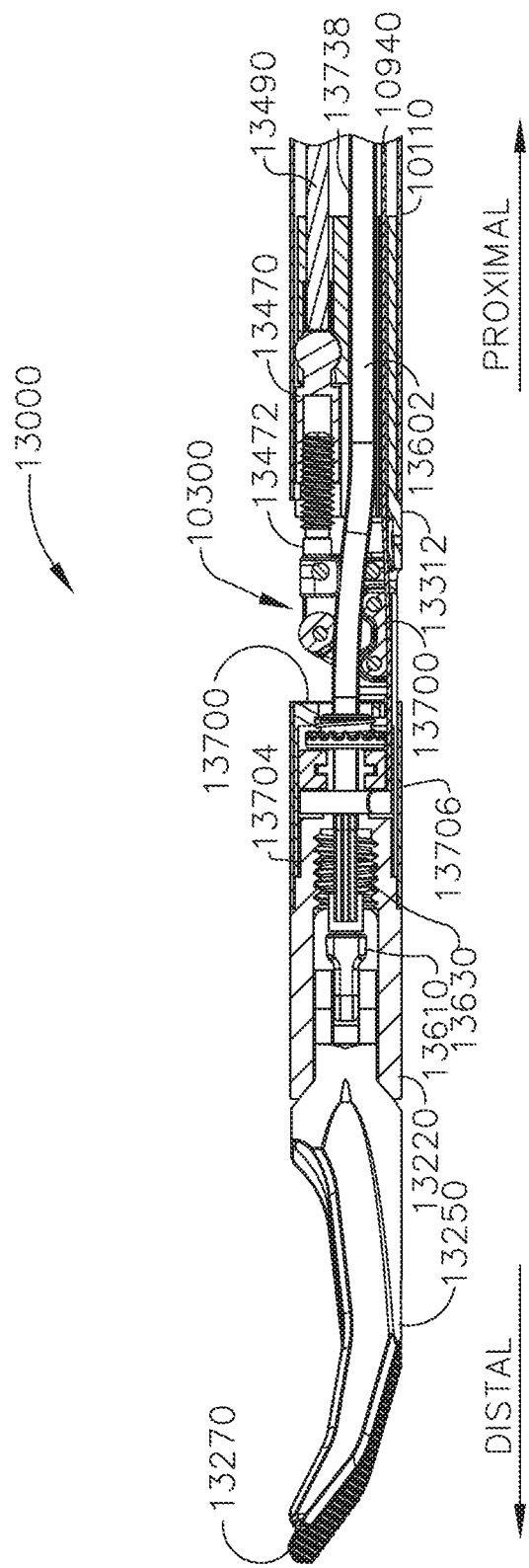
FIG. 61 is a cross-sectional side view of a portion of the surgical instrument of FIG. 56.
Figure 62:
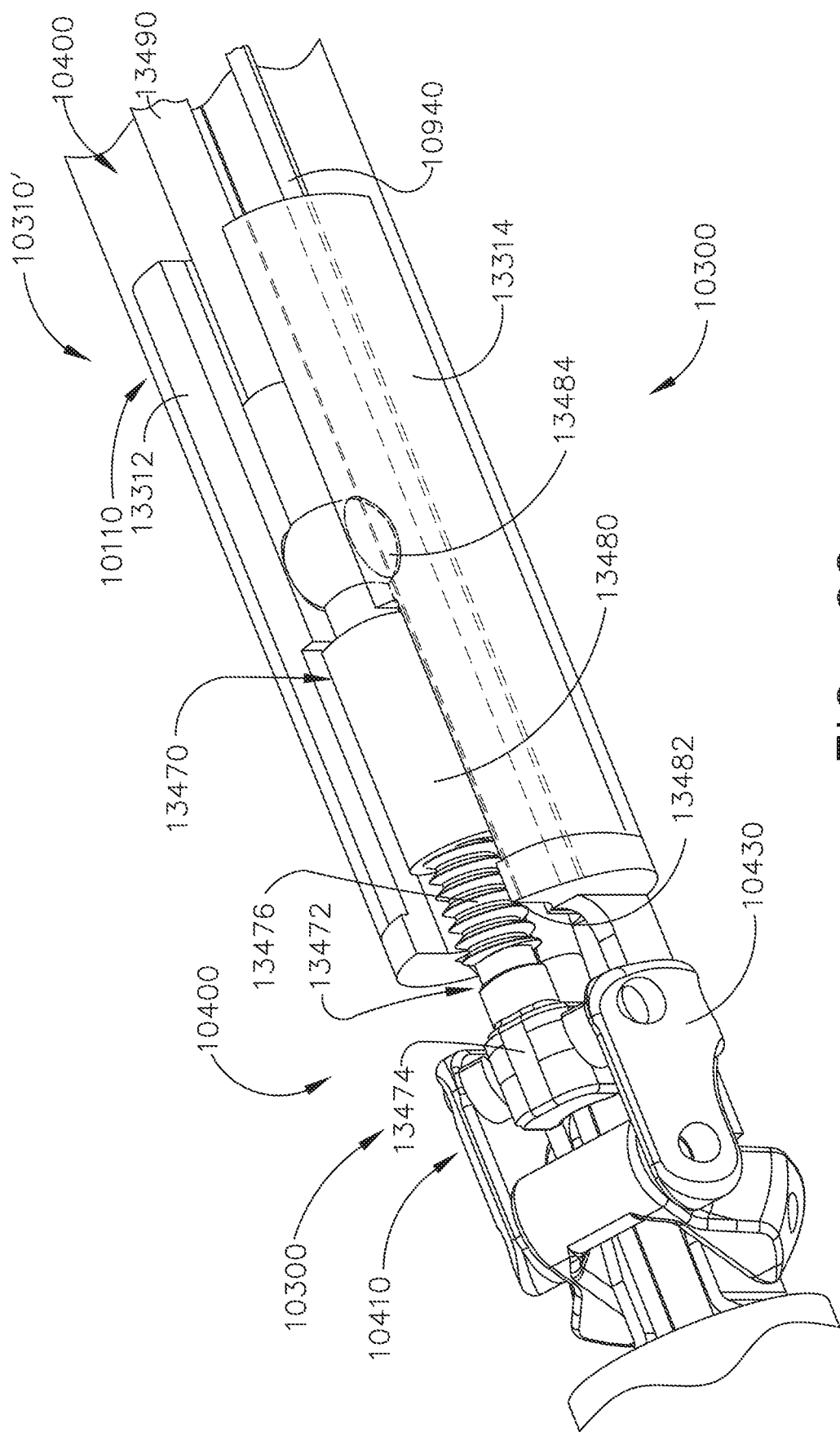
FIG. 62 is a partial perspective view of a portion of the surgical instrument of FIG. 56.

Turning to FIGS. 59 and 60, in certain instances, the end effector frame assembly 13210 comprises a distal frame member 13220 and a distal retainer assembly 13700. In the illustrated example, a first jaw 13250 is pivotally pinned to the distal frame member 13220 for selective pivotal travel relative thereto about a first jaw axis FJA. See FIG. 60. A second jaw 13270 is pivotally pinned to the first jaw 13250 for selective pivotal travel relative to the first jaw 13250 about a second jaw axis SJA. See FIG. 59. In various instances, the surgical end effector 13200 employs actuator yoke assembly 13610 that is pivotally coupled to the second jaw 13270 by a second jaw attachment pin 13273 for pivotal travel about a jaw actuation axis JAA that is proximal and parallel to the first jaw axis FJA and the second jaw axis SJA. The actuator yoke assembly 13610 is coupled to a threaded nut member 13630 for relative rotation therebetween. For example, as can be seen in FIGS. 59 and 60, the threaded nut member 13630 comprises a retainer head 13632 that is rotatable received in a cavity 13612 in the actuator yoke assembly 13610. Such arrangement permits the threaded nut member 13630 to rotate without rotating the actuator yoke assembly 13610. The threaded nut member 13630 further includes a threaded segment 13634 that is threadably received within a threaded passage 13222 in the distal frame member 13220. A flexible rotary drive shaft 13602 is attached to the threaded nut member 13630.

In certain instances, the distal frame member 13220 further includes a proximally protruding central axle portion 13226. The central axle portion 13226 is hollow to facilitate rotary passage of the rotary drive shaft 13602 therethrough. The central axle portion 13226 is rotatably supported within the distal retainer assembly 13700 by a bushing 13710. The distal retainer assembly 13700 is supported on a proximal hub portion 13228 of the distal frame member 13220. See FIG. 60. A friction ring 13704 is journaled on the proximal hub portion 13228 between the proximal hub portion 13228 and the distal retainer assembly 13700. An end effector housing member 13706 extends over the distal retainer assembly 13700 and is attached by welding, adhesive, press fit, etc. to a portion of the distal frame member 13220. In various instances, a proximal end of the distal retainer assembly 13700 comprises a pair of upstanding support arms 13702 that are pivotally coupled to the proximal shaft frame member 10310 to facilitate articulation of the surgical end effector 13200 about the articulation axis in various manners described herein.

In at least one arrangement, the surgical end effector 13200 further comprises an end effector locking system 13730 that includes a distal lock member 13732 that is supported for axial and non-rotational movement on the central axial portion 13226 of the distal frame member 13220. Thus, the distal lock member 13732 is axially movable between a locked position and an unlocked position on the central axial portion 13226 but rotates with the central axial portion 13226. The distal lock member 13732 comprises a plurality of proximally extending lock features 13734 that are configured to lockingly engage corresponding lock grooves (not shown) in the distal retainer assembly 13700 when the distal lock member 13732 is in a locked position. An unlocking spring 13736 is provided to bias the distal lock member 13732 distally into the unlocked position. The distal lock member 13732 is selectively movable from the unlocked position to the locked position by a locking cable or locking member 13738 that extends through the proximal shaft segment 10100 to the housing. When the locking cable or locking member 13738 is pulled proximally, the distal locking member 13732 is moved proximally into the locked position. In the illustrated arrangement, the distal locking member 13732 is hollow such that the rotary drive shaft 13602 may extend therethrough. The distal locking member 13732 is axially movable and the rotary drive shaft 13602 is rotatable within the distal locking member 13732.

In certain instances, the first and second jaws 13250, 13270 are opened and closed as follows. To open and close the jaws, the distal locking member 13732 is moved into the locked position by pulling the locking cable or locking member 13738 in the proximal direction. Thereafter, rotation of the rotary drive shaft 13602 in a first direction will rotate the threaded nut member 13630 which will axially drive the actuator yoke assembly 13610 in the distal direction to move the first jaw 13250 and the second jaw 13270 toward an open position. Rotation of the rotary drive shaft 13602 in a second direction opposite the first direction will axially drive the actuator yoke assembly 13610 proximally and pull the jaws 13250, 13270 toward a closed position. To rotate the surgical end effector 13200 about the shaft axis SA, the locking cable or locking member 13738 is released to permit the distal locking member 13732 to be biased distally by the spring 13736 into an unlocked position. Thereafter, the rotary drive shaft 13602 is rotated in a desired direction which will cause the distal frame member 13220 (and the surgical end effector 13200) to rotate about the shaft axis SA.

As indicated above, the surgical instrument 13000 may comprise an articulation joint 10300 that is controlled by an articulation system 10400. In various instances, the articulation system 10400 employs a rotary driven articulation actuator 13470 that is configured to apply articulation motions to the right proximal link 10410 and the left proximal link 10430 upon application of rotary articulation control motions thereto. See FIG. 62. In the illustrated arrangement, the articulation actuator 13470 comprises a distal articulation shaft 13472 that includes a distal end formation 13474 that is pivotally coupled to the right proximal link 10410 and the left proximal link 10430 in the above described manner. As can be seen in FIGS. 62-65, the distal articulation shaft 13472 further comprises an axial articulation drive member 13476 that is threadably received in a threaded passage 13482 in a rotatable articulation driver 13480. See FIG. 63. The rotatable articulation driver 13480 further includes a ball-shaped support feature 13484 that rotatably supports the rotatable articulation driver 13480 within the proximal shaft segment 10100 while also facilitating limited off-axis tilting of the articulation driver 13480 during articulation of the surgical end effector 13200.

The rotatable articulation driver is 13480 rotatably supported within a proximal shaft frame member 10310' that is supported within a proximal outer shaft tube 10110 that may extend from the housing or otherwise interface therewith. In the illustrated example, for assembly purposes, the proximal shaft frame member 10310' comprises a right proximal frame segment 13312 and a left proximal frame segment 13314. A rotary articulation drive shaft or cable 13490 is attached to the rotatable articulation driver 13480 and is configured to receive rotary articulation control motions from an articulation motor or other control arrangement supported by the housing.

FIG. 63 is a side cross-sectional view of the articulation joint 10300 in an unarticulated position. As can be seen in FIG. 63, when the articulation joint 10300 is in an unarticulated position, an articulation drive shaft axis ADA is approximately parallel to the shaft axis SA. FIG. 64 illustrates the articulation joint 10300 articulated to the right approximately sixty degrees. In such instance, the rotary articulation drive shaft or cable 13490 is rotated in a first rotary direction. As can be seen in FIG. 64, the rotatable articulation driver 13480 can assume a first angle $FAA_1$ relative to the articulation drive shaft axis ADA to accommodate articulation of the surgical end effector 13200 through a full range of articulation to the right of the shaft axis SA. In one example, the surgical end effector may be articulatable through an angle of approximately sixty degrees on the right side of the shaft axis SA. FIG. 65 illustrates the articulation joint 10300 articulated to the left. In such instance, the rotary articulation drive shaft or cable 13490 is rotated in a second rotary direction opposite the first rotary direction. As can be seen in FIG. 65, the rotatable articulation driver 13480 can also assume a second angle $SAA_2$ relative to the articulation drive axis ADA to accommodate articulation of the surgical end effector 13200 through a full range of articulation to the left of the shaft axis SA. In one example, the full range of articulation may be through an angle of approximately sixty degrees on a left side of the shaft axis SA.

Figure 66:
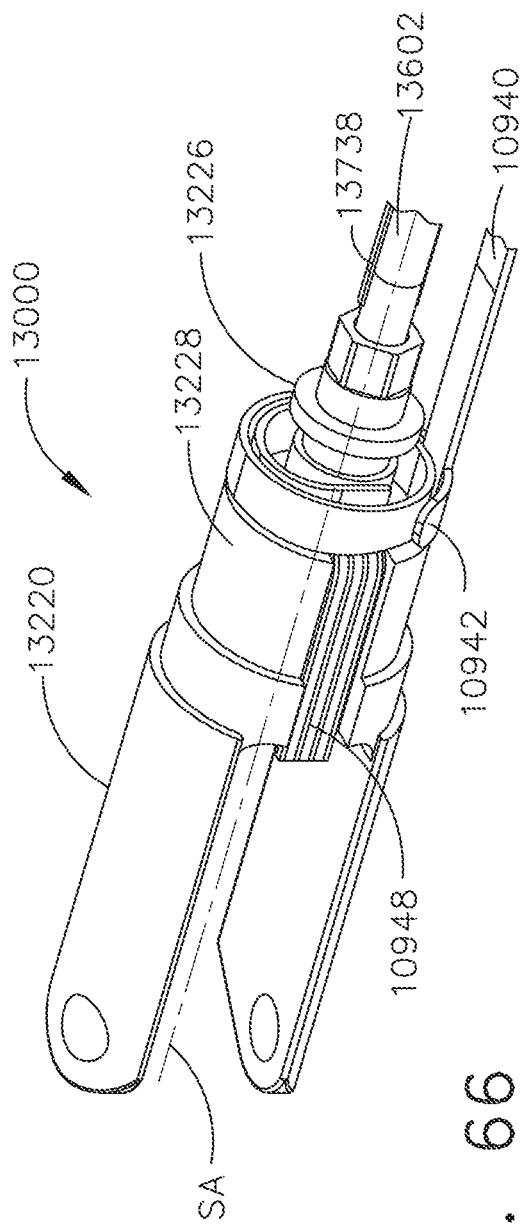
FIG. 66 is a partial perspective view of a distal frame member and a flexible circuit arrangement of the surgical instrument of FIG. 56.
Figure 67:
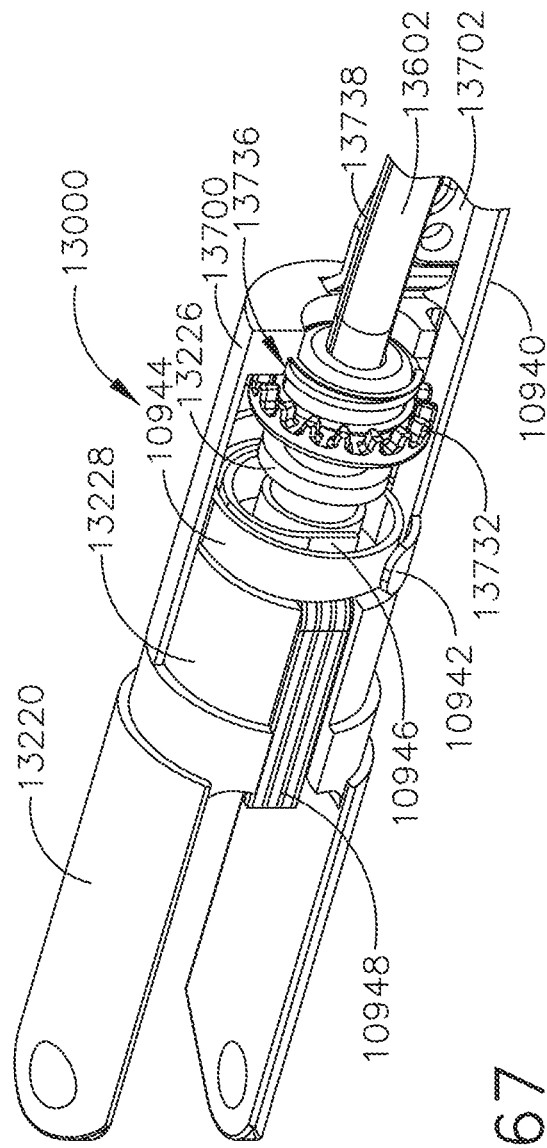
FIG. 67 is another partial perspective view of the distal frame member and flexible circuit arrangement of FIG. 66.

In certain instance, to facilitate transfer of electric signals/power between the housing and the surgical end effector 13200 and more particularly to one or both of the first and second jaws, a flexible circuit 10940 (FIGS. 66, 67) may be provided through the proximal shaft segment 10100 and span the articulation joint 10300. In various instances, as can be seen in FIGS. 66 and 67, the flexible circuit 10940 comprises a left contact end 10942 that may be fixed to the distal retainer assembly 13700 by adhesive for example. The flexible circuit 10940 may further include a right spiral portion 10944. An end 10946 of the right spiral portion 10944 is attached to the axle portion 13226 of the distal frame member 13220 by adhesive for example. The end 10946 may comprise or be coupled to a distally extending flexible circuit 10948 that is supported in the distal frame member 13220 and coupled to the first and second jaws (not shown). Such an arrangement may permit the distal frame member 13220 to rotate through a path of 180 degrees in either direction about the shaft axis SA before the right spiral portion 10944 runs out of length.

Figure 68:
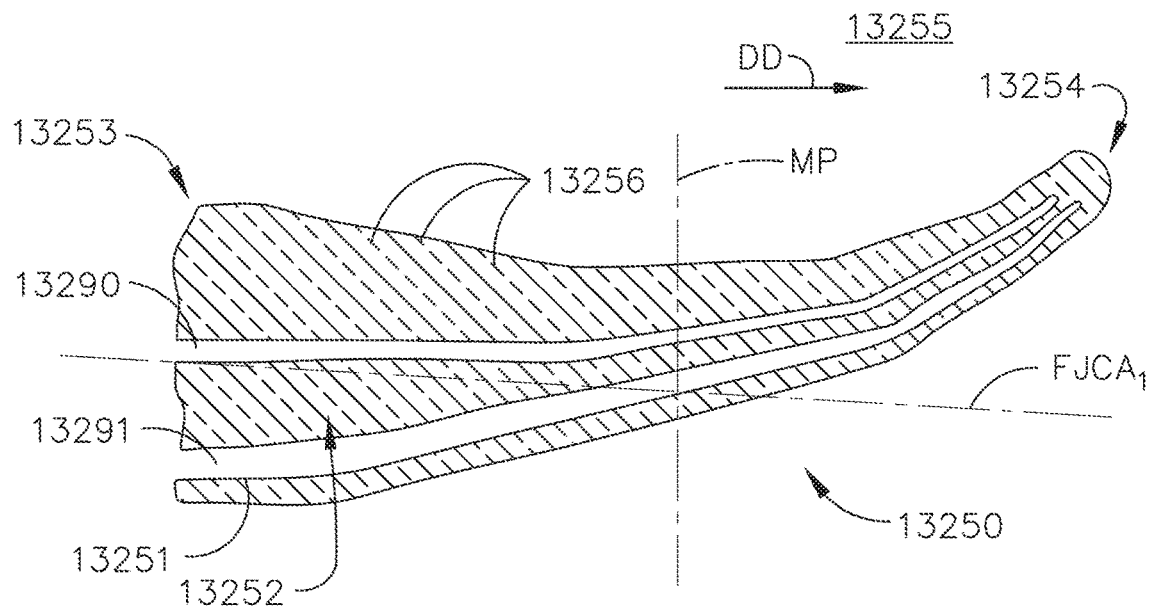
FIG. 68 is a cross-sectional view of a portion of a first jaw embodiment, in accordance with at least one aspect of the present disclosure.

In certain instances, the surgical end effector 13200 employs curved jaws 13250 and 13270 that are designed to facilitate better access to and manipulation of tissue. For example, FIG. 68 illustrates a first jaw 13250 that comprises a first jaw body 13251 that defines a first jaw clamping face 13252. The first jaw body 13251 further comprises a first proximal end 13253 and a first distal tip 13254. In various instances, the first jaw 13250 defines a first jaw center axis $FJCA_1$ and, as can be seen in FIG. 68, the first distal tip 13254 is laterally displaced to a first side 13255 of the first jaw center axis $FJCA_1$. In one example, the first jaw 13250 supports a first monopolar electrode 13290 and a first bipolar electrode 13291.

Figure 69:
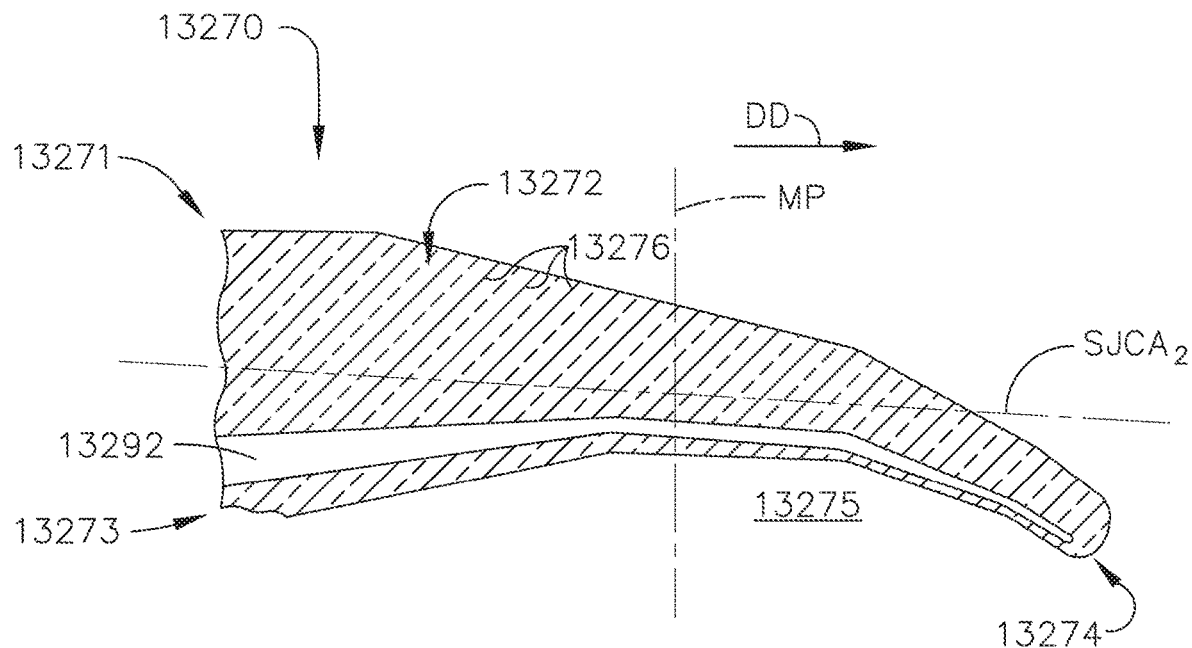
FIG. 69 is a cross-sectional view of a portion of a second jaw embodiment, in accordance with at least one aspect of the present disclosure.

In various instances, the second jaw 13270 comprises a second jaw body 13271 that defines a second jaw clamping face 13272. In one example, the portion of the second jaw body 13271 that defines the second clamping face 13272 may essentially comprise a mirror image of the portion of the first jaw body 13251 that defines the first jaw clamping face 13252. In certain instances, the second jaw body 13271 further comprises a second proximal end 13273 and a second distal tip 13274. The second jaw 13270 defines a second jaw center axis $SJCA_2$ and, as can be seen in FIG. 69, the second distal tip 13274 is laterally displaced to a first side 13275 of the end second jaw center axis $SJCA_2$. In the illustrated example, the second jaw 13270 supports a second bipolar electrode 13292.

In various instances, in use, when the first jaw 113250 and the second jaw 13270 are moved from an open position to a fully closed position without clamping onto tissue, the first jaw 13250 and the second jaw 13270 will be approximately perfectly aligned with each other. When in that position, for example, the first jaw center axis $FJCA_1$ and the second and the second jaw center axis $SJCA_2$ will both lie on a common plane. The second distal tip 13274 will be aligned with the first distal tip 13254. When the first jaw 13250 and the second jaw 13270 are clamped onto tissue, the tissue may tend to skew portions of the first jaw 13250 and the second jaw 13270 out of alignment. This misalignment may be the greatest at the distal tips of the jaws. Such misalignment of the jaws may increase distal to the jaw mid point MP. For example, because the distal tips 13254 and 13274 are laterally displaced (curved) from the jaw center axes $FJCA_1$ and $SJCA_2$, the distal tips 13254, 13274 are susceptible to further misalignment as the jaws 13254, 13274 continue to clamp down on or close down on tissue. This misalignment is generally undesirable.

Figure 70:
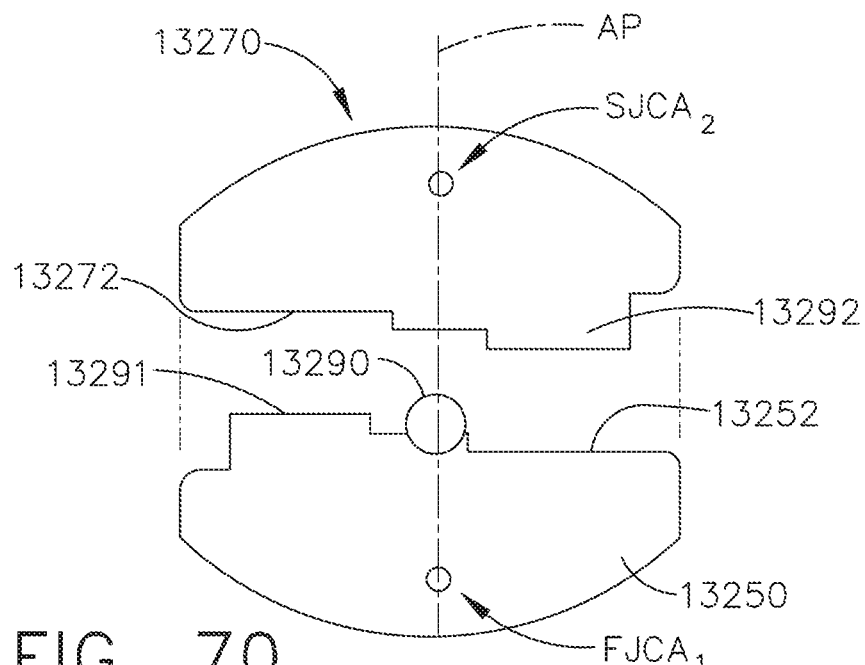
FIG. 70 is a cross-sectional end view of portions of a first jaw and a second jaw in alignment in a closed position, in accordance with at least one aspect of the present disclosure.
Figure 71:
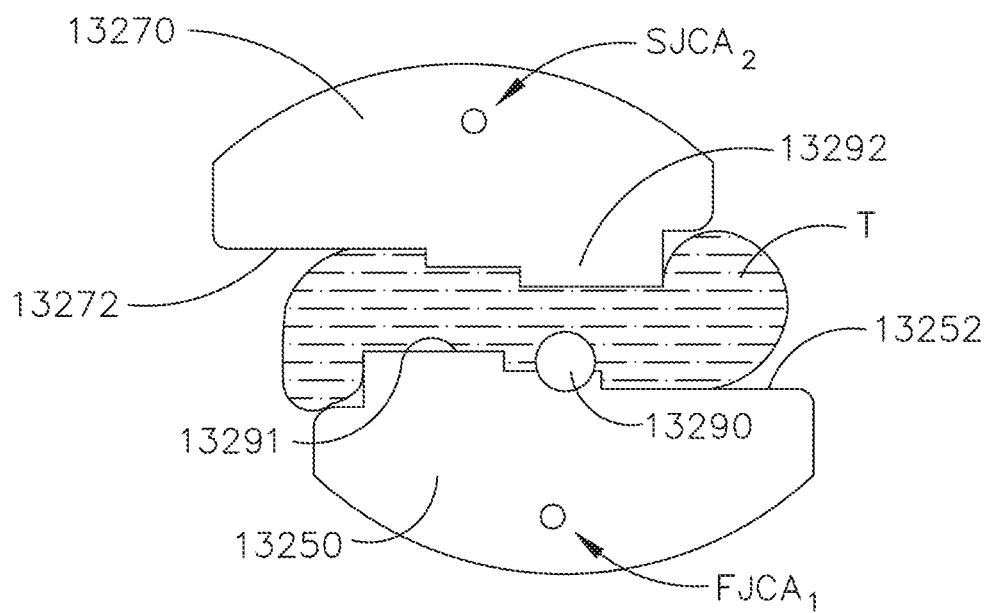
FIG. 71 is another cross-sectional end view of the first jaw and second jaw of FIG. 70 out of alignment while closing onto tissue.
Figure 72:
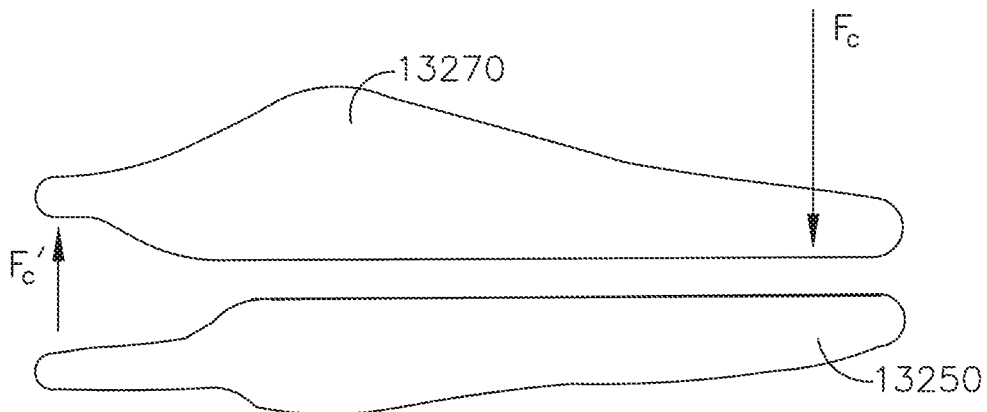
FIG. 72 is a diagrammatic depiction of a first jaw and a second jaw in a closed position, in accordance with at least one aspect of the present disclosure.
Figure 73:
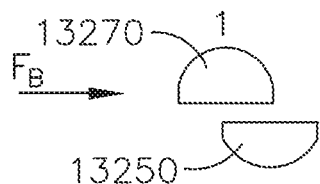
FIG. 73 is a cross-sectional end view of portions of the first jaw and second jaw of FIG. 72 out of alignment during closing.
Figure 74:
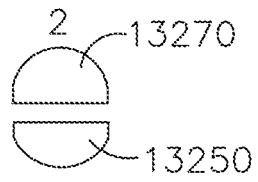
FIG. 74 is a cross-sectional end view of portions of the first jaw and the second jaw of FIG. 72 in alignment in a closed position.
Figure 75:
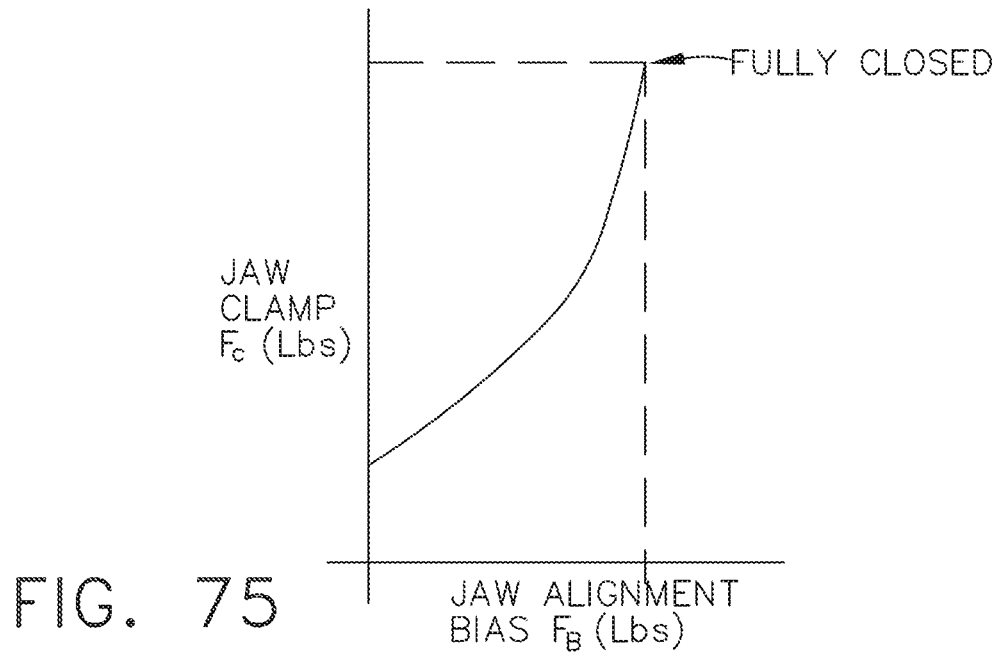
FIG. 75 is a graphical comparison between a jaw clamping force required to close a first jaw and a second jaw and an amount of jaw biasing force required to move the first and second jaws into alignment with each other as the first and second jaws move from an open position to a fully closed position, in accordance with at least one aspect of the present disclosure.

FIG. 70 comprises a cross-sectional end view of the first jaw 13250 and the second jaw 13270 during closure (without tissue) wherein the first jaw 13250 and the second jaw 13270 are vertically aligned. During clamping of the jaws 13250, 13270 onto tissue T, the jaws 13250, 13270 may tend to splay laterally and become misaligned (FIG. 71). This misalignment may begin or at least increase in the portions of the jaws that are distal to the jaw midpoints MP. Such undesirable occurrence may result in the formation of an RF short. FIGS. 72 and 73 represent diagrammatical depictions of a clamping force $F_c$ and the resulting amount of biasing force $F_B$ experienced by the jaws 13250, 13270 which tends to skew the jaws and move them out of alignment. An amount of jaw clamping force $F_c$ (lbs.) necessarily increases as the jaws are moved from an open position to a fully closed or clamped position on a target tissue. As the jaws 13250, 13270 are moved toward each other in the closing direction, the amount of misalignment forces experienced by the jaws tends to increase due to the resistance of the tissue. FIG. 75 is a graphical comparison of the jaw clamping force $F_c$ vs. the amount of force required to realign the jaws (jaw biasing force $F_B$) during the jaw closure process.

In certain instances, at least one of the jaws 13250, 13270 comprises at least one alignment feature that is configured to engage a corresponding portion of the other jaw to bring the jaws into "axial alignment" with each other during closing. As used herein, the term "axial alignment" means that a centerline of one jaw is generally axially aligned with a centerline of the other jaw during closing. Further, when the second distal tip 13274 is "aligned with" the first distal tip 13254, the outer perimeter of the second jaw clamping face 13272 is generally aligned with the outer perimeter of the first jaw clamping face 13252 when fully closed or fully clamped on tissue. In another arrangement, when the second distal tip 13274 is "aligned with" the first distal tip 13254, no portion of the first jaw clamping face 13252 extends laterally beyond the second jaw clamping face 13272 when the jaws 13250, 13270 are fully closed or fully clamped on tissue. This definition of "aligned with" is of course applicable to jaws 13250, 13270 that have an identical size and outer shape. If, for example, one of the jaws has a protrusion or formation that extends from an outer surface of the jaw and the protrusion is not found on the corresponding surface of the other jaw, but the jaw with the protrusion is otherwise identical in shape to the other jaw (except for, perhaps, the clamping faces of the jaws), those jaws may be aligned with each other when the centerlines of the jaws line on a common plane. Thus, another definition of "aligned with" in the context of the second jaw 13270 being aligned with the first jaw 13250 may consist of the first jaw 13250 and the second jaw 13270 being aligned with each other such that the first jaw center axis $FJCA_1$ and the second jaw center axis $SJCA_2$ lie along a common alignment plane AP. See FIG. 70.

In an illustrated example, the first jaw 13250 and the second jaw 13270 each have a toothed surface that comprises a series of radially aligned teeth. FIG. 77 depicts a plurality of first alignment features that comprise "radially aligned" first teeth 13256 formed on the first jaw clamping face 13252. Similarly, the second jaw 13270 comprises a plurality of second alignment features that comprise radially aligned second teeth 13276 on the second jaw clamping face 13272. See FIG. 76. As used in this context, the term "radially aligned" means that each tooth lies along a corresponding axis and each axis intersects a common point that is laterally displaced from the center axis of the jaw.

Figure 76:
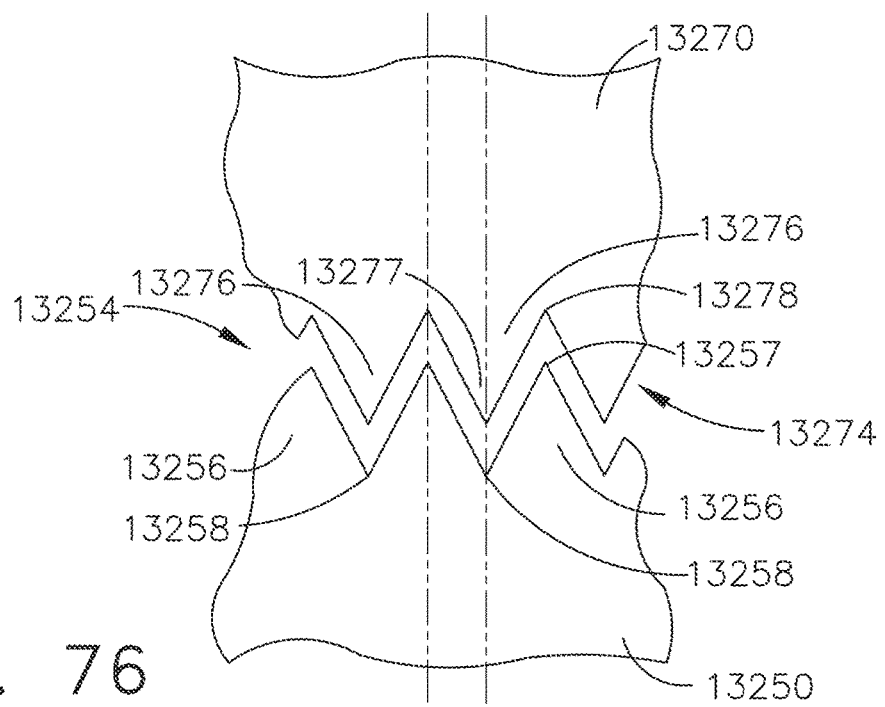
FIG. 76 is a partial cross-sectional view of a portion of a first jaw and a corresponding portion of a second jaw when the first jaw and second jaw are in a closed position, in accordance with at least one aspect of the present disclosure.
Figure 77:
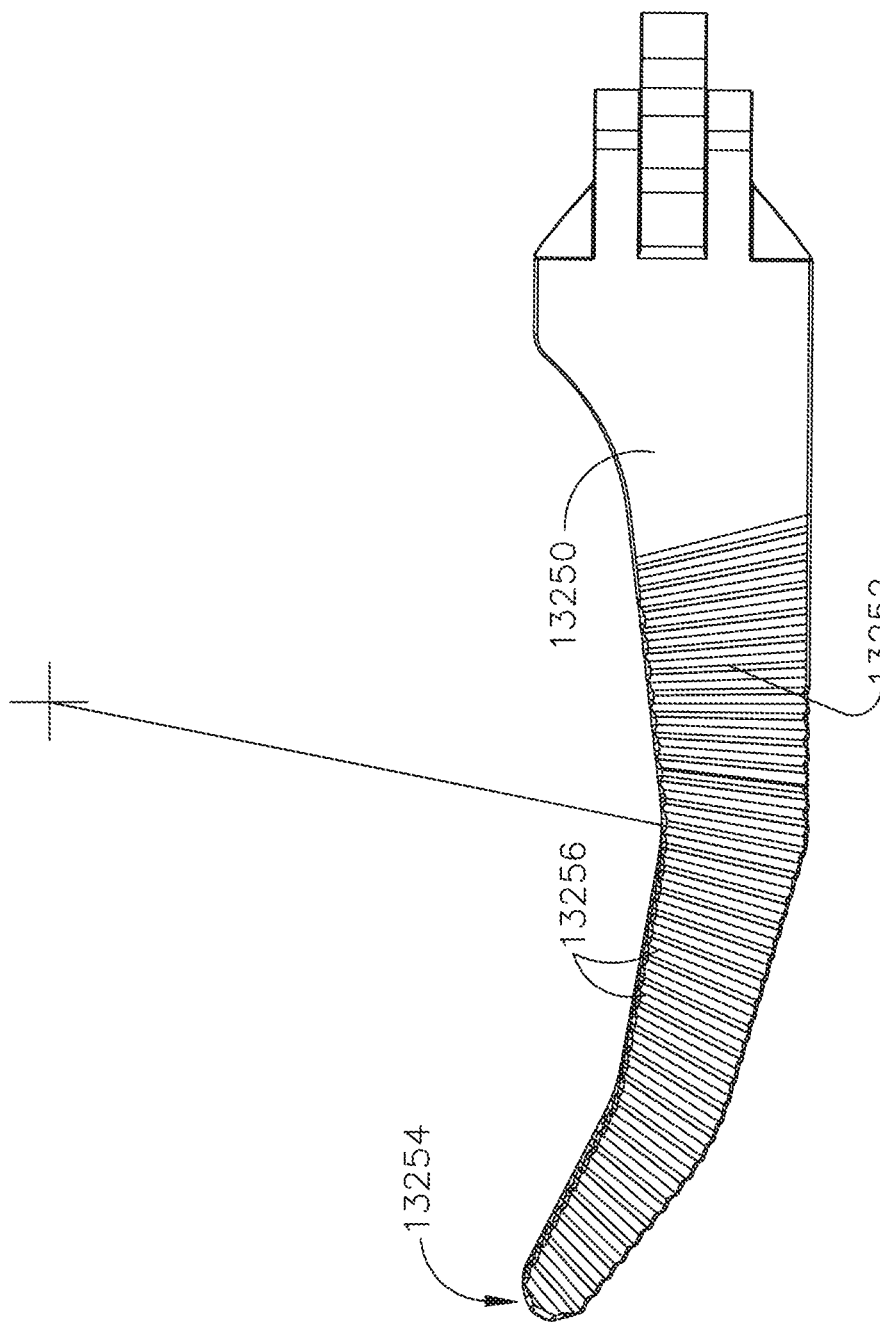
FIG. 77 is a top view of another first jaw, in accordance with at least one aspect of the present disclosure.

FIG. 76 depicts a portion of the first jaw 13250 and a corresponding portion of the second jaw 13270 in cross-section. As can be seen in FIG. 76, each first tooth 13256 has a first tooth tip 13257 and each first tooth 13256 is separated by a first valley 13258. Similarly, the second jaw 13270 has a second toothed surface 13274 that is configured to mate with the first toothed surface 13254 on the first jaw 13250.

As can be further seen in FIG. 76, each second tooth 13276 has a second tooth tip 13277 and each second tooth 13276 is separated by a second valley 13278. In one arrangement the second tooth tip 13277 on each second tooth 13278 is configured to be aligned with a corresponding first valley 13258 and each first tooth tip 13257 is aligned with a corresponding second valley 13278 when the first jaw 13250 and the second jaw 13270 are properly aligned and moved to a closed position. In at least one arrangement, the second teeth 13276 are similarly radially aligned on the second jaw 13270. In use, as the first jaw 13250 and the second jaw 13270 are moved toward each other, at least some of the first tips 13257 and the second tips 13277 eventually become engaged. In one arrangement, for example, the respective height of each first tooth 13256 and of each second tooth 13257 are greater than an amount of tissue gap formed between the first jaw clamping face 13252 and the second jaw clamping face 13272 that is necessary to accommodate the electrodes 13290, 13291, 13292. For example, each of the first teeth tips 13257 (or at least some of them) extend beyond the first electrodes 13290, 13291 on the first jaw 13250. Likewise, each of the second teeth tips 13277 (or at least some of them) extend beyond the electrode 13292 on the second jaw 13270. As the jaws 13250, 13270 continue to move toward each other, the interaction between at least some of the first teeth 13256 and at least some of the corresponding second teeth 13276 serve to move the first distal tip 13254 and the second distal tip 13274 into alignment. Although in the illustrated example, the first teeth 13256 occupy substantially the entire first jaw clamping face 13252 and the second teeth 13276 occupy substantially the entire second jaw clamping face 13272, due to the curved nature of the first jaw 13250 and the second jaw 13270, in certain instances, it is the interaction of at least some of the first teeth 13256 and the corresponding second teeth 13276 that are distal to the jaw midpoint MP that generally serve to bring the first distal tip 13254 and the second distal tip 13274 into alignment during closing/clamping. This alignment progressively increases as the jaws continue to clamp down onto the tissue. Stated another way, the biasing forces that serve to bring the jaws 13250, 13270 into alignment increase as the jaw clamping or closure forces $F_c$ increase.

In certain instances, the first teeth 13256 only encompass the portions of the first jaw clamping face 13252 that are not occupied by either of the electrodes 13290, 13291. Those portions of the first jaw clamping face 13252 may comprise insulative material. Likewise, in such an embodiment, the second teeth 13276 only encompass the portions of the second jaw clamping face 13272 that are not occupied by the electrode 13292. In other arrangements, the first teeth 13256 also extend over the conductive portions of the electrodes 13290, 13291 and the second teeth 13276 also extend over the conductive portions of the electrode 13292.

Figure 78:
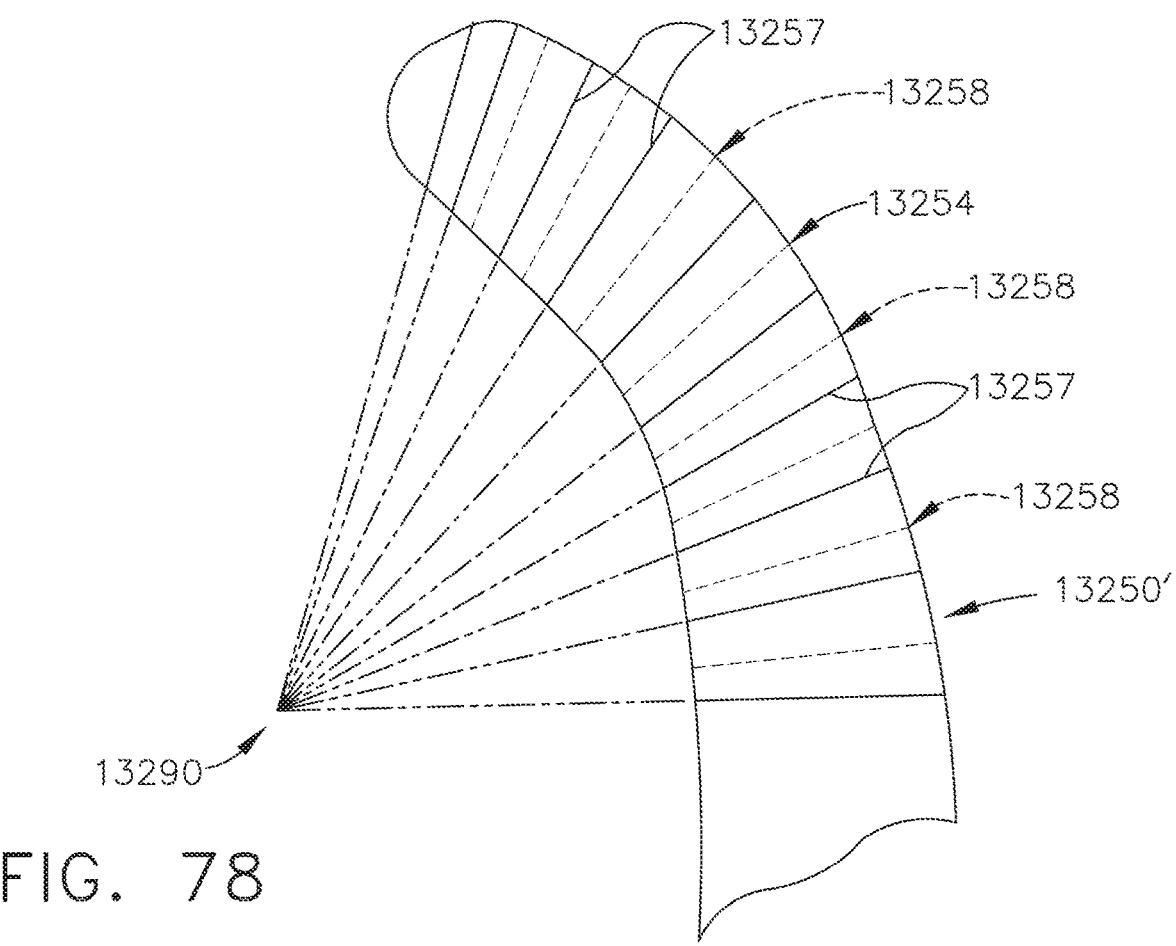
FIG. 78 is a top view of another first jaw, in accordance with at least one aspect of the present disclosure.

In at least one example, each of the first jaw 13250 and the second jaw 13270 include somewhat linear segments that cooperate to form a general curve such that the distal tips 13254, 13274 of each jaw are laterally displaced to a common side of the jaw center axes $FJCA_1$, $SJCA_2$. See FIGS. 68 and 69. FIG. 77 depicts a radial tooth arrangement that is aligned to the average greatest curvature of the jaws even if the jaws include straight portions. FIG. 78 illustrates an alternative first jaw embodiment 13250' that comprises a gentle curve that is formed without any linear segments/sidewalls.

Figure 79:
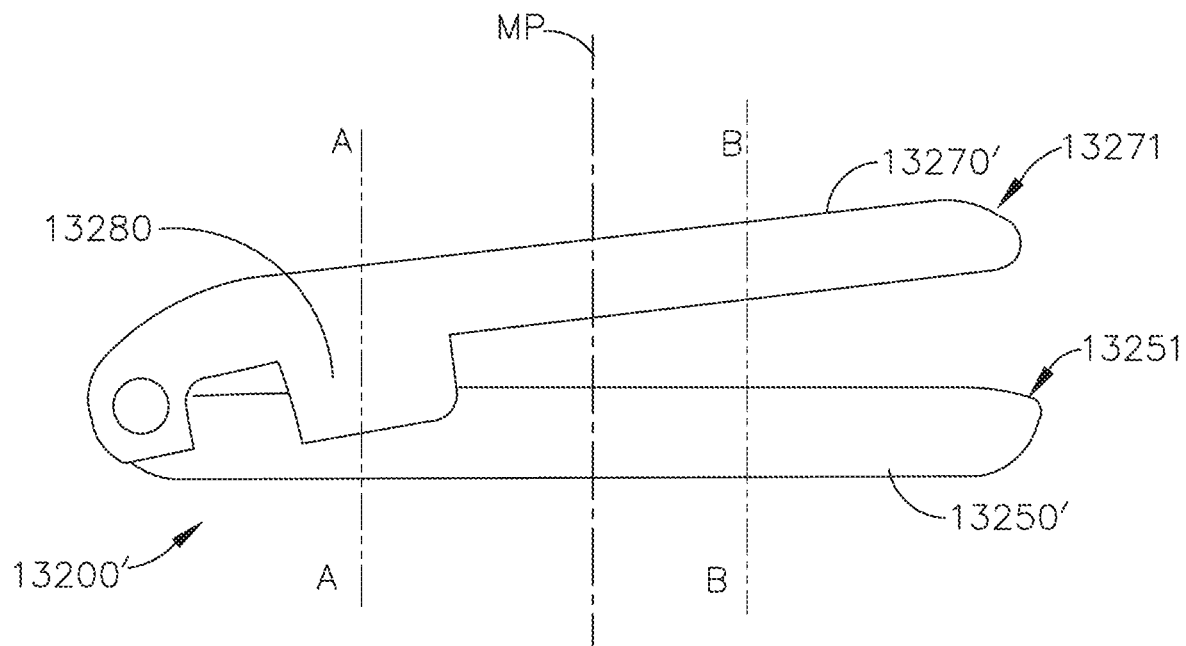
FIG. 79 is a diagrammatical side view of a surgical end effector embodiment with jaws thereof in an open position, in accordance with at least one aspect of the present disclosure.
Figure 80:
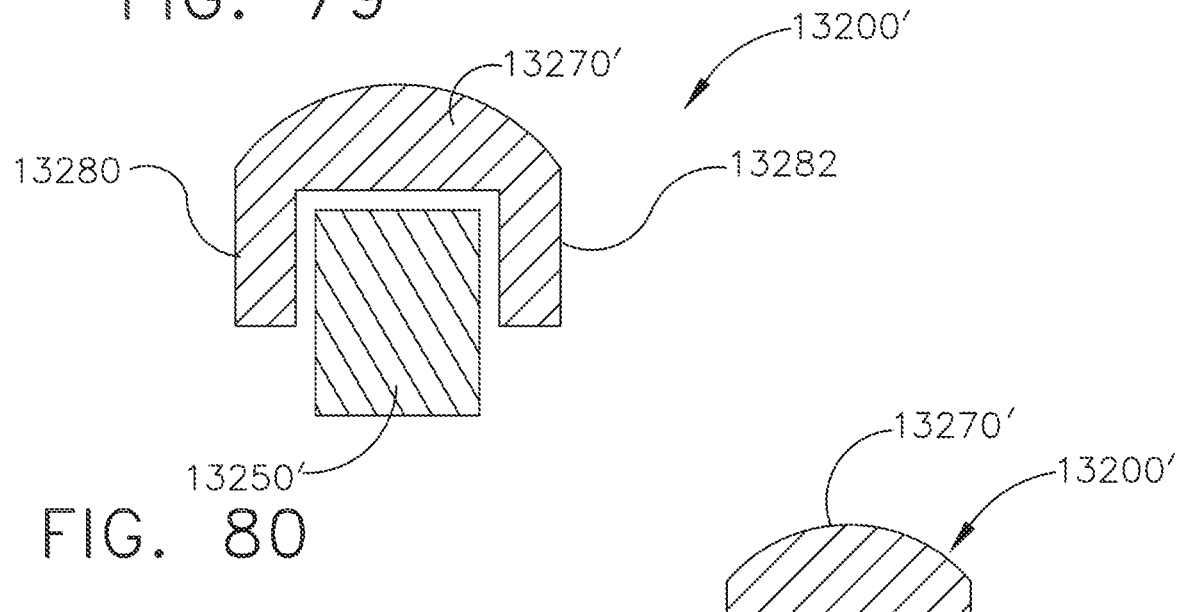
FIG. 80 is a cross-sectional end view of the surgical end effector of FIG. 79 taken along line A-A in FIG. 79.
Figure 81:
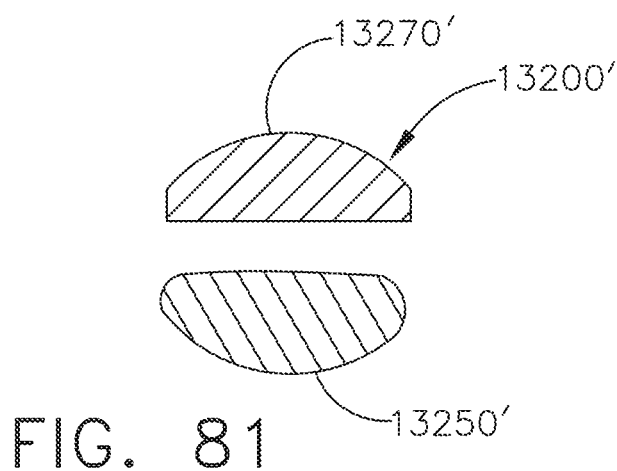
FIG. 81 is another cross-sectional end view of the surgical end effector of FIG. 79 taken along line B-B in FIG. 79.

FIGS. 79-81 illustrate a surgical end effector arrangement 13200' that comprises a first jaw 13250' and a second jaw 13270'. In certain instances, the second jaw 13270' comprises at least one, and preferably two, lateral alignment features 13280, 13282 that serve to laterally engage a corresponding side of the first jaw 13250' during clamping to align the first and second jaws 13250', 13270' during the clamping process. In end effectors that are equipped with bipolar electrodes, the jaws may comprise multiple jaw features which interact within more than one isolated zone in the jaws to cause a physical force to re-align the misaligned jaws and to re-align the electrode in the first jaw with the electrode in the second jaw. In one arrangement, for example, the DLC of the first jaw/electrode set is offset laterally from the electrode in the second jaw/electrode. However, the teeth of each jaw extend within the electrode portion and the insulated portion and the overlap is great enough to allow the distal tips of the jaws to be initially misaligned by the tissue as the radially arrayed teeth begin to engage each other. In one arrangement for example, the insulative portion of the teeth of the first jaw engage the conductive portion of the teeth of the second jaw forcibly realign the distal tips of the first and second jaws along the tooth profile.

Figure 82:
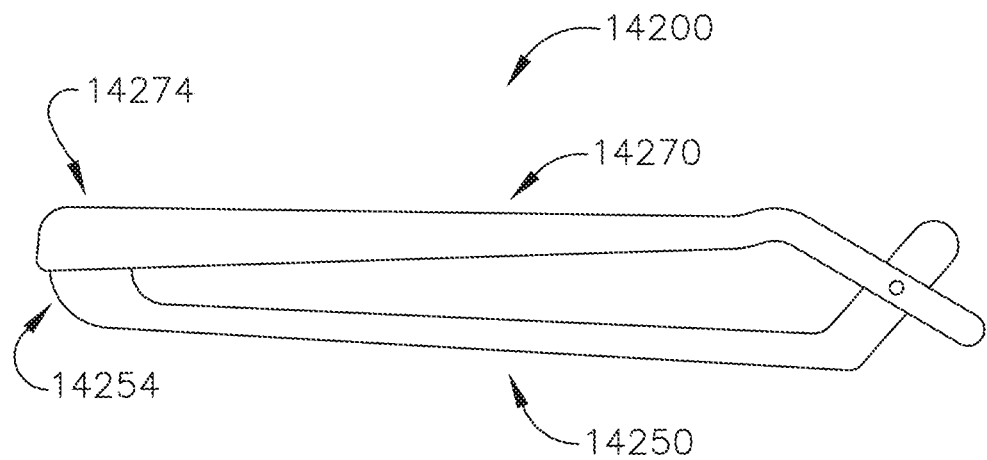
FIG. 82 is a side elevational view of another surgical end effector embodiment with jaws thereof in a closed position, in accordance with at least one aspect of the present disclosure.
Figure 83:
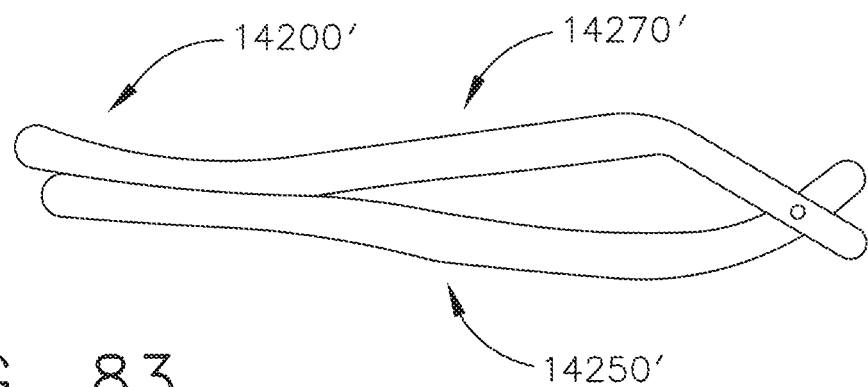
FIG. 83 is a side elevational view of another surgical end effector embodiment with jaws thereof in a closed position, in accordance with at least one aspect of the present disclosure.
Figure 84:
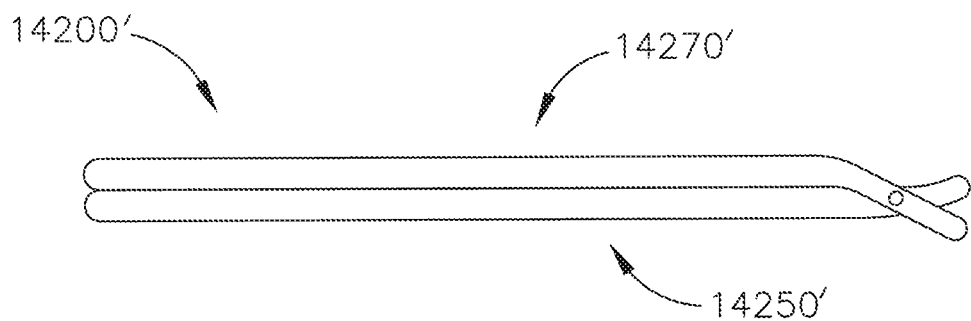
FIG. 84 is a side elevational view of the surgical end effector of FIG. 83 illustrating the jaws thereof in a fully closed position.

In various arrangements, it may be advantageous to employ a surgical end effector that has a jaw closure arrangement that provides for distal-to-proximal jaw closure. For example, FIG. 82 depicts a surgical end effector 14200 that includes a first jaw 14250 and a second jaw 14270 that are movably coupled together in such a way as to induce initial contact between the distal tips 14254 and 14274 of the first and second jaws 14250, 14270, respectively. Such arrangement may comprise an offset pivot between the first jaw 14250 and the second jaw 14270 to camber one of the jaws toward the other jaw. FIGS. 83 and 84 depict a surgical end effector 14200' that includes a first jaw 14250' and a second jaw 14270' that are movably coupled together. The first and second jaws 14250', 14270' progressively elastically deform as the jaws are clamped toward each other. A deflectable proximal operating mechanism may be employed that allows the jaw's clamping load to be increased while minimizing the jaw deflection and delivering uniform loading between the jaws. As illustrated in FIG. 84, the jaws 14250', 14270' may establish a uniform pressure profile when fully clamped.

Figure 85:
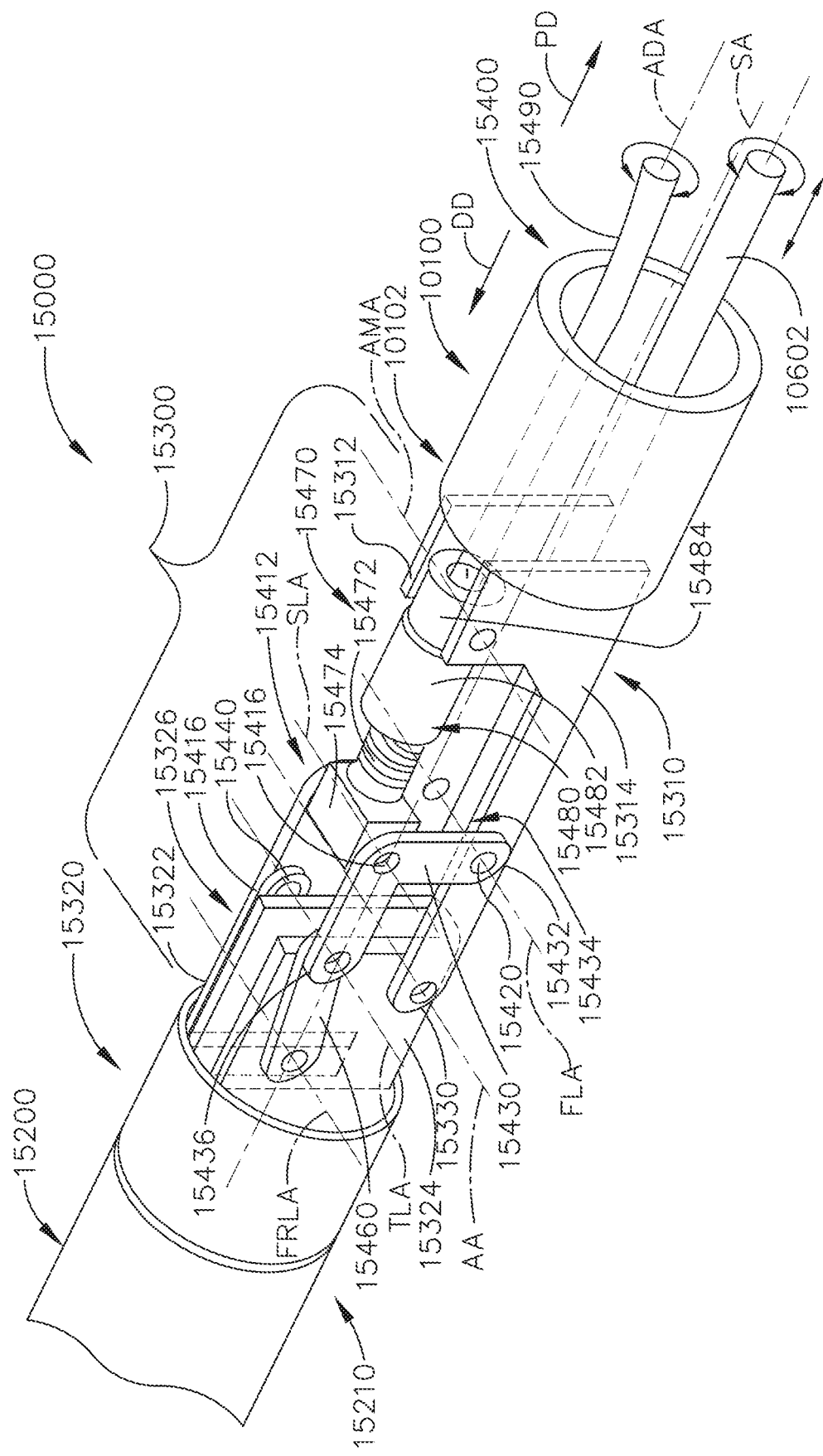
FIG. 85 is a partial perspective view of a portion of a surgical instrument, in accordance with at least one aspect of the present disclosure.
Figure 86:
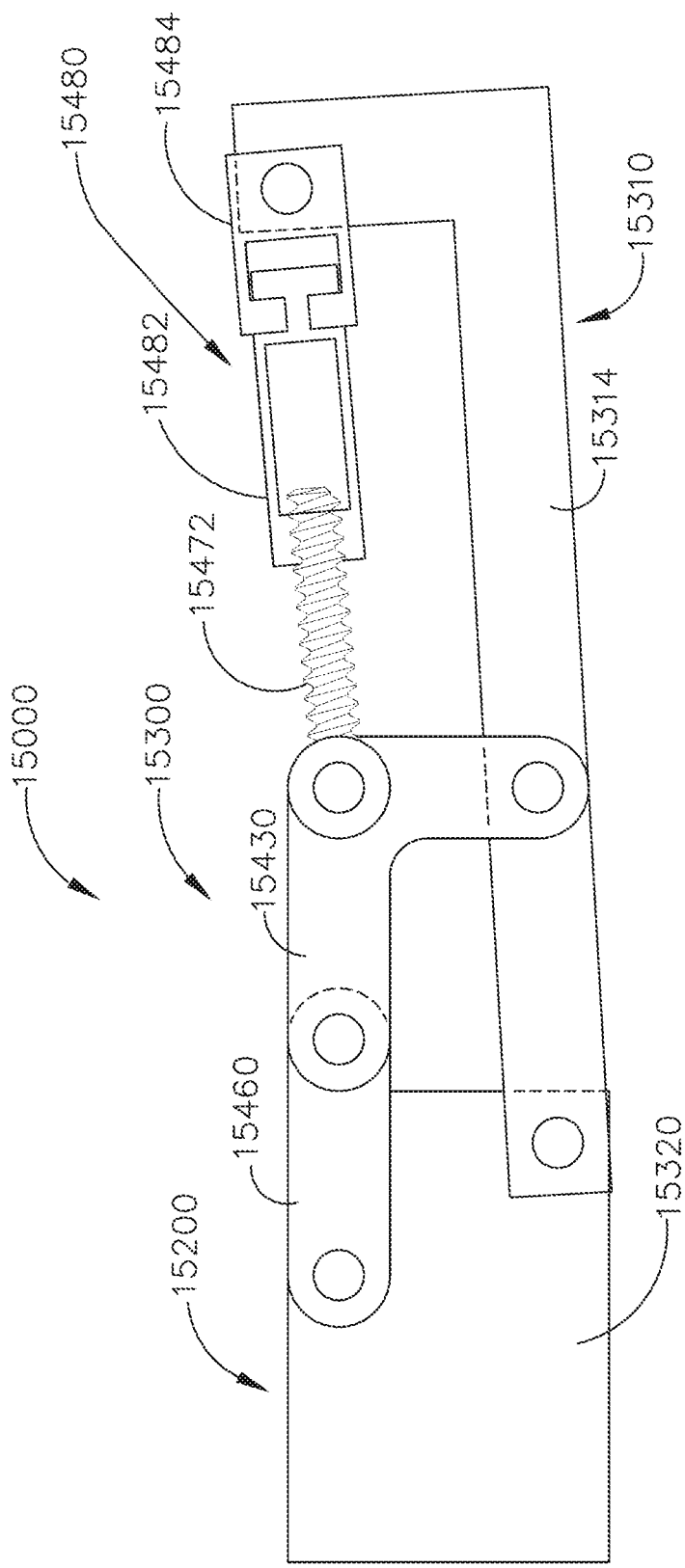
FIG. 86 is a side elevational view of a portion of the surgical instrument of FIG. 85.
Figure 87:
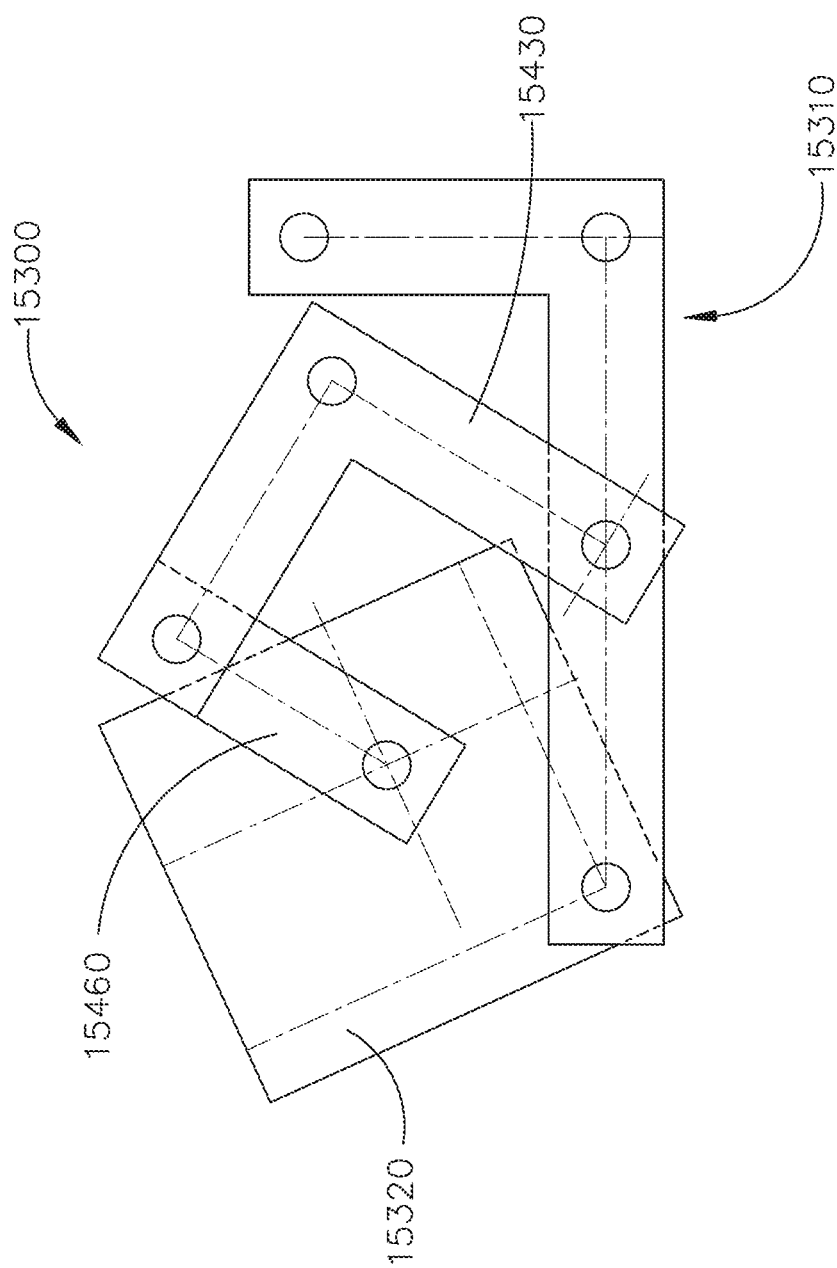
FIG. 87 is a finite element analysis of an articulation joint of the surgical instrument of FIG. 85 articulated in a first direction.

FIG. 85 illustrates another surgical instrument 15000 that comprises a surgical end effector 15200 that may be coupled to a proximal shaft segment 10100 by an articulation joint 15300. In the illustrated arrangement, the articulation joint 15300 comprises a proximal shaft frame member 15310 that extends distally out of a distal end 10102 of the proximal shaft segment 10100. The proximal shaft frame member 15310 may be attached to the proximal outer shaft tube 10110 by, for example, welding, adhesive, etc. In certain instances, the proximal shaft frame member 15310 comprises a U-shaped cradle portion that includes distally extending attachment arms 15312, 15314, wherein attachment arm 15312 is located on one side of the shaft axis SA and the attachment arm 15314 is located on an opposite side of the shaft axis SA.

The articulation joint 15300 further comprises a proximal end effector frame member 15320 that also comprises a portion of an end effector frame assembly 15210. The proximal end effector frame member 15320 comprises two upstanding support sides 15322, 15324 that define a U-shaped cradle 15326. The proximal end effector frame member 15320 is received between the attachment arms 15312, 15314 and is pivotally supported therein by an articulation pin 15330 that defines an articulation axis AA. The articulation joint 15300 facilitates selective articulation of the proximal end effector frame member 15320 through ranges of articulation on each side of the shaft axis SA. For example, the articulation joint 15300 facilitates articulation of the proximal end effector frame member 15320 from an unarticulated position to a first maximum articulated position in a first articulation direction on one side of the shaft axis SA as well as to a second maximum articulated position in a second articulation direction on the opposite side of the shaft axis SA.

The surgical end effector 15200 is selectively articulated about the articulation axis AA relative to the proximal shaft segment 10100 by an articulation system generally designated as 15400. In the illustrated example, the articulation system 15400 comprises a right proximal link 15410 and a right distal link 15440 located on a right side of the shaft axis SA, a left proximal link 15430 and a left distal link 15460 located on a left side of the shaft axis SA. The right proximal link 15410 comprises a right proximal link body 15412 that is roughly L-shaped and comprises a right proximal link proximal end (not shown) and a right proximal link distal end 15416. Similarly, the left proximal link 15430 comprises a left proximal link body 15432 that is roughly L-shaped and comprises a left proximal link proximal end 15434 and a left proximal link distal end 15436. In the illustrated example, the right proximal link proximal end is pivotally supported relative to the attachment arm 15312 and the left proximal link proximal end 15434 is pivotally supported relative to the attachment arm 15314. The right proximal link proximal end is pivotally coupled to the attachment arm 15312 and the left proximal link proximal end 15434 is pivotally coupled to the attachment arm 15314 by a first link pin 15420. The first link pin 15420 defines a first link axis FLA that is transverse to the shaft axis SA and facilitates pivotal travel of the right proximal link 15410 and the left proximal link 15430 about the first link axis FLA relative to the proximal shaft frame member 15310.

In at least one arrangement, a proximal end of the right distal link 15440 is pivotally pinned to the right proximal link distal end 10416. A distal end of the right distal link 15440 is pivotally coupled to the support side 15322 of the effector frame member 15320. Similarly, a proximal end of the left distal link 15460 is pivotally pinned to the left proximal link distal end 15436. A distal end of the left distal link 15460 is pivotally pinned to the upstanding support side 15324 of the end effector frame member 15320. The proximal end of the right distal link 15440 is pivotally coupled to the right proximal link distal end 15416 for pivotal travel about a third link axis TLA and the proximal end of the left distal link 15460 is pivotally coupled to the left proximal link 15430 for pivotal travel about the third link axis TLA. The distal end of the right distal link 15440 is pinned to the upstanding support side 15322 of the end effector frame member 15320 for pivotal travel about a fourth link axis FRLA and the distal end of the left distal link 15460 is pivotally pinned to the upstanding support side 15324 of the end effector frame member 15320 for pivotal travel about the fourth link axis FRLA.

In certain instances, the articulation system 15400 further comprises an axially movable articulation actuator 15470 that is configured to apply axial articulation motions to the right proximal link 15410 and the left proximal link 15430. In the illustrated arrangement, the articulation actuator 15470 comprises a distal articulation shaft segment 15472 that threadably interfaces with an articulation drive nut 15480. The articulation drive 15480 comprises a threaded portion 15482 that is configured to rotate about an articulation drive axis ADA and a mount portion 15484 that is pivotally coupled to the proximal shaft frame member 15310. The mount portion 15484 facilitates pivotal travel of the articulation drive 15480 about an articulation mount axis AMA that is transverse to the articulation drive axis ADA. A rotary driven proximal articulation drive shaft 15490 is coupled to the threaded portion 15482 of the mount portion 15480 such that the threaded portion 15482 is rotatable by the proximal articulation drive shaft 15490 relative to the mount portion 15484. Rotation of the threaded portion 15482 results in axial travel of the distal articulation shaft segment 15472.

Figure 88:
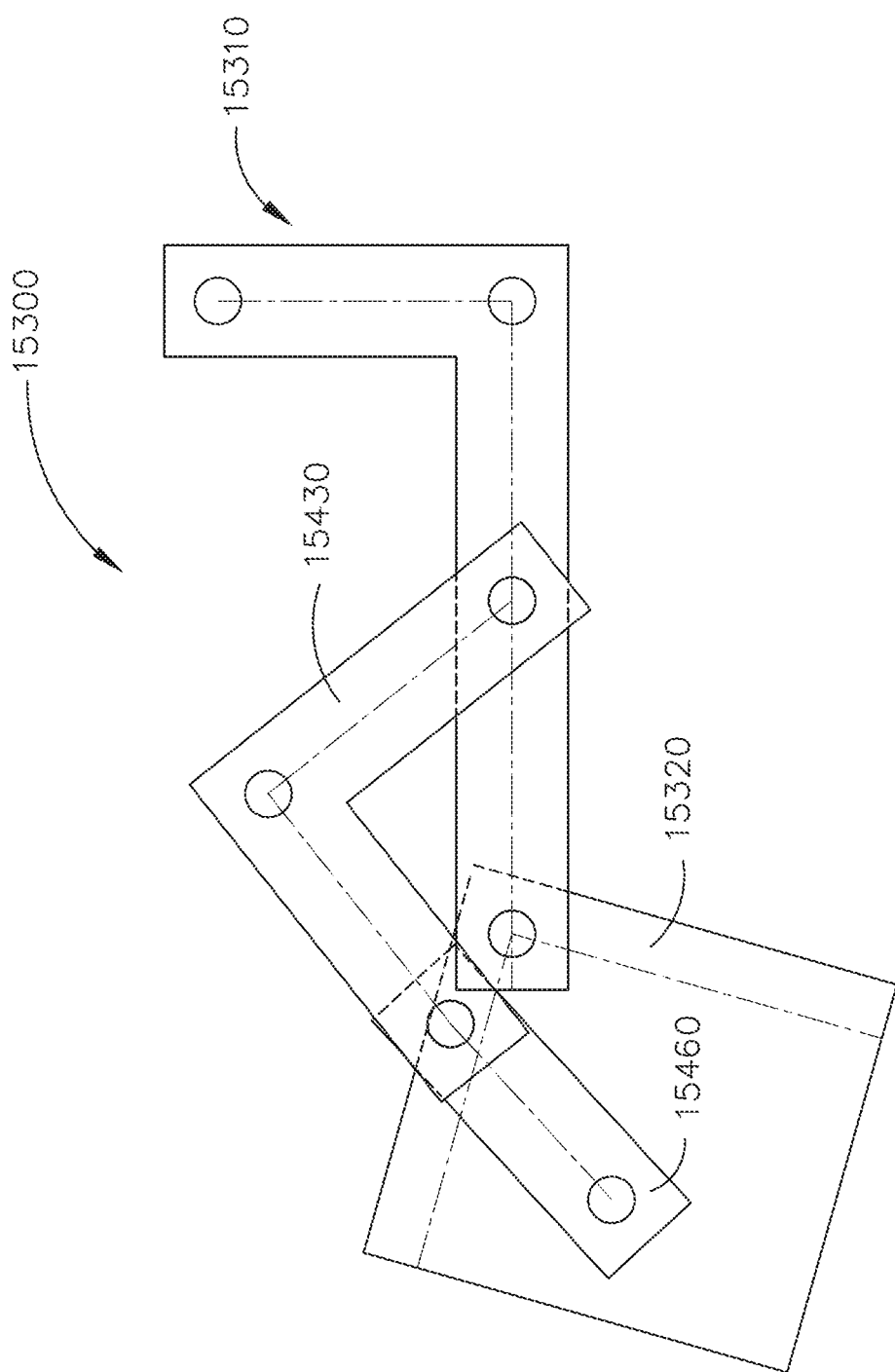
FIG. 88 is another finite element analysis of the articulation joint of the surgical instrument of FIG. 85 articulated in a second direction.

In the illustrated example, the distal articulation shaft segment 15472 includes a distal end formation 15474 that is pivotally coupled to the right proximal link 15410 and the left proximal link 15430 about the second link axis SLA. The surgical end effector 15200 may be selectively articulated about the articulation axis AA by moving the distal end formation 15474 in a proximal direction PD or in a distal direction DD. The surgical instrument 15000 further includes a flexible rotary shaft 10602 that is capable of rotation while being able to bend and flex to accommodate articulation of the surgical end effector 15200 in the manners described herein. The flexible rotary shaft 10602 is configured to open and close the jaws (not shown) of the surgical end effector 15200 in the various manners disclosed herein. Likewise, rotation of the flexible rotary drive shaft 10602 will cause the surgical end effector 15200 to rotate about the shaft axis SA in the various manners disclosed herein. FIGS. 88 and 89 comprise a finite element analysis of the components of one form of articulation system 15300 described above.

FIG. 89 and FIG. 90 depict another articulation system arrangement 16300 that is configured to selectively articulate a surgical end effector 16200. In this arrangement, the surgical end effector 16200 is pivotally coupled to a shaft (not shown) at an articulation point 16302 for articulation relative thereto. The articulation system arrangement 16300 comprises a right articulation member 16310 and a left articulation member 16320. The right articulation member 16320 is pivotally coupled to the surgical end effector 16200 and operably interfaces with an articulation drive arrangement in a housing (not shown) that is configured to apply axial articulation control motions thereto. Likewise, the left articulation member 16320 is pivotally coupled to the surgical end effector 16200 and operably interfaces with an articulation drive arrangement in a housing that is configured to apply axial articulation control motions thereto. FIG. 810 illustrates articulation of the surgical end effector 16200 to the left wherein the right articulation member 16310 is axially advanced in the distal direction DD and the left articulation member 16320 is axially advanced in the proximal direction PD.

Figure 91:
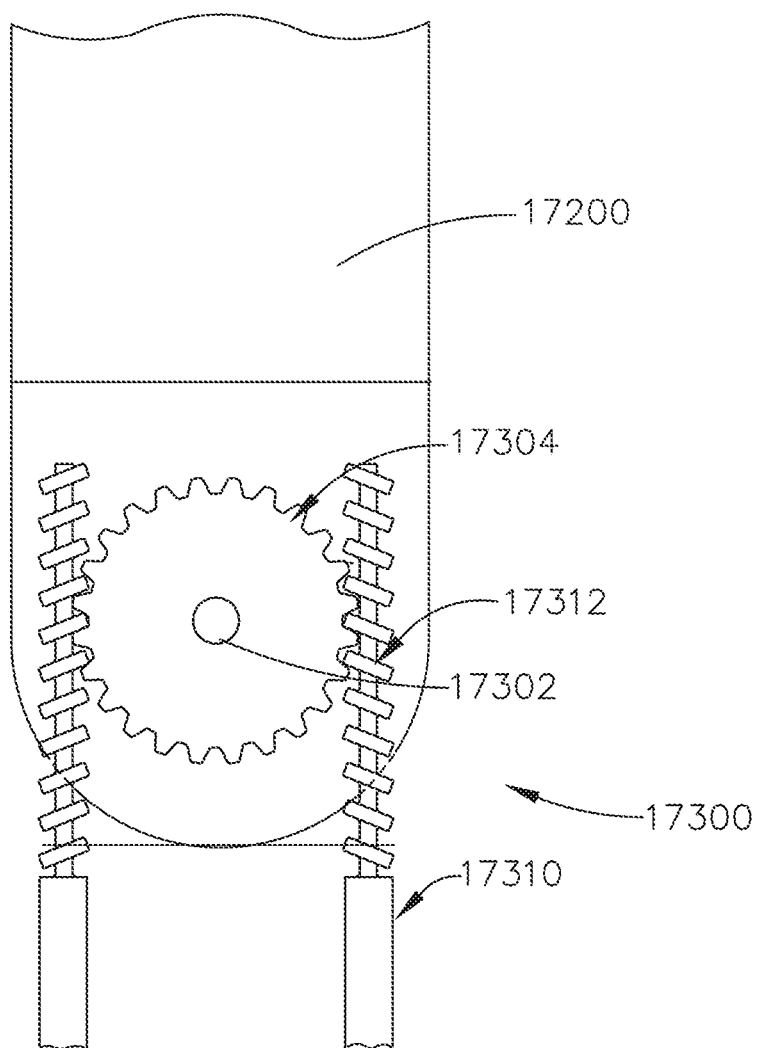
FIG. 91 is a partial view of another surgical instrument with a surgical end effector in an unarticulated position, in accordance with at least one aspect of the present disclosure.

FIG. 91 depicts another articulation system arrangement 17300 that is configured to selectively articulate a surgical end effector 17200. In this arrangement, the surgical end effector 17200 is pivotally coupled to a shaft (not shown) at an articulation point 17302 for articulation relative thereto. The articulation system arrangement 17300 comprises a winch-style drive mechanism 17310 that includes a worm gear 17312 that meshingly interfaces with a worm wheel 17304 that is operably coupled to the surgical end effector 17200. The winch-style drive mechanism 17310 interfaces with a control system, motor, etc. operably supported in a housing (not shown). Operation of the winch-style drive mechanism 17310 will result in the articulation of the surgical end effector 17200 about the articulation point 17302.

Figure 92:
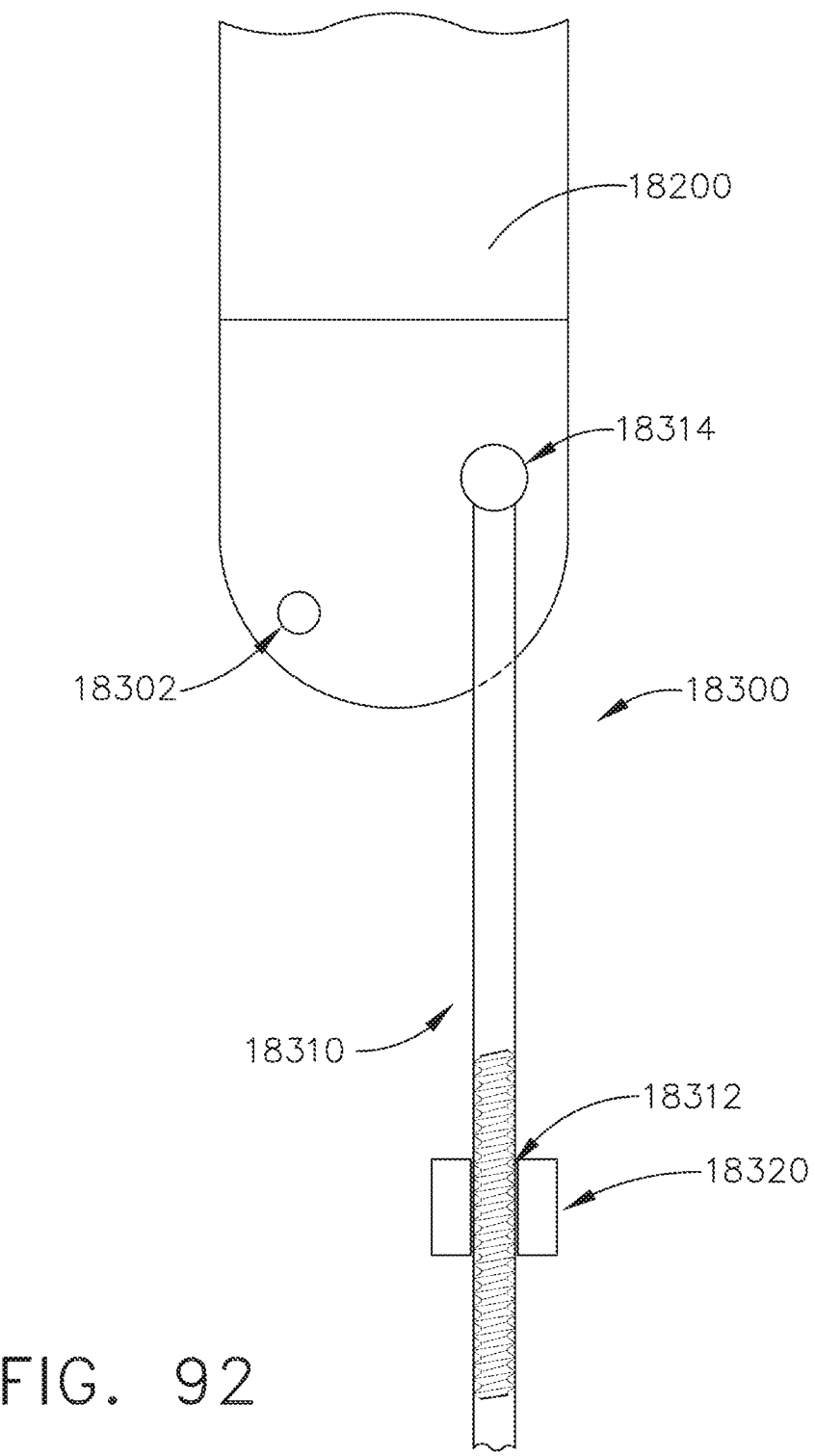
FIG. 92 is a partial view of another surgical instrument with a surgical end effector in an unarticulated position, in accordance with at least one aspect of the present disclosure.

FIG. 92 depicts another articulation system arrangement 18300 that is configured to selectively articulate a surgical end effector 18200. In this arrangement, the surgical end effector 18200 is pivotally coupled to a shaft (not shown) at an articulation point 18302 for articulation relative thereto. The articulation system arrangement 18300 comprises an articulation drive member 18310 that comprises a threaded rod 18312 that is attached to the surgical end effector 18200 by a ball and socket arrangement 18314. The threaded rod 18312 is in threaded engagement with a threaded nut 18320 fixedly supported in the shaft. The threaded rod 18312 operably interfaces with an articulation drive arrangement in a housing (not shown) that is configured to apply rotary articulation control motions thereto. Rotation of the threaded rod 18312 applies axial articulation motions to the surgical end effector 18200 to pivot the surgical end effector 18200 relative to the shaft assembly about the articulation point 18302.

Figure 94:
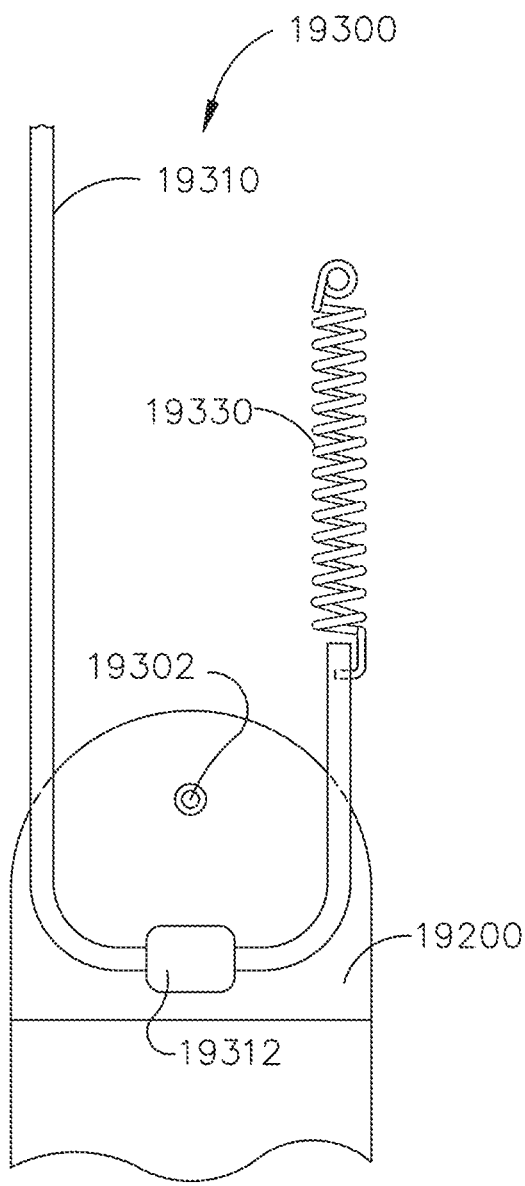
FIG. 94 is a partial view of another surgical instrument with a surgical end effector in an unarticulated position, in accordance with at least one aspect of the present disclosure.
Figure 93:
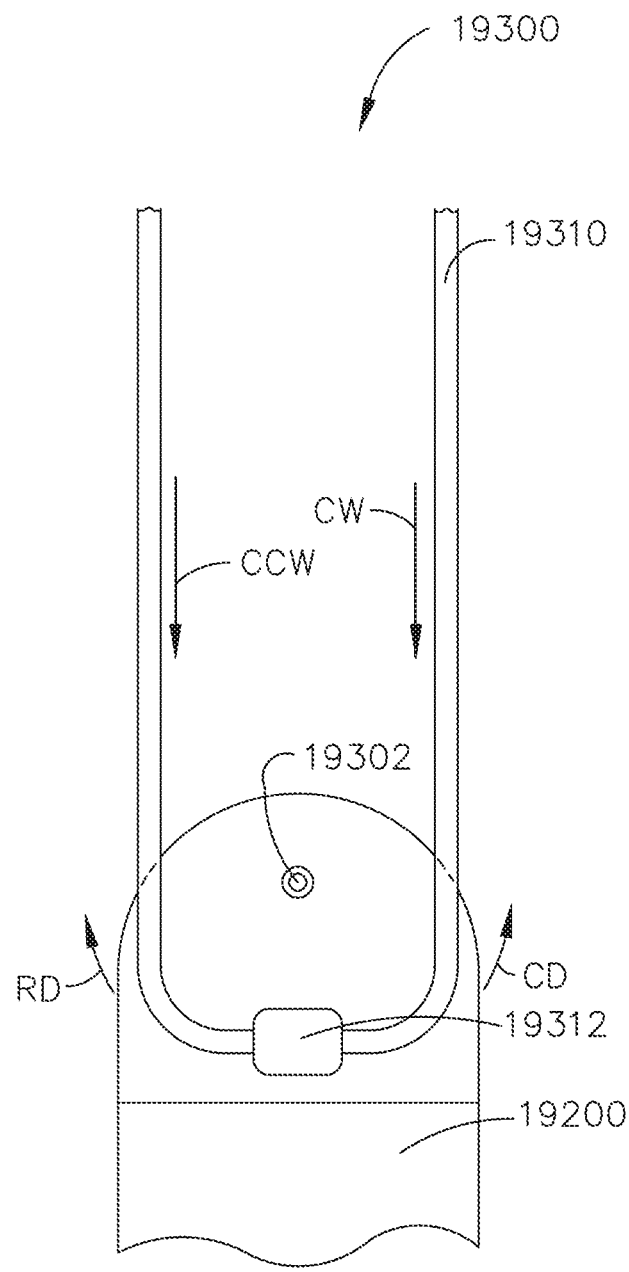
FIG. 93 is a partial view of another surgical instrument with a surgical end effector in an unarticulated position, in accordance with at least one aspect of the present disclosure.

FIG. 93 depicts another articulation system arrangement 19300 that is configured to selectively articulate a surgical end effector 19200. In this arrangement, the surgical end effector 19200 is pivotally coupled to a shaft (not shown) at an articulation point 19302 for articulation relative thereto. The articulation system arrangement 19300 comprises a closed loop tungsten cable 19310 that is attached to the surgical end effector 19200 at an attachment point 19312. Rotation of the cable 19310 in a clockwise direction CW will result in articulation of the surgical end effector 19200 in a right direction RD and rotation of the cable 19310 in a counterclockwise direction CCW will result in articulation of the surgical end effector 19200 in a left direction LD. FIG. 94 illustrates use of a spring 19330 to apply a counter force to the cable 19310 to return the surgical end effector 19200 to an unarticulated position when articulation tension is relieved in the cable 19310.

Various aspects of the subject matter described herein are set out in the following examples.

Example 1—A surgical instrument comprising a surgical end effector that comprises an end effector frame assembly. A proximal shaft segment defines a shaft axis and is attached to the end effector frame assembly by an articulation system to facilitate articulation of the end effector frame assembly relative to the proximal shaft segment about an articulation axis that is transverse to the shaft axis. The articulation system comprises a first link that comprises a first link proximal end that is pivotally coupled to the proximal shaft segment. The first link further comprises a first link distal end. The articulation system further comprises a second link that comprises a second link proximal end that is pivotally coupled to the first link distal end. The second link further comprises a second link distal end that is pivotally coupled to the end effector frame assembly. The articulation system further comprises an axially movable articulation actuator that operably interfaces with the first link at a location between the first link proximal end and the first link distal end to apply articulation motions thereto.

Example 2—The surgical instrument of Example 1, wherein the first link comprises a right proximal link that comprises a right proximal link proximal end that is pivotally coupled to the proximal shaft segment on a right side of the shaft axis. The right proximal link further comprises a right proximal link distal end. The first link further comprises a left proximal link that comprises a left proximal link proximal end that is pivotally coupled to the proximal shaft segment on a left side of the shaft axis. The left proximal link further comprises a left proximal link distal end. The second link proximal end is pivotally coupled to the right proximal link distal end and the left proximal link distal end. The axially movable articulation actuator operably interfaces with the right proximal link at a right pivot location on the right proximal link between the right proximal link proximal end and the right proximal link distal end. The axially movable articulation actuator operably interfaces with the left proximal link at a left pivot location on the left proximal link between the left proximal link proximal end and the left proximal link distal end.

Example 3—The surgical instrument of Example 2, wherein the axially movably articulation actuator pivotally interfaces with the right proximal link at the right pivot location, and wherein the axially movable articulation actuator pivotally interfaces with the left proximal link at the left pivot location.

Example 4—The surgical instrument of Examples 2, or 3, wherein the second link proximal end is pivotally coupled to the right proximal link distal end and the left proximal link distal end.

Example 5—The surgical instrument of Examples 2, 3 or 4, wherein the second link proximal end spans transversely across the shaft axis and is pivotally coupled to the right proximal link distal end and the left proximal link distal end.

Example 6—The surgical instrument of Examples 2, 3, 4 or 5, wherein the second link proximal end is centrally disposed between the right proximal link distal end and the left proximal link distal end.

Example 7—The surgical instrument of Examples 2, 3, 4, 5 or 6, further comprising a drive member that extends between the right proximal link and the left proximal link to apply a drive motion to the surgical end effector.

Example 8—The surgical instrument of Example 7, wherein the drive motion comprises a rotary drive motion.

Example 9—The surgical instrument of Example 7, wherein the drive motion comprises an axial drive motion.

Example 10—The surgical instrument of Example 7, wherein the drive motion comprises a first rotary drive motion and a second axial drive motion.

Example 11—The surgical instrument of Examples 7, 8, 9 or 10, wherein the drive member comprises a flexible shaft assembly.

Example 12—The surgical instrument of Examples 1, 2, 3, 4, 5, 6, 7, 8, 9, 10 or 11, wherein the surgical end effector further comprises a first jaw that is pivotally supported on the end effector frame assembly and a second jaw that is pivotally supported relative to the first jaw. The first jaw and the second jaw are pivotable relative to each other between an open position and a closed position upon axial control motions applied to one of the first jaw and the second jaw.

Example 13—The surgical instrument of Examples 1, 2, 3, 4, 5, 6, 7, 8, 9, 10, 11 or 12, wherein the second link is U-shaped.

Example 14—The surgical instrument of Examples 1, 2, 3, 4, 5, 6, 7, 8, 9, 10, 11, 12 or 13, wherein the second link distal end comprises a left second link arm that is coupled to the second link proximal end and a right second link arm that is coupled to the second link proximal end. The left second link arm is spaced from the right second link arm and wherein the left second link arm and the right second link arm are pivotally coupled to the end effector frame assembly by an end effector link pin.

Example 15—A surgical instrument comprising a surgical end effector that comprises an end effector frame assembly. A first jaw is pivotally coupled to the end effector frame assembly. A second jaw is pivotally coupled to the first jaw, wherein the first jaw and the second jaw are pivotally movable between an open position and a closed position upon application of axial control motions to the second jaw. The surgical instrument further comprises a proximal shaft segment that defines a shaft axis, wherein the proximal shaft segment is attached to the end effector frame assembly by an articulation system to facilitate articulation of the end effector frame assembly relative to the proximal shaft segment about an articulation axis that is transverse to the shaft axis. The articulation system comprises a first link that comprises a first link proximal end that is pivotally coupled to the proximal shaft segment. The first link further comprises a first link distal end. The articulation system further comprises a second link that comprises a second link proximal end that is pivotally coupled to the first link distal end. The second link further comprises a second link distal end that is pivotally coupled to the end effector frame assembly. The articulation system further comprises an axially movable articulation actuator that operably interfaces with the first link at a location between the first link proximal end and the first link distal end to apply articulation motions thereto. The surgical instrument further comprises a drive member that extends between the right proximal link and the left proximal link. The drive member is coupled to the second jaw to apply the axial control motions thereto.

Example 16—The surgical instrument of Example 15, wherein the second link is U-shaped.

Example 17—The surgical instrument of Examples 15 or 16, wherein the proximal shaft segment comprises a proximal outer shaft tube that defines an outer diameter and a proximal retainer member that protrudes distally from a distal end of the proximal outer shaft tube and is pivotally coupled to the end effector frame assembly to facilitate articulation of the end effector frame assembly relative to the proximal retainer member about the articulation axis and wherein the first link proximal end is pivotally coupled to the proximal retainer member.

Example 18—The surgical instrument of Example 17, wherein the first link comprises a right proximal link that comprises a right proximal link proximal end that is pivotally coupled to the proximal retainer member on a right side of the shaft axis and a right proximal link distal end. The first link further comprises a left proximal link that comprises a left proximal link proximal end that is pivotally coupled to the proximal retainer member on a left side of the shaft axis and a left proximal link distal end. The second link proximal end is pivotally coupled to the right proximal link distal end and the left proximal link distal end. The axially movable articulation actuator operably interfaces with the right proximal link at a right pivot location on the right proximal link between the right proximal link proximal end and the right proximal link distal end. The axially movable articulation actuator operably interfaces with the left proximal link at a left pivot location on the left link between the left proximal link proximal end and the left proximal link distal end.

Example 19—The surgical instrument of Example 18, wherein the right proximal link and the left proximal link do not extend outward beyond the outer diameter of the proximal outer shaft tube.

Example 20—The surgical instrument of Examples 18 or 19, wherein the right proximal link defines a right radiused outer surface located between the right proximal link proximal end and the right proximal link distal end. The left proximal link defines a left radiused outer surface located between the left proximal link proximal end and the left proximal link distal end.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In various aspects, a control circuit as used herein is coupled to one or more feedback systems that can be employed by the control circuit to perform predetermined functions such as, for example, issuing an alert when one or more predetermined conditions are met. In certain instances, the feedback systems may comprise one or more visual feedback systems such as display screens, backlights, and/or LEDs, for example. In certain instances, the feedback systems may comprise one or more audio feedback systems such as speakers and/or buzzers, for example. In certain instances, the feedback systems may comprise one or more haptic feedback systems, for example. In certain instances, the feedback systems may comprise combinations of visual, audio, and/or haptic feedback systems, for example.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to,"

"related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The Entire Disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:
a surgical end effector comprising an end effector frame assembly; and
a proximal shaft segment defining a shaft axis, wherein said proximal shaft segment is attached to said end effector frame assembly by an articulation system to facilitate articulation of said end effector frame assembly relative to said proximal shaft segment about an articulation axis that is transverse to said shaft axis, wherein said articulation system comprises:
a first link comprising:
a first link proximal end pivotally coupled to said proximal shaft segment; and
a first link distal end, wherein said articulation system further comprises:
a second link, comprising:
a second link proximal end pivotally coupled to said first link distal end; and
a second link distal end pivotally coupled to said end effector frame assembly, wherein said articulation system further comprises an axially movable articulation actuator pivotally pinned to said first link at a location between said first link proximal end and said first link distal end to apply articulation motions thereto, and wherein axial movement of said axially movable articulation actuator only in a proximal axial direction causes articulation of said end effector frame assembly in a first articulation direction and articulation of said axially movable articulation actuator only in a distal axial direction causes articulation of said end effector frame assembly in a second articulation direction.

2. The surgical instrument of claim 1, wherein said first link comprises:
a right proximal link, comprising:
a right proximal link proximal end pivotally coupled to said proximal shaft segment on a right side of said shaft axis; and
a right proximal link distal end, and wherein said first link further comprises:
a left proximal link, comprising:
a left proximal link proximal end pivotally coupled to said proximal shaft segment on a left side of said shaft axis; and
a left proximal link distal end, wherein said second link proximal end is pivotally coupled to said right proximal link distal end and said left proximal link distal end, wherein said axially movable articulation actuator is pivotally pinned to said right proximal link at a right pivot location on said right proximal link between said right proximal link proximal end and said right proximal link distal end, and wherein said axially movable articulation actuator is pivotally pinned to said left proximal link at a left pivot location on said left proximal link between said left proximal link proximal end and said left proximal link distal end.

3. The surgical instrument of claim 2, wherein said second link proximal end spans transversely across said shaft axis and is pivotally coupled to said right proximal link distal end and said left proximal link distal end.

4. The surgical instrument of claim 3, wherein said second link proximal end is centrally disposed between said right proximal link distal end and said left proximal link distal end.

5. The surgical instrument of claim 2, further comprising a drive member extending between said right proximal link and said left proximal link to apply a drive motion to said surgical end effector.

6. The surgical instrument of claim 5, wherein said drive motion comprises a rotary drive motion.

7. The surgical instrument of claim 5, wherein said drive motion comprises an axial drive motion.

8. The surgical instrument of claim 5, wherein said drive motion comprises:
a first rotary drive motion; and
a second axial drive motion.

9. The surgical instrument of claim 8, wherein said drive member comprises a flexible shaft assembly.

10. The surgical instrument of claim 2, wherein said second link distal end comprises:

a left second link arm coupled to said second link proximal end; and a right second link arm coupled to said second link proximal end, wherein said left second link arm is spaced from said right second link arm, and wherein said left second link arm and said right second link arm are pivotally coupled to said end effector frame assembly by an end effector link pin.

11. The surgical instrument of claim 1, wherein said surgical end effector further comprises:
a first jaw pivotally supported on said end effector frame assembly; and
a second jaw pivotally supported relative to said first jaw, wherein said first jaw and said second jaw are pivotable relative to each other between an open position and a closed position upon axial control motions applied to one of said first jaw and said second jaw.

12. The surgical instrument of claim 1, wherein said second link is U-shaped.

13. A surgical instrument, comprising:
a surgical end effector comprising:
an end effector frame assembly;
a first jaw pivotally coupled to said end effector frame assembly; and
a second jaw pivotally coupled to said first jaw, wherein said first jaw and said second jaw are pivotally movable between an open position and a closed position upon application of axial control motions to said second jaw, and wherein said surgical instrument further comprises:
a proximal shaft segment defining a shaft axis, wherein said proximal shaft segment is attached to said end effector frame assembly by an articulation system, wherein said articulation system is configured to facilitate articulation of said end effector frame assembly relative to said proximal shaft segment about an articulation axis that is transverse to said shaft axis, wherein said articulation system comprises:
a right L-shaped proximal link comprising:
a right link proximal end pivotally coupled to said proximal shaft segment; and
a right link distal end, and wherein said articulation system further comprises:
a left L-shaped proximal link comprising:
a left link proximal end pivotally coupled to said proximal shaft segment; and
a left link distal end, and wherein said articulation system further comprises:
a distal link
pivotally coupled to said right link distal end and said left link distal end and said end effector frame assembly, wherein said articulation system further comprises an axially movable articulation actuator, wherein said axially movable articulation actuator is pivotally pinned to said right L-shaped proximal link at a location between said right link proximal end and said right link distal end to apply articulation motions thereto, wherein said axially movable articulation actuator is pivotally pinned to said left L-shaped proximal link at another location between said left link proximal end and said left link distal end to apply articulation motions thereto, and wherein said surgical instrument further comprises:
a drive member coupled to said second jaw to apply said axial control motions thereto.

14. The surgical instrument of claim 13, wherein said distal link is U-shaped.

15. The surgical instrument of claim 13, wherein said proximal shaft segment comprises:
a proximal outer shaft tube defining an outer diameter; and
a proximal retainer member protruding distally from a distal end of said proximal outer shaft tube, wherein said proximal retainer member is pivotally coupled to said end effector frame assembly to facilitate articulation of said end effector frame assembly relative to said proximal retainer member about said articulation axis, wherein said right link proximal end is pivotally coupled to said proximal retainer member, and wherein said left link proximal end is pivotally coupled to said proximal retainer member.

16. The surgical instrument of claim 15, wherein said right L-shaped proximal link and said left L-shaped proximal link do not extend outward beyond said outer diameter of said proximal outer shaft tube.

17. The surgical instrument of claim 16, wherein said right L-shaped proximal link defines a right radiused outer surface located between said right link proximal end and said right link distal end, and wherein said left L-shaped proximal link defines a left radiused outer surface located between said left link proximal end and said left link distal end.

18. A surgical instrument, comprising:
a surgical end effector;
a shaft assembly defining a shaft axis;
an articulation joint coupling said surgical end effector to said shaft assembly, wherein said articulation joint comprises:
a right proximal link comprising a right L-shaped link body comprising a first right link leg portion and a second right link leg portion non-movably extending from the first right link leg portion to define a right link corner portion therebetween;
a left proximal link comprising a left L-shaped link body comprising a first left link leg portion and a second left link leg portion non-movably extending from the first left link leg portion to define a left link corner portion therebetween;
a proximal link pin coupled to said right link corner portion and said left link corner portion and extending therebetween;
an axially movable articulation actuator operably interfacing with said proximal link pin to apply articulation motions thereto; and
a second link pivotally coupled to said surgical end effector and said right proximal link and said left proximal link.

19. The surgical instrument of claim 18, wherein said first right link leg portion defines a right proximal link end, wherein said second right link leg portion defines a right distal link end, wherein said first left link leg portion defines a left proximal link end, wherein said second left link leg portion defines a left distal link end, and wherein said second link is pivotally coupled to said right distal link end and said left distal link end.

20. The surgical instrument of claim 19, further comprising a distal link pin coupled to said right distal link end and said left distal link end, wherein said distal link pin extends between said right distal link end and said left distal link end, and wherein said second link is pivotally coupled to said distal link pin.

21. The surgical instrument of claim 20, wherein said second link comprises:
- a second link proximal end pivotally journaled on said distal link pin;
- a right second link arm protruding from said second link proximal end and pivotally coupled to said surgical end effector; and
- a left second link arm protruding from said second link proximal end and pivotally coupled to said surgical end effector.

22. The surgical instrument of claim 21, wherein said surgical end effector comprises an end effector frame, wherein said end effector frame comprises:
- a right upstanding side; and
- a left upstanding side spaced from said right upstanding side, wherein said right second link arm is pivotally coupled to said right upstanding side, and wherein said left second link arm is pivotally attached to said left upstanding side.

23. The surgical instrument of claim 22, wherein said right upstanding side and said left upstanding side define a U-shaped cradle.

* * * * *